(12) United States Patent
Xia et al.

(10) Patent No.: US 8,367,223 B2
(45) Date of Patent: Feb. 5, 2013

(54) HETEROLEPTIC PHOSPHORESCENT EMITTERS

(75) Inventors: Chuanjun Xia, Lawrenceville, NJ (US); Raymond Kwong, Plainsboro, NJ (US); Dinesh Rayabarapu, Waldwick, NJ (US); Bin Ma, Plainsboro, NJ (US)

(73) Assignee: Universal Display Corporation, Ewing, NJ (US)

( * ) Notice: Subject to any disclaimer, the term of this patent is extended or adjusted under 35 U.S.C. 154(b) by 502 days.

(21) Appl. No.: 12/615,660

(22) Filed: Nov. 10, 2009

(65) Prior Publication Data

US 2010/0141127 A1 Jun. 10, 2010

Related U.S. Application Data

(60) Provisional application No. 61/113,257, filed on Nov. 11, 2008.

(51) Int. Cl.
*H01L 51/54* (2006.01)
*C09K 11/06* (2006.01)

(52) U.S. Cl. .......... 428/690; 428/917; 313/504; 257/40; 257/E51.044; 546/4; 548/108

(58) Field of Classification Search ........................ None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,193,088 B2 * | 3/2007 | Cheng et al. | 548/103 |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2001/0019782 A1 * | 9/2001 | Igarashi et al. | 428/690 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Baldo et al., "Highly Efficient Phosphorescent Emission from Organic Electroluminescent Devices," Nature, vol. 395, 151-154, (1998).

Baldo et al., "Very high-efficiency green organic light-emitting devices based on electrophosphorescence," Appl. Phys. Lett., vol. 75, No. 1, 4-6 (1999).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater., 16(22):2003-2007 (2004).

(Continued)

*Primary Examiner* — Marie R. Yamnitzky

(74) *Attorney, Agent, or Firm* — Kilpatrick Townsend & Stockton LLP

(57) ABSTRACT

Heteroleptic compounds containing phenylpyridine and phenylbenzimidazole are provided. The compounds may be used in organic light emitting devices, particularly as emissive dopants in the emissive layer of such devices.

23 Claims, 6 Drawing Sheets

U.S. PATENT DOCUMENTS

| | | | |
|---|---|---|---|
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 2034538 | 3/2009 |
| EP | 2062959 | 5/2009 |
| EP | 2066150 | 6/2009 |
| EP | 2085450 | 8/2009 |
| JP | 2004/131464 | 4/2004 |
| JP | 200511610 | 1/2005 |
| JP | 2007123392 | 5/2007 |
| JP | 2007254297 | 10/2007 |
| JP | 2008074939 | 10/2009 |
| WO | WO 01/39234 | 5/2001 |
| WO | WO 02/02714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2008/051806 | 5/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009021126 | 2/2009 |
| WO | WO 2009/030981 A2 * | 3/2009 |
| WO | WO 2009050290 | 4/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |

OTHER PUBLICATIONS

Tung, Yung-Liang et al., "Organic Light-Emitting Diodes Based on Charge-Neutral Ru$^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int. Ed., 45:7800-7803 (2006).

Tang, C.W. and VanSLYKE, S.A., "Organic Electroluminescent Diodes," Appl. Phys. Lett., 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(/) Complex-Based Light-Emitting Diodes with Low Turn-On voltage," Appl. Phys. Lett., 74(10):1361-1363 (1999).

Gao, Zhiqiang et al., "Bright-Blue Electroluminescence From a Silyl-Substituted ter-(phenylene-vinylene) derivative," Appl. Phys. Lett., 74(6):865- 867 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Hung, L.S. et al., "Anode Modification in Organic Light-Emitting Diodes by Low-Frequency Plasma Polymerization of $CHF_3$,"Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Wang, Y. et al., "Highly Efficient Electroluminescent Materials Based on Fluorinated Organometallic Iridium Compounds," Appl. Phys. Lett., 79(4):449-451 (2001).

Kwong, Raymond C. et al., "High Operational Stability of Electrophosphorescent Devices," Appl. Phys. Lett., 81(1):162-164 (2002).

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

Okumoto, Kenji et al., "Green Fluorescent Organic Light-Emitting Device with External Quantum Efficiency of Nearly 10%," Appl. Phys. Lett., 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Aonuma, Masaki et al., "Material Design of Hole Transport Materials Capable of Thick-Film Formation in Organic Light Emitting Diodes," Appl. Phys. Lett., 90:183503-1-183503-3 (2007).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

Adachi, Chihaya et al., "High-Efficiency Red Electrophosphorescence Devices," Appl. Phys. Lett., 78(11):1622-1624 (2001).

Wong, Keith Man-Chung et al.,"A Novel Class of Phosphorescent Gold(III) Alkynyl-Based Organic Light-Emitting Devices with Tunable Colour," Chem. Commun., 2906-2908 (2005).

Hamada, Yuji et al., "High Luminance in Organic Electroluminescent Devices with Bis(10-hydroxybenzo[h]quinolinato)beryllium as an Emitter," Chem. Lett., 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4):592-593 (2005).

Mi, Bao-Xiu et al., "Thermally Stable Hole-Transporting Material for Organic Light-Emitting Diode: an Isoindole Derivative," Chem. Mater., 15(16):3148-3151 (2003).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Niu, Yu-Hua et al., "Highly Efficient Electrophosphorescent Devices with Saturated Red Emission from a Neutral Osmium Complex," Chem. Mater., 17(13):3532-3536 (2005).

Lo, Shih-Chun et al., "Blue Phosphorescence from Iridium(III) Complexes at Room Temperature," Chem. Mater., 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota, Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al.,"1,2,4-Triazole Derivative as an Electron Transport Layer in Organic Electroluminescent Devices," *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergard et al., "Langmuir-Blodgett Light-Emitting Diodes of Poly(3-Hexylthiophene): Electro-Optical Characteristics Related to Structure," *Synthetic Metals*, 88:171-177 (1997).

Hu, Nan-Xing et al., "Novel High $T_g$ Hole-Transport Molecules Based on Indolo[3,2-*b*]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Obara et al., "Highly phosphorescent iridium complexes containing both tridentate bis(benzimidazolyl)-benzene or—pyridine and bidentate phenylpyridine: synthesis, photophysical properties, and theoretical study of ir-bis(benzirnidazolyl)benzene complex" Inorganic Chemistry, vol. 45, No. 22, 2006, p. 8907-8921.

International Preliminary Report on Patentability received in related PCT/US2009/063873 application, dated May 17, 2011.

Holmes et al., "Blue Organic Electrophosphorescence Using Exothermic Host-Guest Energy Transfer", Appl. Phys. Lett. 82(15): 2422-2424 (2003).

\* cited by examiner

HETEROLEPTIC PHOSPHORESCENT EMITTERS

This application claims priority to U.S. Provisional Application No. 61/113,257, filed Nov. 11, 2008, the disclosure of which is herein expressly incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel heteroleptic complexes. In particular, the heteroleptic compounds contain phenylpyridine and phenylbenzimidazole. The compounds may be useful in organic light emitting devices (OLEDs).

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure of Formula I:

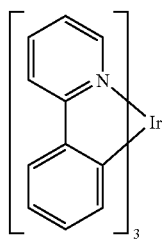

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built. On the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand. More than one type of "photoactive" ligand may be present in a complex. The different photoactive ligands may each contribute to the properties of the emissive material.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Heteroleptic compounds $Ir(L1)_n(L2)_{3-n}$ are provided. The heteroleptic compounds have the formula:

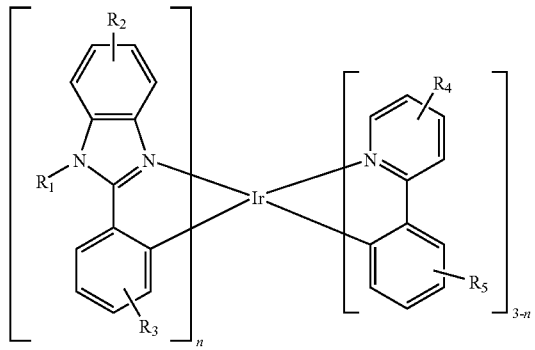

where n=1 or 2,

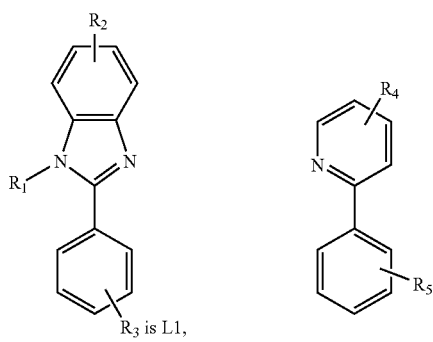

$R_3$ is L1, is L2. $R_1$, $R_2$, $R_3$, $R_4$, and $R_5$ may represent mono, di, tri, or tetra substitutions, and $R_1$, $R_2$, $R_3$, $R_4$, and $R_5$ are each independently selected from the group consisting of hydrogen, alkyl, heteroalkyl, aryl, substituted aryl, heteroaryl, and substituted heteroaryl. Preferably, n is 1. In one aspect, $R_1$ is selected from the group consisting of alkyl, heteroalkyl, substituted aryl, and substituted heteroaryl, where $R_1$ does not form a conjugated system with L1. Preferably, $R_1$ is

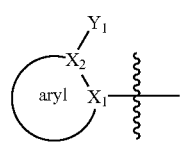

where $X_1$ and $X_2$ are independently selected from C and N. $Y_1$ is not hydrogen. $Y_1$ may be joined to other substituents on the aryl ring. The heteroleptic compound may have a narrower full width at half maximum (FWHM) of emission and/or a lower sublimation temperature than the corresponding homoleptic compounds.

Specific examples of heteroleptic compounds having particular L1 and L2 ligands are provided. Preferably, the heteroleptic compounds are selected from the group consisting of:

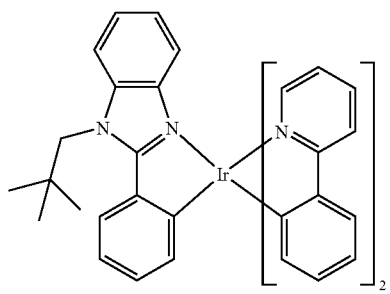

Compound 1

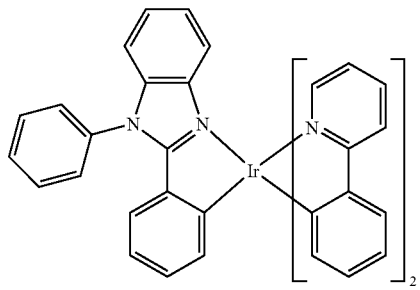

Compound 2

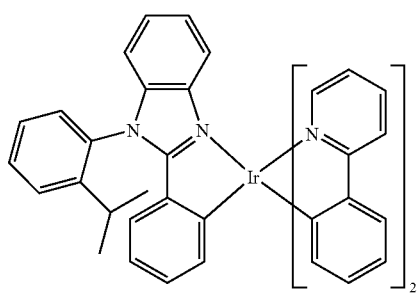

Compound 3

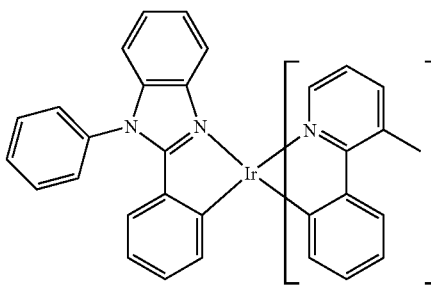

Compound 4

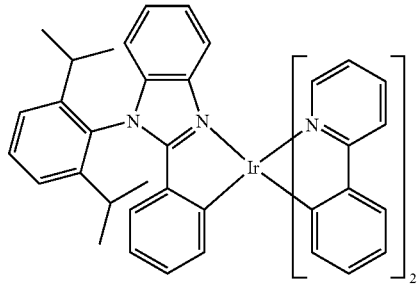

Compound 5

Compound 6
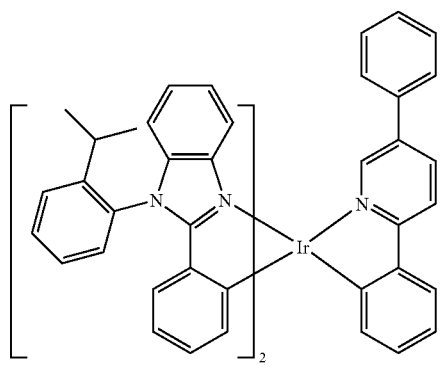
Compound 7
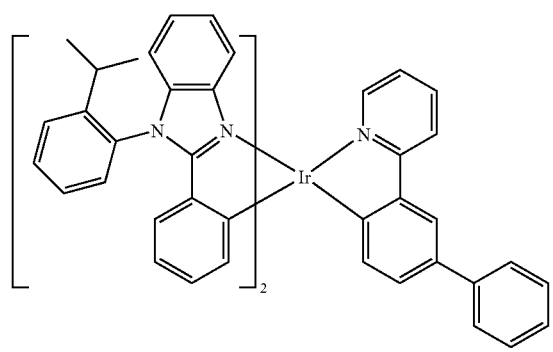
Compound 8
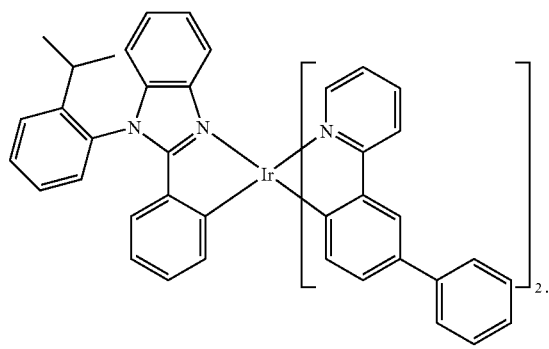
In another aspect, preferably the heteroleptic compound is selected from the group consisting of:
Compound 1
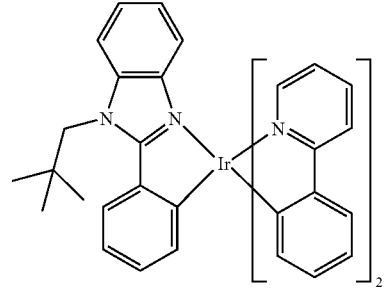
Compound 2
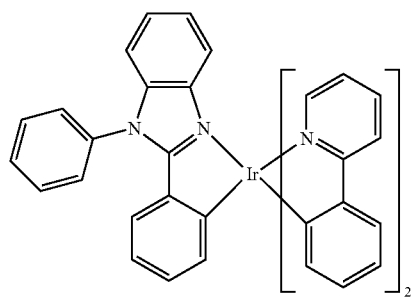
Compound 3
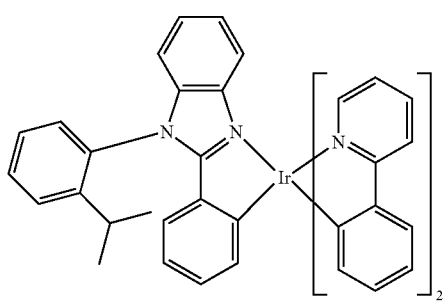
Compound 4
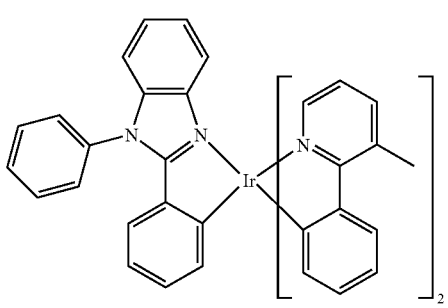
Compound 5
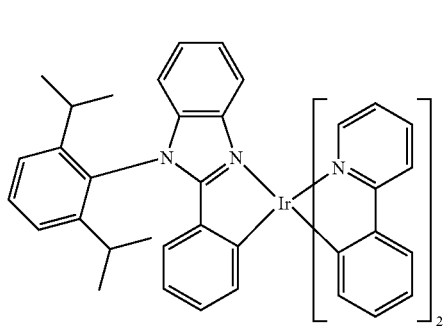
Compound 6
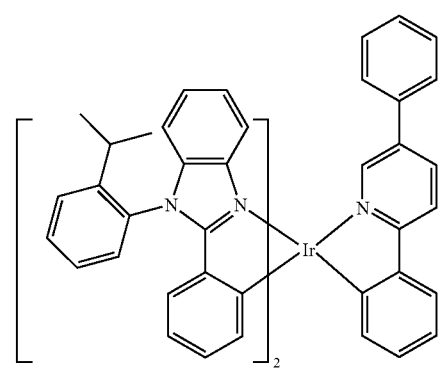

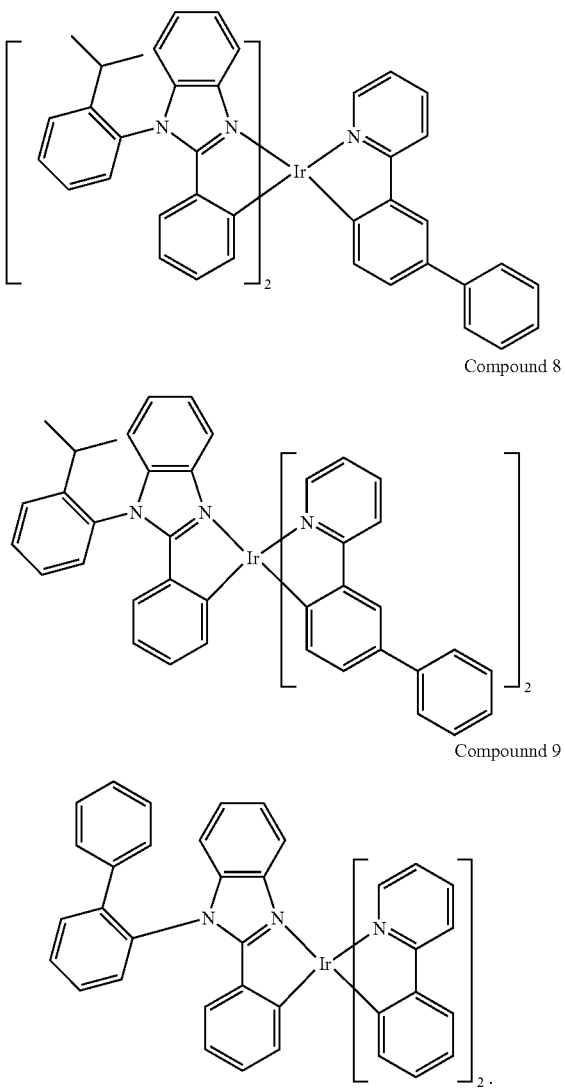

Compound 7

Compound 8

Compounnd 9

An organic light emitting device is also provided. The device has an anode, a cathode, an and an organic layer disposed between the anode and the cathode. The organic layer further comprises a heteroleptic compound $Ir(L1)_n(L2)_{3-n}$, as described above. Preferably the organic layer is an emissive layer having a host and an emissive dopant, and the heteroleptic compound is the emissive dopant.

A consumer product is also provided. The product contains a device that has an anode, a cathode, and an emissive layer disposed between the anode and the cathode, where the organic layer further comprises a heteroleptic compound $Ir(L1)_n(L2)_{3-n}$, as described above.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
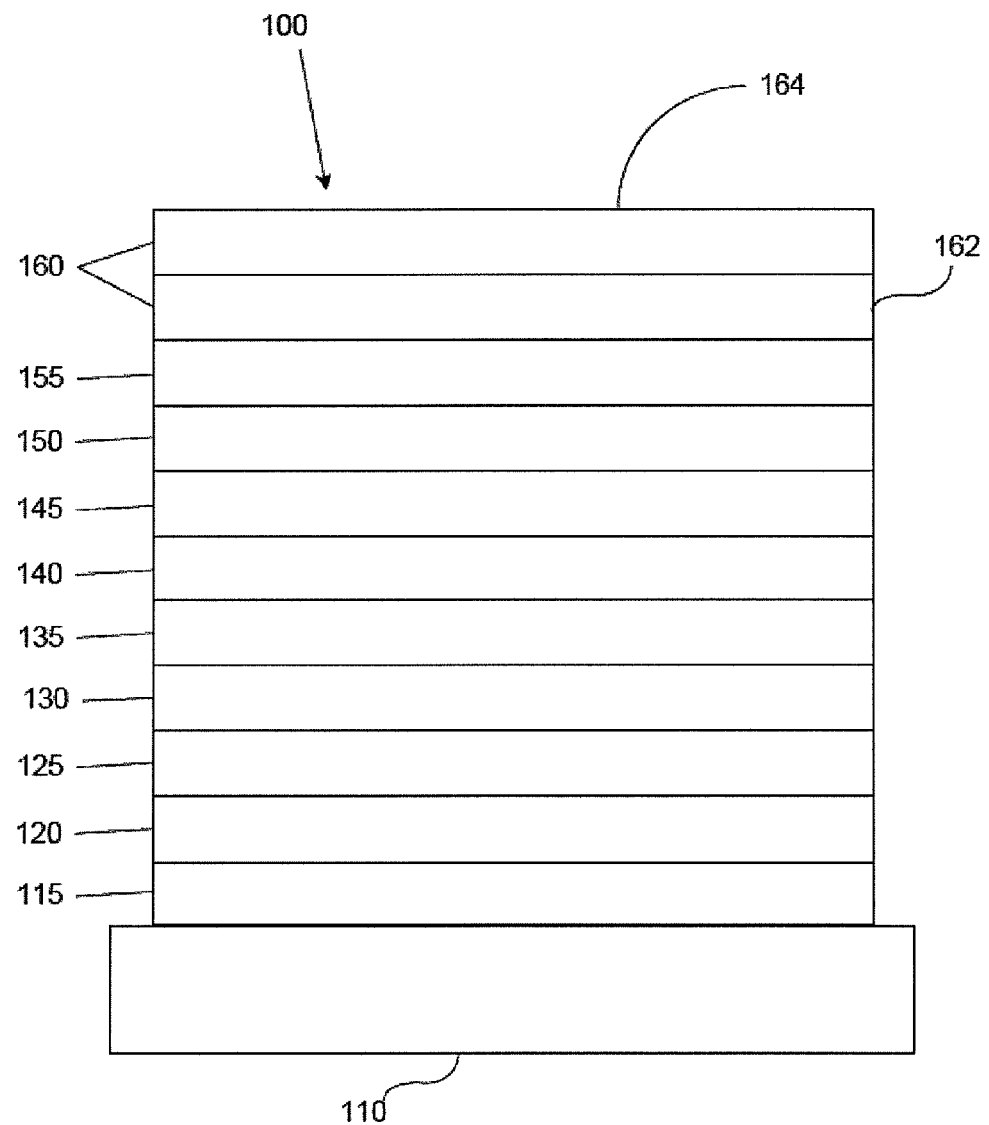
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279, 704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F.sub.4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with L1 at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
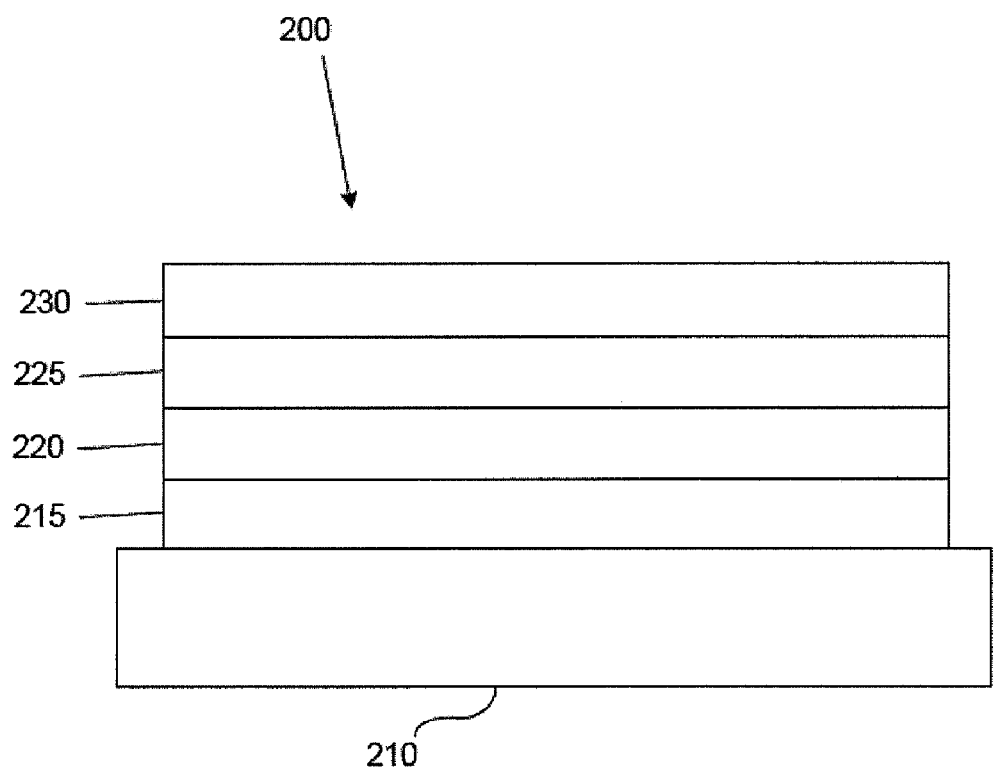
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, aryalkyl, heterocyclic group, aryl, aromatic group, and heteroaryl are known to the art, and are defined in U.S. Pat. No. 7,279,704 at cols. 31-32, which are incorporated herein by reference.

2-phenylbenzimidazole (herein called "phenylbenzimidazole") and phenylpyridine-containing materials are provided, which can be used in phosphorescent organic light emitting devices giving high efficiency, high stability, long operational lifetimes, and improved color. The materials may be used as phosphorescent emissive dopants in green devices.

Phenylpyridine and phenylbenzimidazole-containing heteroleptic compounds are provided. Heteroleptic compounds provide highly tunable phosphorescent emitting materials and thus these compounds are desirable in order to achieve a broad range of colors and highly saturated colors. The emission of the metal complex can be tuned by carefully choosing different ligands, depending on the triplet energy and HOMO/LUMO levels of different ligands. While phenylbenzimidazoles provide devices with good lifetime performance, they generally have a higher sublimation temperature and may have a vibronic emission spectrum (see FIG. 3). A heteroleptic complex containing both a phenylbenzimidazole ligand and phenylpyridine ligand may provide a lower sublimation temperature while maintaining the beneficial properties of the phenylbenzimidazole (i.e., long lifetime and high stability).

It is generally accepted that the sublimation temperature of a complex can be determined from the molecular structure of the complex. High molecular weight usually results in higher sublimation temperature. So then, a heteroleptic compound may be expected to have a sublimation temperature between that of the corresponding homoleptic compounds because the molecular weight of the heteroleptic compound is between the molecular weights of each of the corresponding homoleptic compounds. However, some of the heteroleptic compounds containing phenylpyridine and phenylbenzimidazole, as disclosed herein, have a sublimation temperature that is lower than both corresponding homoleptic compounds (i.e., phenylpyridine homoleptic compound and phenylbenzimidazole homoleptic compound). The reduction in the sublimation temperature of the heteroleptic complex may provide improved device manufacturing.

In addition, these heteroleptic compounds may also provide a more narrow emission spectrum. Without being bound by theory, it is noted that both ligands (i.e., phenylpyridine and phenylbenzimidazole) are green emitters that are close in energy level, thus both ligands could directly contribute to the emission of the compound. The observed emission spectra of the heteroleptic compounds disclosed herein are unexpectedly narrow (see FIG. 3). The emission spectrum of the compound is expected to be similar to phenylbenzimidazole emission because the electrochemical gap of benzimidazole is smaller than phenylpyridine (i.e., benzimidazole has a shallower HOMO and a deeper LUMO than phenylpyridine). However, the observed emission of the heteroleptic compound is closer to the emission profile of phenylpyridine than benzimidazole (e.g, no vibronic structure). It is believed that the observed emission spectra of the compounds may be a result of unexpected interactions between the phenylpyridine and phenylbenzimidazole ligands when both ligands are included in the same complex. Therefore, a complex containing phenylpyridine and phenylbenzimidazole ligands may be advantageously used as an emissive material for PHOLEDs having long lifetimes, high stability, and improved manufacturing as well as improved color.

Heteroleptic compounds $Ir(L1)_n(L2)_{3-n}$ are provided, which may be advantageously used in OLEDs, having the formula:

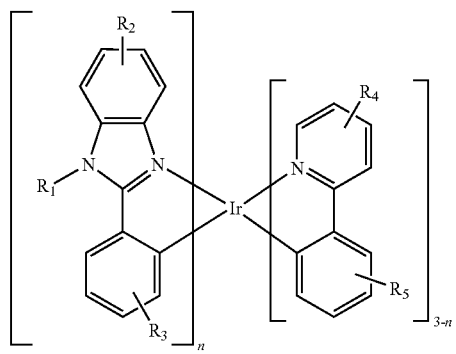

where n=1 or 2, where

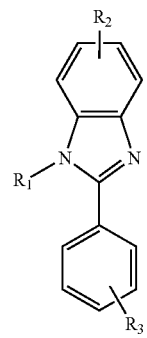

is L1 and

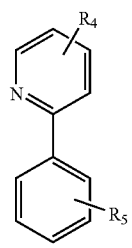

is L2. Each of $R_1$, $R_2$, $R_3$, $R_4$, and $R_5$ may represent mono, di, tri, or tetra substitutions. Each of $R_1$, $R_2$, $R_3$, $R_4$, and $R_5$ are independently selected from the group consisting of hydrogen, alkyl, heteroalkyl, aryl, substituted aryl, heteroaryl, and substituted heteroaryl. Preferably, n is 1.

In one aspect, the compound has the formula:

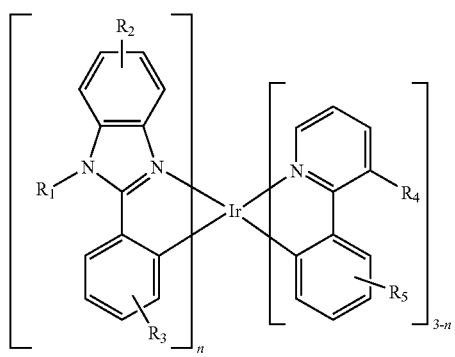

where $R_4$ is hydrogen or methyl.

In another aspect, $R_1$ is selected from the group consisting of alkyl, heteroalkyl, aryl, heteroaryl, substituted aryl, and substituted heteroaryl, and where $R_1$ does not form a conjugated system with L1. The phenylbenzimidazole moiety is important in order to achieve the beneficial properties of these heteroleptic compounds. Therefore, in order to maintain the beneficial features, the $R_1$ substituent is a chemical group having minimal conjugation. Further, conjugation between the phenyl and the benzimidazole portions of L1 will likely result in a reduced LUMO level and a loss of the saturated green emission. Thus, the substituents (e.g., $R_1$ and $R_2$) are not fused as to form an extended conjugated system.

Preferably, the $R_1$ substituent is a branched alkyl or a twisted aryl (e.g., isopropyl and isobutyl). "Twisted aryl" as used herein refers to a structure having the formula

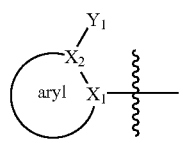

where $X_1$ and $X_2$ are independently selected from C and N, $Y_1$ is not hydrogen, and $Y_1$ may be joined to other substituents on the aryl ring. Branched alkyl and twisted aryl substituents may provide reduced solid state packing and a lower sublimation temperature.

More preferably, $R_1$ is

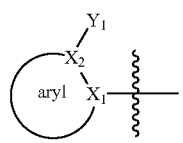

where $X_1$ and $X_2$ are independently selected from C and N. $Y_1$ is not hydrogen. $Y_1$ may be joined to other substituents on the aryl ring. It is thought that a non-planar conformation contributes to the beneficial properties of the compound. For example, a heteroleptic compound having this $R_1$ substituent may have better color and a lower sublimation temperature. In addition, this $R_1$ substituent may be less likely to lower the triplet energy of the compound.

In another aspect, each of $R_2$, $R_3$, and $R_5$ are hydrogen.

Specific examples of heteroleptic compounds include compounds containing L1 selected from the group consisting of:

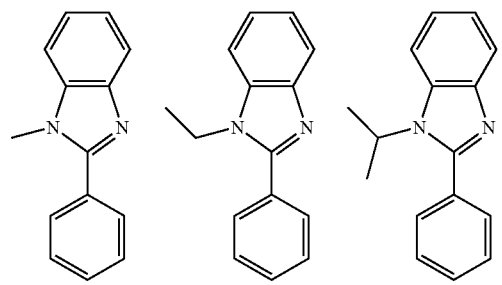

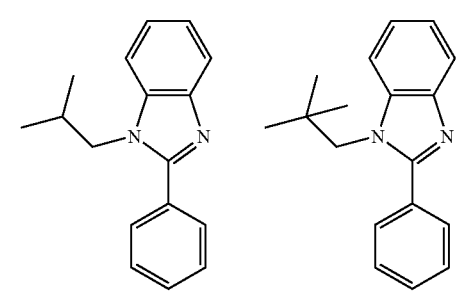

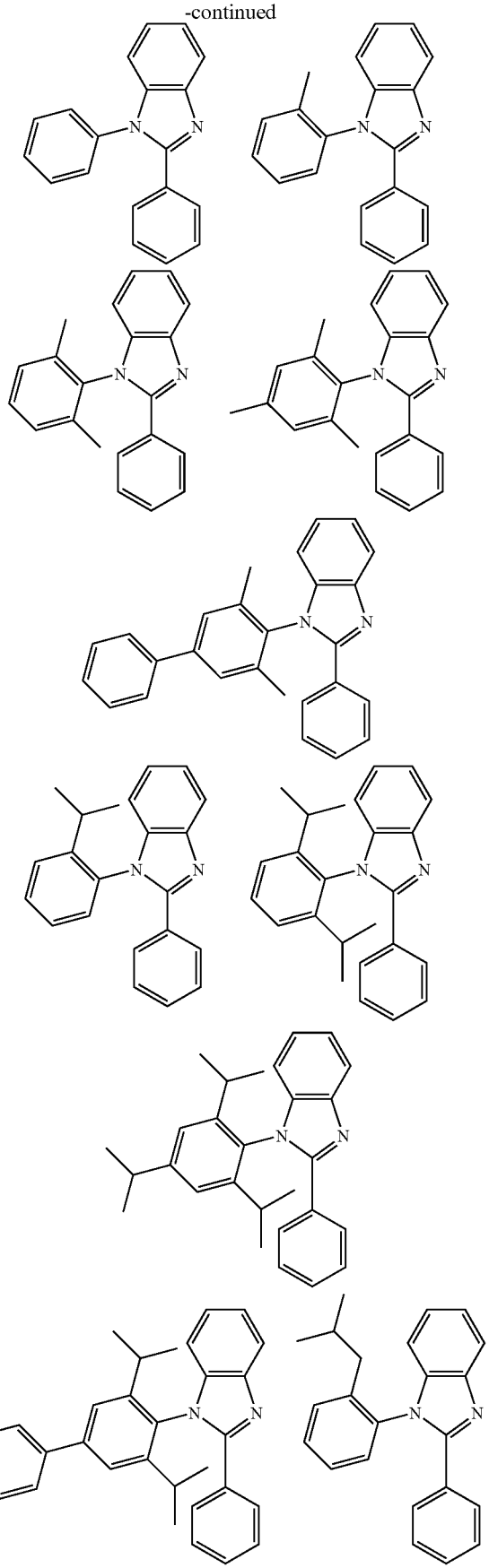

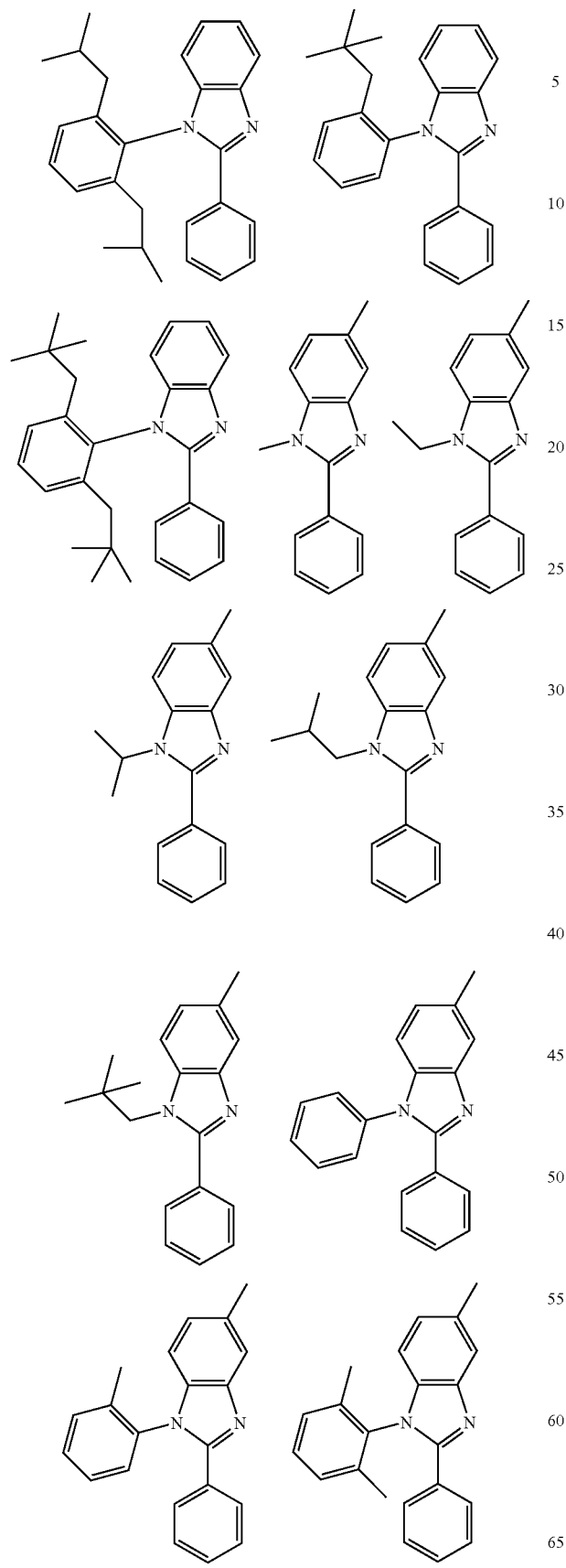
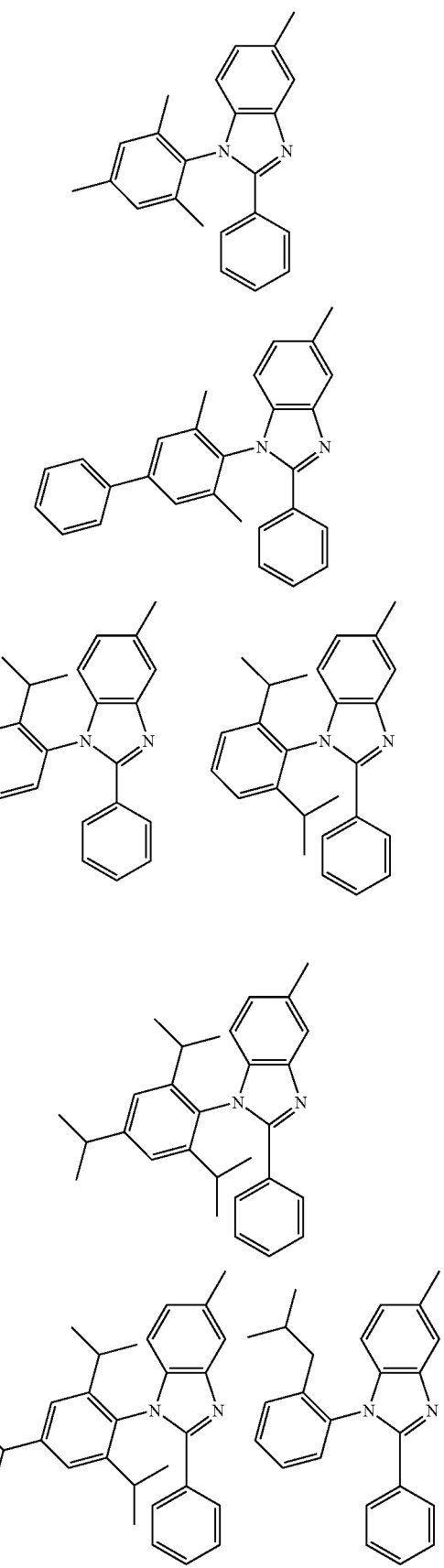

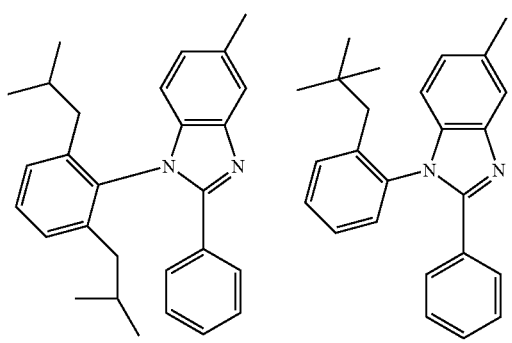
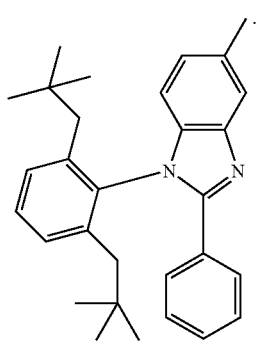
Further specific examples of heteroleptic compounds include compounds containing L2 selected from the group consisting of:
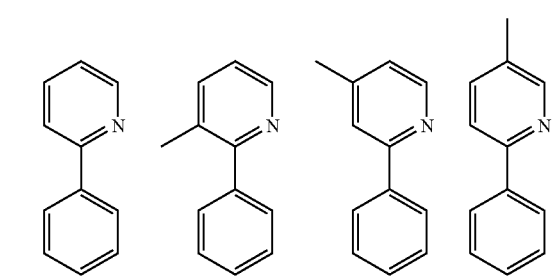
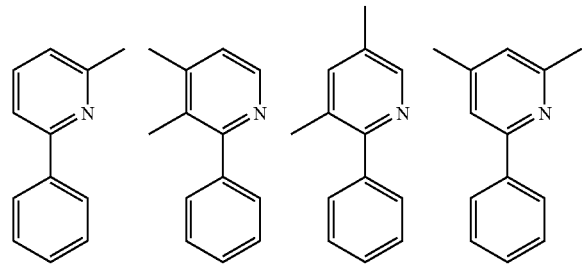
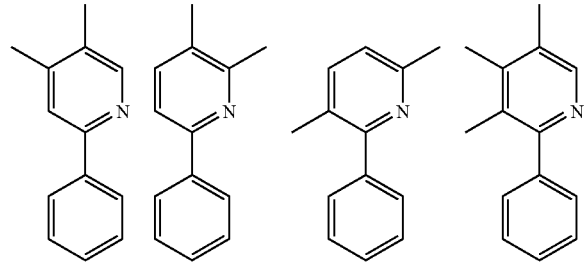
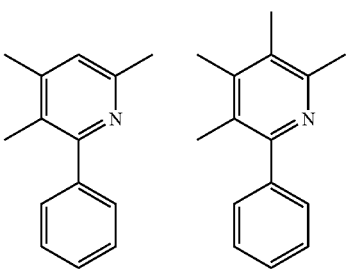
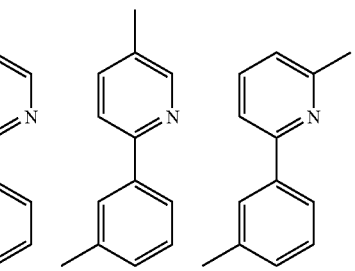
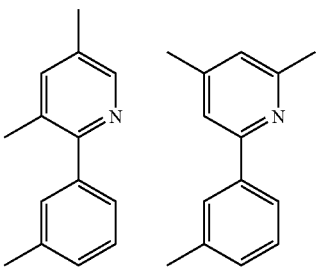
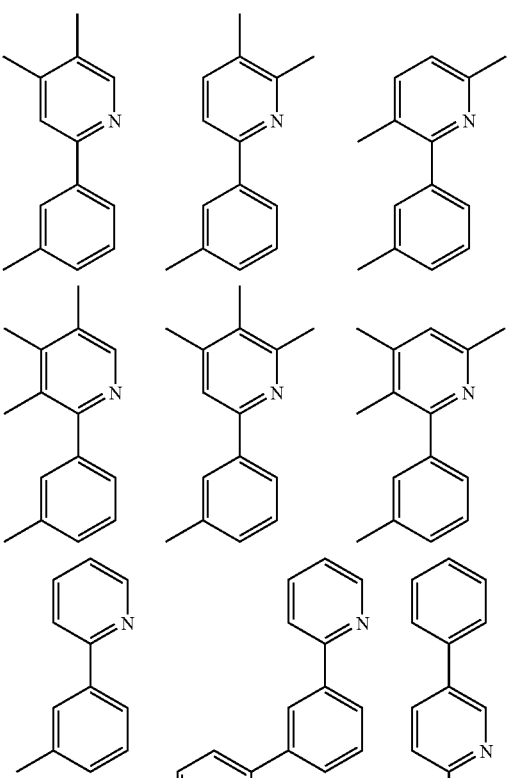
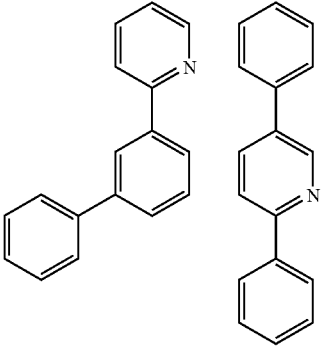

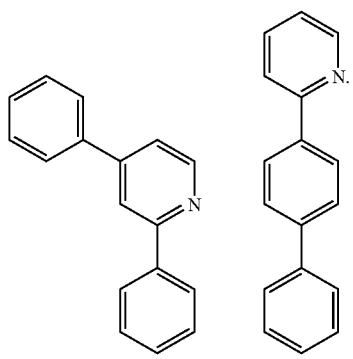
In one aspect, the heteroleptic compound includes both an L1 and an L2 selected from the groups provided above.
Further examples of specific heteroleptic compounds include compounds containing L1 selected from the group consisting of:
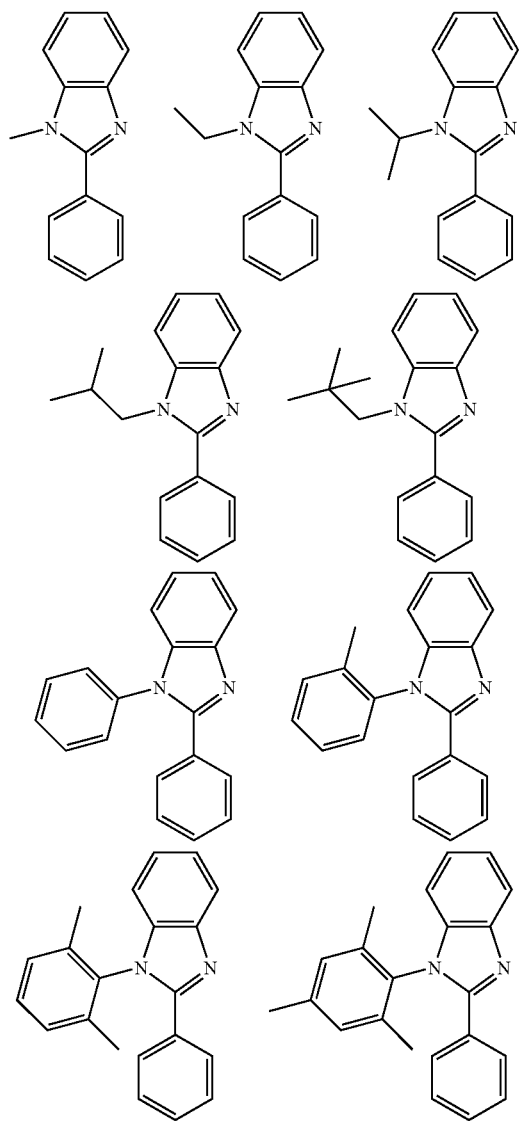
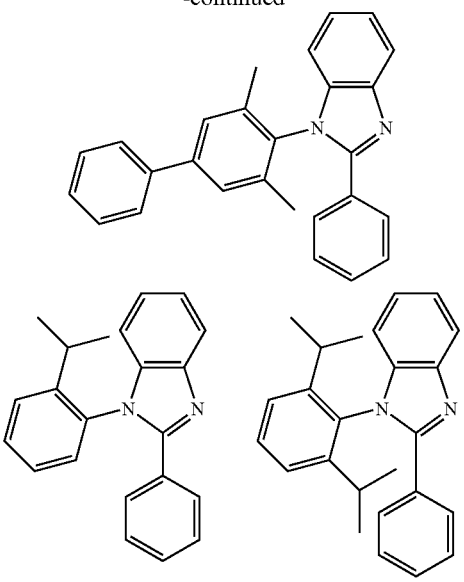
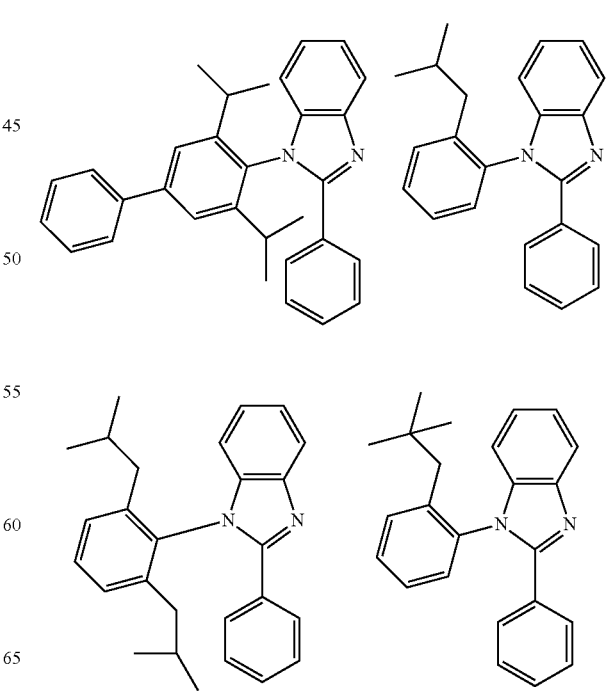

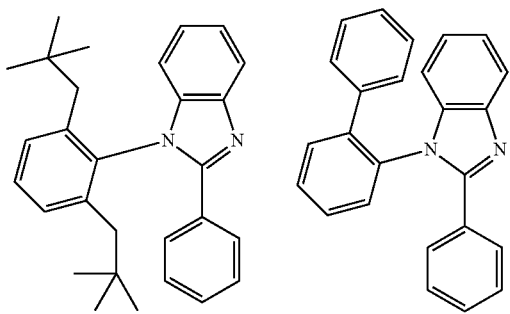
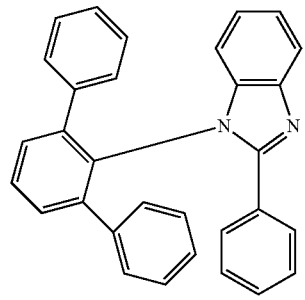
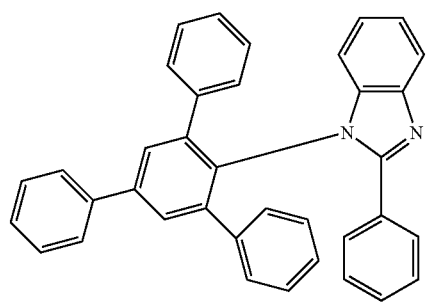
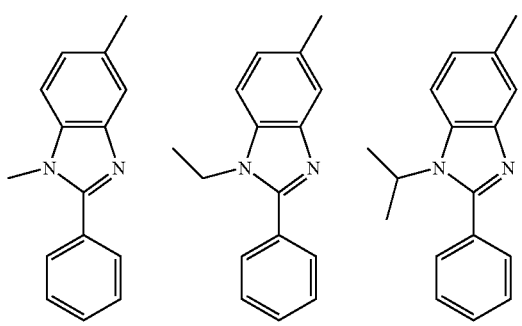
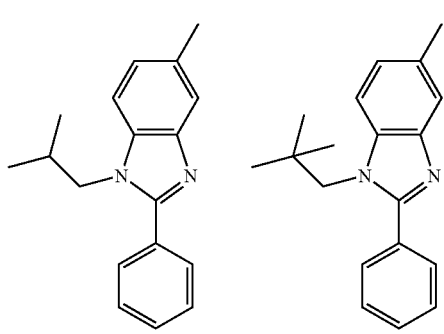
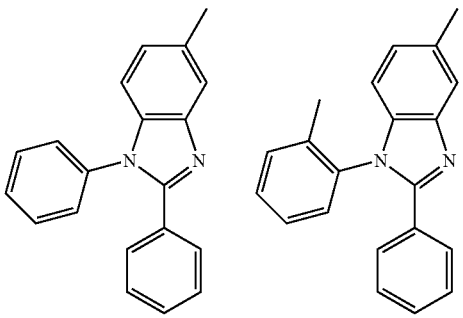
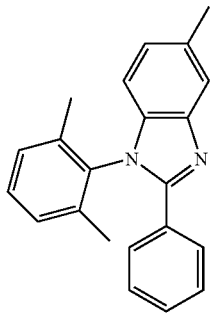
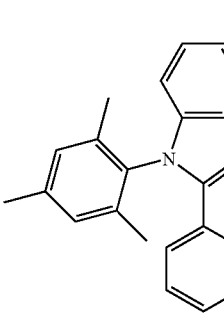
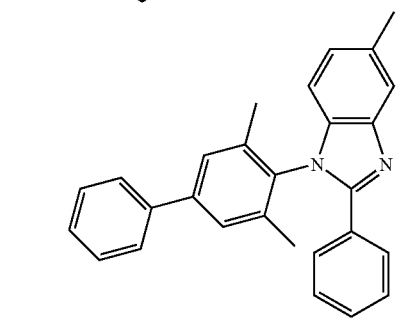
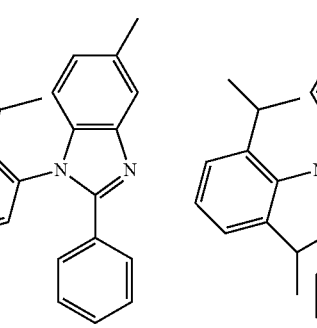
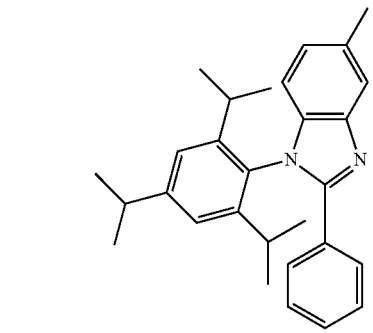

-continued
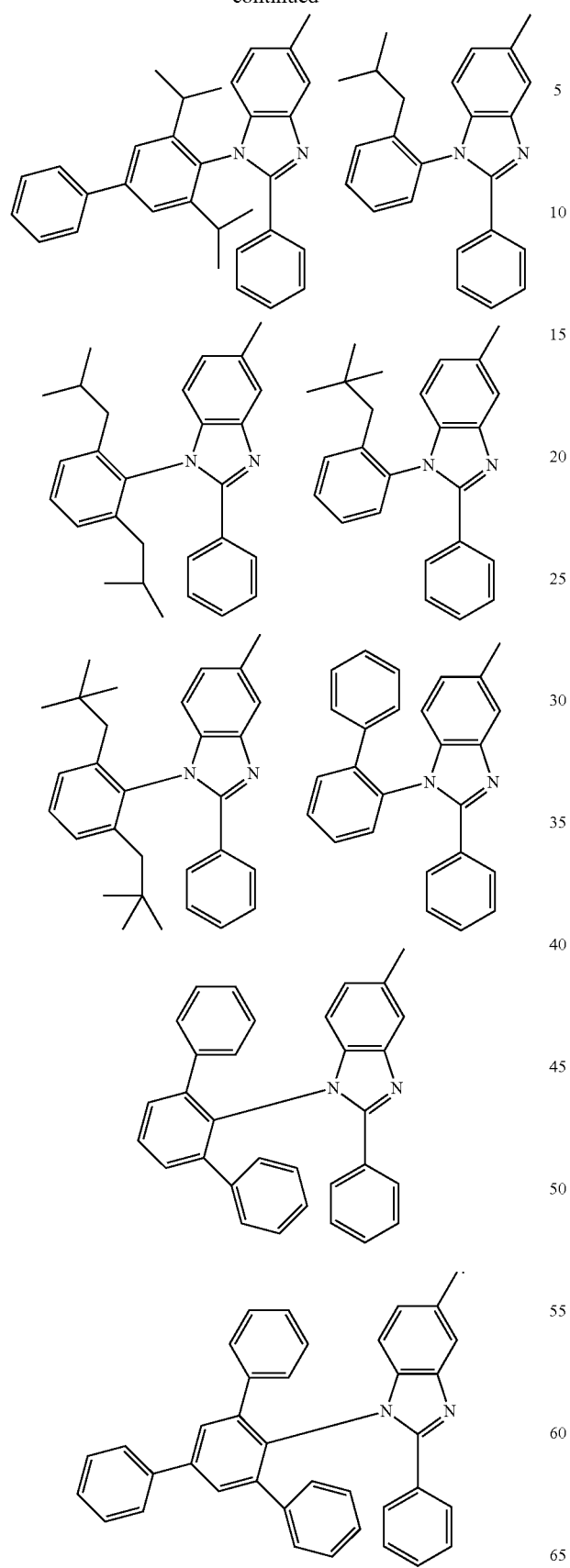
Additional specific examples of heteroleptic compounds include compounds containing L2 selected from the group consisting of:
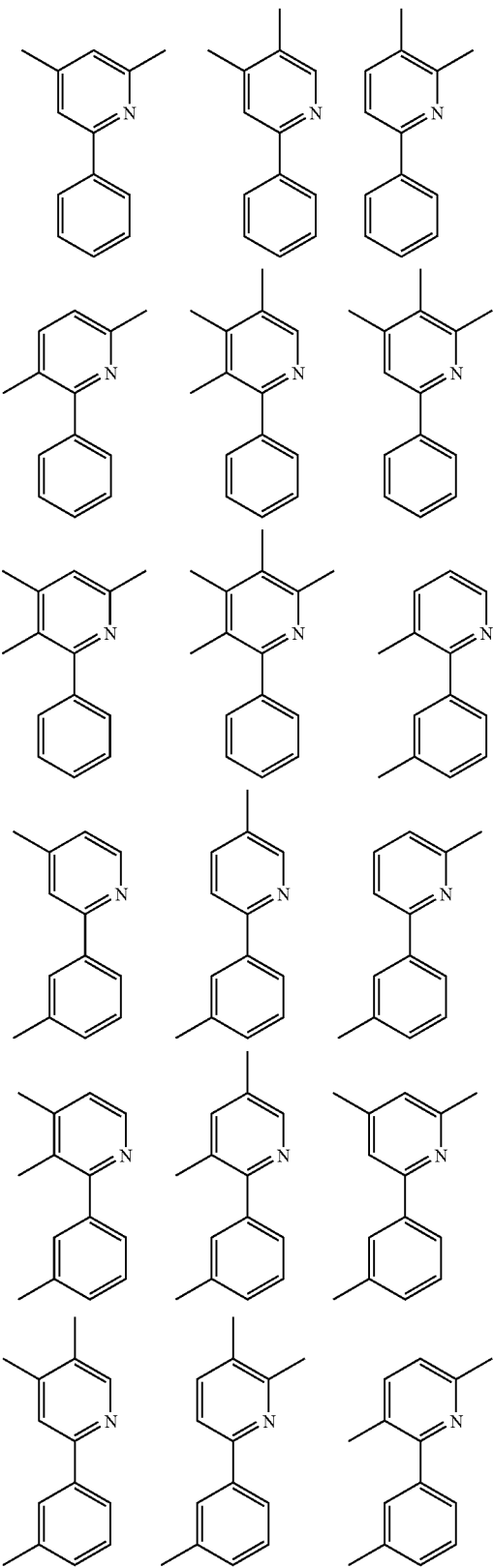

-continued
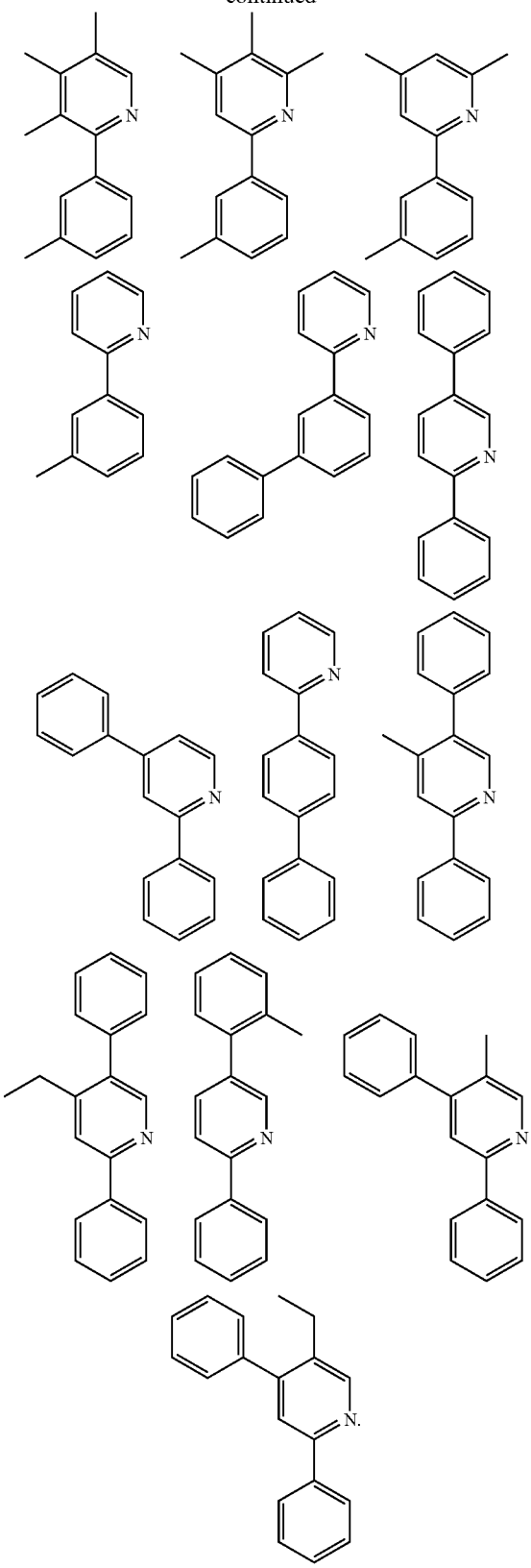
In another aspect, the heteroleptic compound includes both an L1 and an L2 from the two immediately proceeding groups.
Preferably, the heteroleptic compound is selected form the group consisting of:
Compound 1
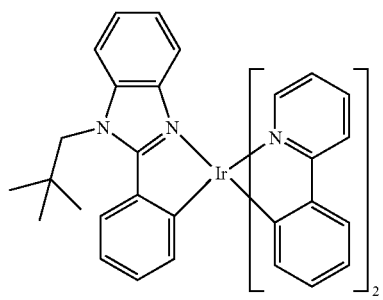
Compound 2
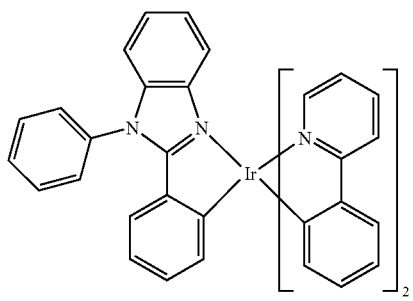
Compound 3
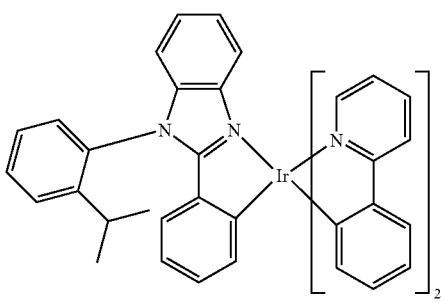
Compound 4
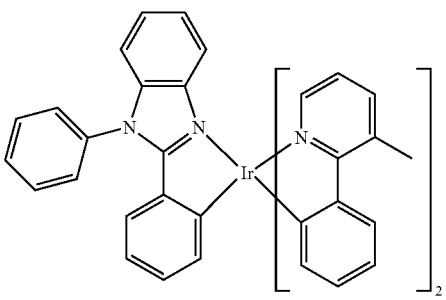
Compound 5
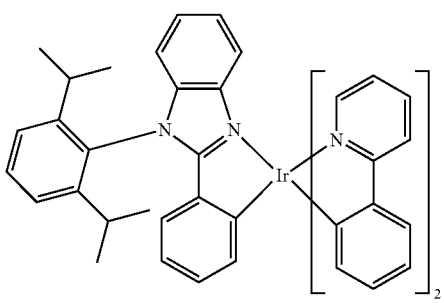

Compound 6
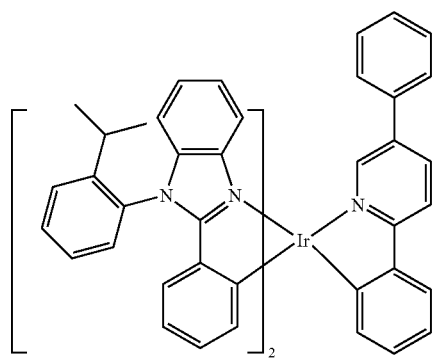
Compound 7
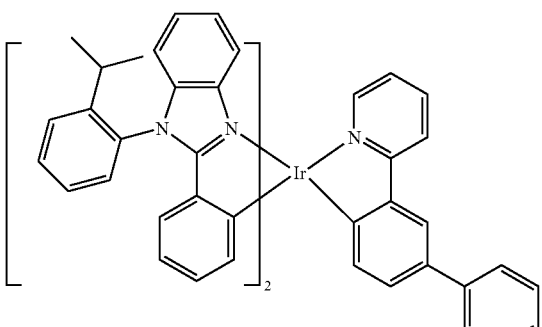
Compound 8
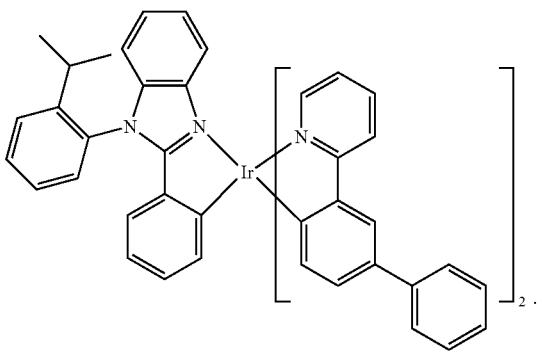
More preferably, the heteroleptic compound is selected from Compounds 1, 3, 5-8.
In another aspect, preferably the heteroleptic compound is selected form the group consisting of:
Compound 1
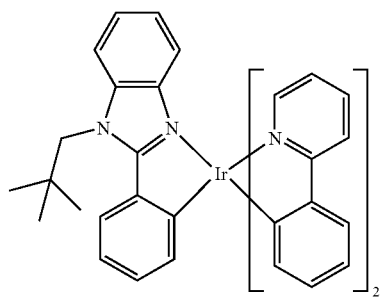
Compound 2
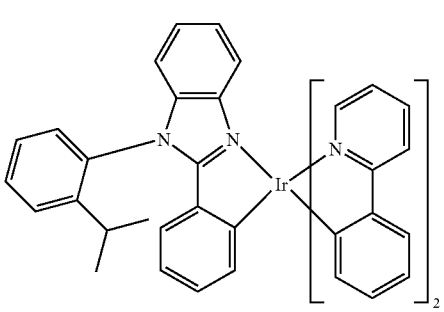
Compound 3
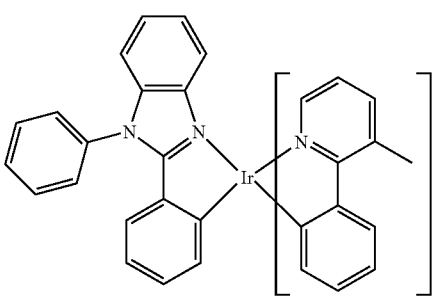
Compound 4
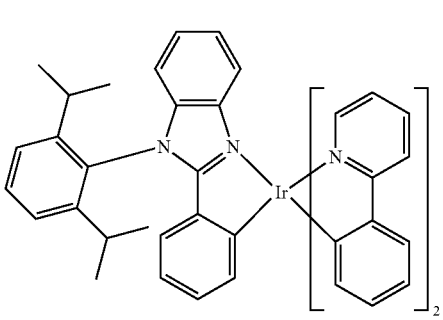
Compound 5
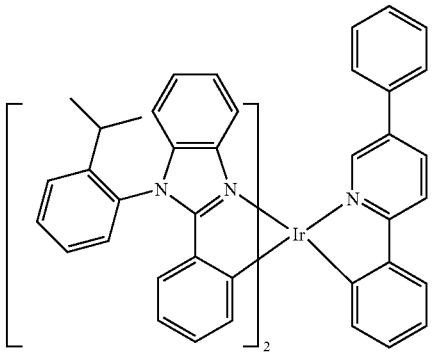
Compound 6
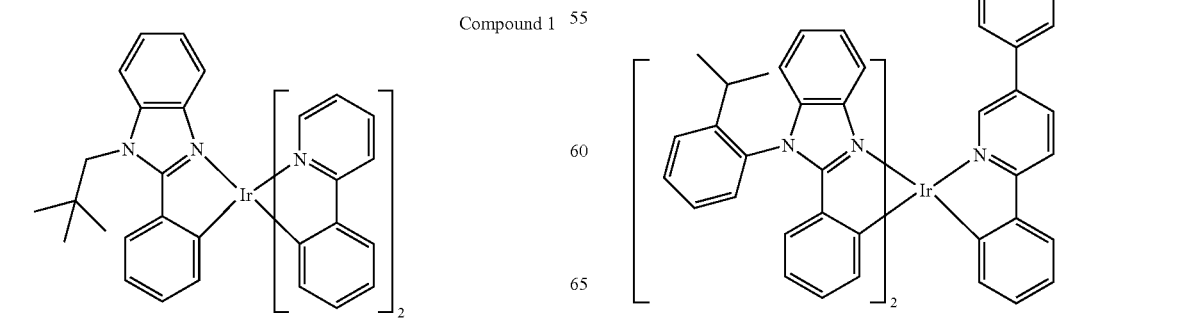

-continued

Compound 7

Compound 8

Compound 9

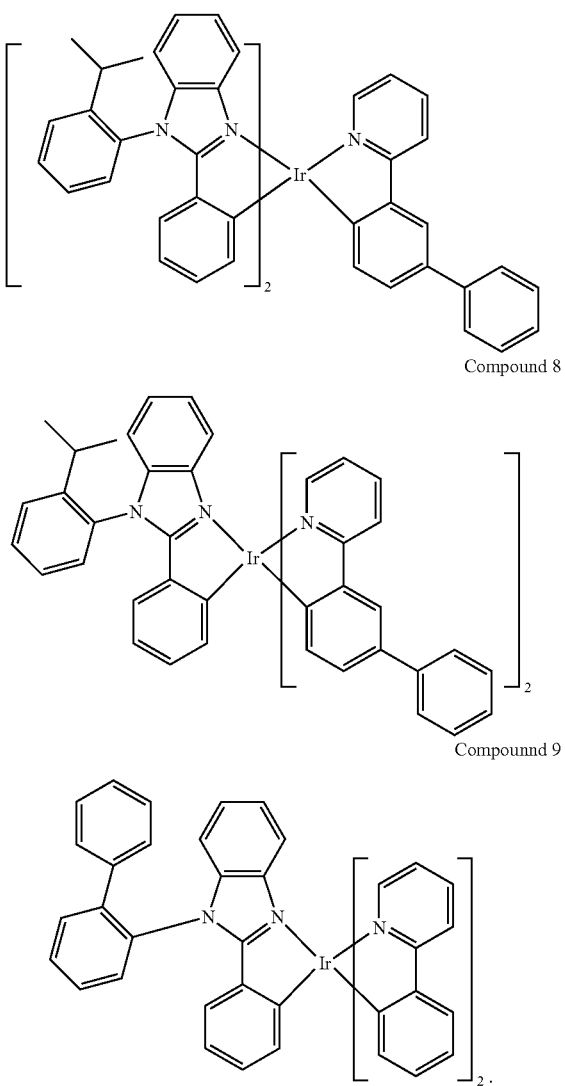

In one aspect, the heteroleptic compound has an emission spectrum with a narrower full width at half maximum (FWHM) than either

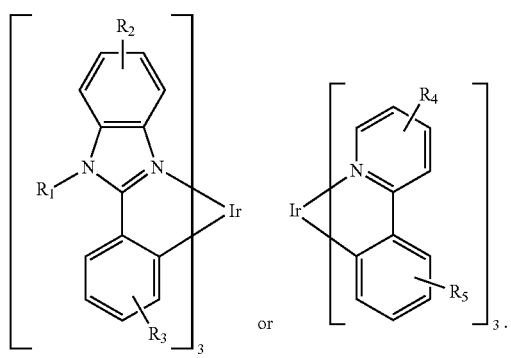

In another aspect, the heteroleptic compound may have a lower sublimation temperature than either

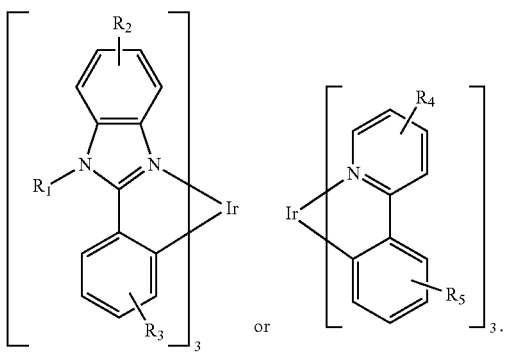

Additionally, an organic light emitting device is also provided. The device comprises an anode, a cathode, and an organic layer, disposed between the anode and the cathode. The organic layer further comprises a heteroleptic compound $Ir(L1)_n(L2)_{3-n}$, as described above. Preferably, the organic layer contains a heteroleptic compound selected from the group consisting of Compound 1-Compound 8. More preferably, the organic layer contains a heteroleptic compound selected from the group consisting of Compounds 1, 3, and 5-8.

Further, an organic light emitting device comprising an anode, a cathode, and an organic layer that is disposed between the anode and the cathode, itself further comprising a heteroleptic compound selected from the group consisting of Compound 1-Compound 9 is also provided.

The organic layer of the device may comprise a heteroleptic compound wherein $R_1$ is selected from the group consisting of alkyl, heteroalkyl, aryl, heteroaryl, substituted aryl, and substituted heteroaryl, and where $R_1$ does not form a conjugated system with L1. Preferably, R1 is $R_1$ is

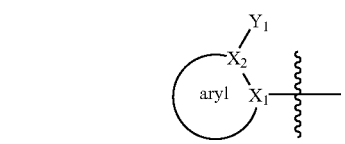

where $X_1$ and $X_2$ are independently selected from C and N. $Y_1$ is not hydrogen. $Y_1$ may be joined to other substituents on the aryl ring.

In one aspect, the emissive layer further comprises a host. Preferably, the host has the formula:

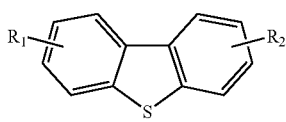

where $R_1$ and $R_2$ represent, independently, mono, di, tri or tetra substitutions selected from alkyl, alkoxy, amino, alkenyl, alkynyl, arylkyl, aryl and heteroaryl, or no substitution; and where at least one of $R_1$ and $R_2$ includes a triphenylene group.

In another aspect, the host has the formula:

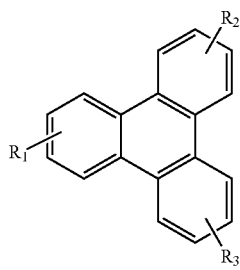

where each of $R_1$, $R_2$, and $R_3$ is independently a hydrogen, a non-fused aryl group, or a non-fused heteroaryl group having one or more meta-substituents, wherein at least one of $R_1$, $R_2$, and $R_3$ is not hydrogen. Each meta-substituent is a non-fused aryl or heteroaryl group optionally substituted with further substituents selected from the group consisting of non-fused aryl groups, non-fused heteroaryl groups, and alkyl groups.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

A consumer product comprising a device is also provided, wherein the device further comprises an anode, a cathode and an organic layer. The organic layer further comprises a phenylpyridine and phenylbenzimidazole-containing complex as described.

In particular, a consumer product containing a device, in which the organic layer of the device contains a heteroleptic compound selected from the group consisting of Compounds 1-9, is provided.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| Hole injection materials | | |
| Phthalocyanine and porphryin compounds | | Appl. Phys. Lett. 69, 2160 (1996) |
| Starburst triarylamines | | J. Lumin. 72-74, 985 (1997) |

TABLE 1-continued
| MATERIAL | EXAMPLES OF MATERIAL | PUBLICATIONS |
|---|---|---|
| $CF_x$ Fluorohydrocarbon polymer | 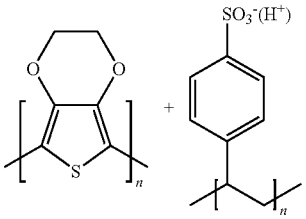 | Appl. Phys. Lett. 78, 673 (2001) |
| Conducting polymers (e.g., PEDOT:PSS, polyaniline, polythiophene) | 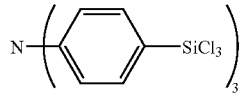 | Synth. Met. 87, 171 (1997) WO2007002683 |
| Phosphonic acid and silane SAMs | 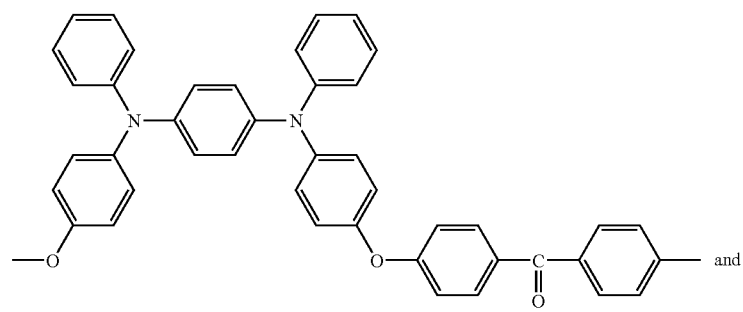 | US20030162053 |
| Triarylamine or polythiophene polymers with conductivity dopants | 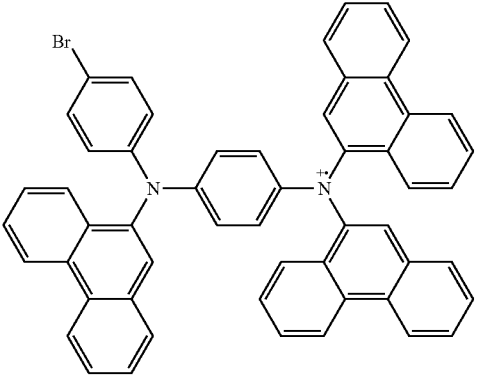 [SMILES: Brc1ccc(N(c2ccc(N(c3cc4ccccc4c4ccccc34)c3cc4ccccc4c4ccccc34)cc2)c2cc3ccccc3c3ccccc23)cc1] and 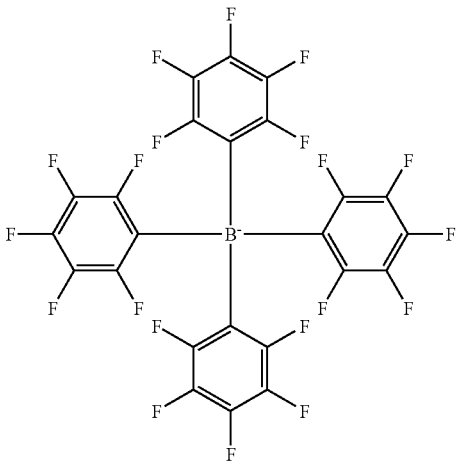 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EA01725079A1 |

TABLE 1-continued
| MATERIAL | EXAMPLES OF MATERIAL | PUBLICATIONS |
|---|---|---|
| Arylamines complexed with metal oxides such as molybdenum and tungsten oxides | 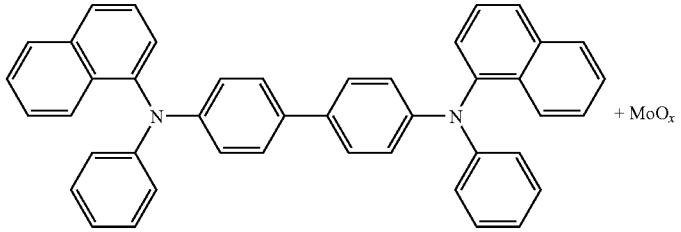 [SMILES: c1ccc(N(c2ccc(-c3ccc(N(c4ccccc4)c4cccc5ccccc45)cc3)cc2)c2cccc3ccccc23)cc1] | SID Symposium Digest, 37, 923 (2006) WO2009018009 |
| p-type semiconducting organic complexes | 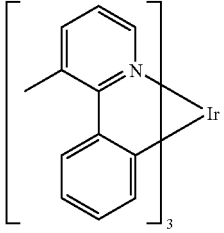 | US20020158242 |
| Metal organometallic complexes | 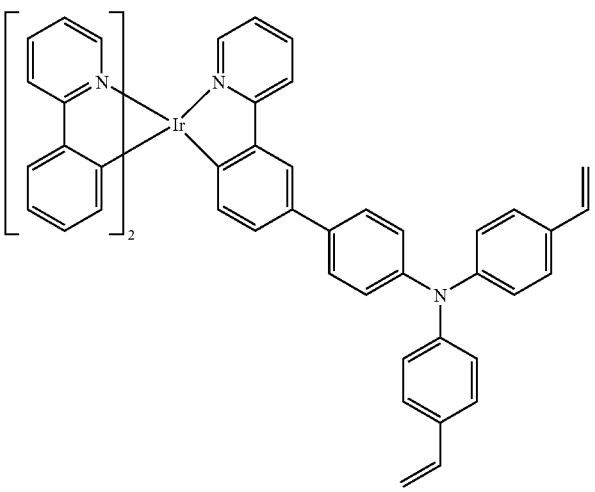 | US20060240279 |
| Cross-linkable compounds | 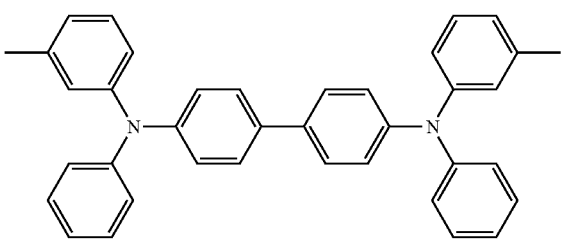 | US20080220265 |
Hole transporting materials
| Triarylamines (e.g., TPD, α-NPD) | | Appl. Phys. Lett. 51, 913 (1987) |
|---|---|---|

TABLE 1-continued

| MATERIAL | EXAMPLES OF MATERIAL | PUBLICATIONS |
|---|---|---|
| | | U.S. Pat. No. 5,061,569 |
| | | EP650955 |
| | | J. Mater. Chem. 3, 319 (1993) |

TABLE 1-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

TABLE 1-continued
| MATERIAL | EXAMPLES OF MATERIAL | PUBLICATIONS |
| --- | --- | --- |
| Triarylamine with (di)benzothiophene/(di)benzofuran | 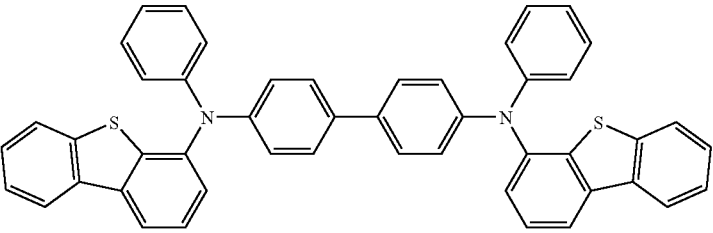 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |
| Indolocarbazoles | 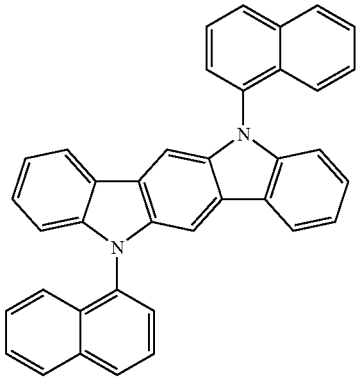 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 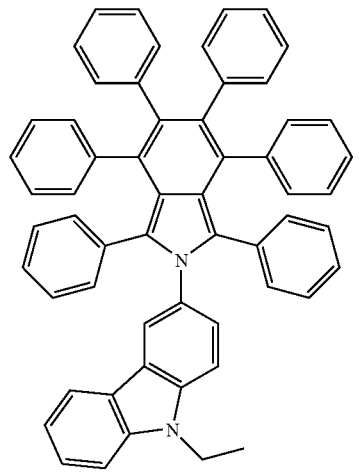 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 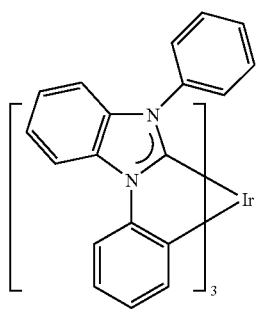 | US20080018221 |

TABLE 1-continued

| MATERIAL | EXAMPLES OF MATERIAL | PUBLICATIONS |
|---|---|---|
| Phosphorescent OLED host materials<br>Red hosts | | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |

TABLE 1-continued
| MATERIAL | EXAMPLES OF MATERIAL | PUBLICATIONS |
| --- | --- | --- |
| Conjugated oligomers and polymers (e.g., polyfluorene) | 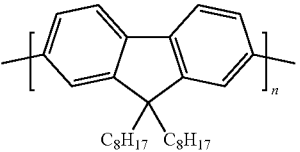 | Org. Electron. 1, 15 (2000) |
| Aromatic fused rings | 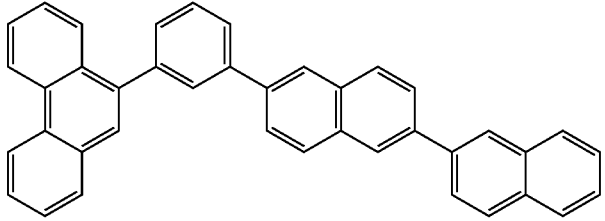 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 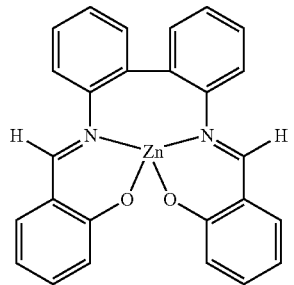 | WO2009062578 |
| Green hosts | | |
| Arylcarbazoles | 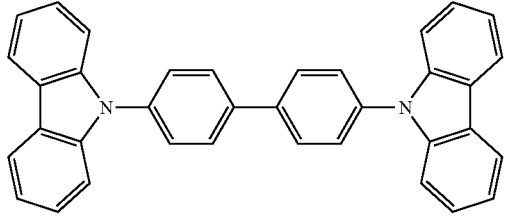 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 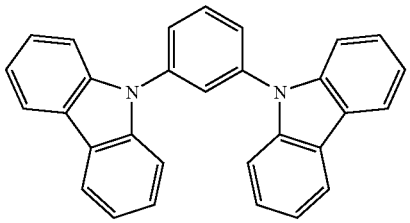 [SMILES: c1cc(-n2c3ccccc3c3ccccc32)cc(-n2c3ccccc3c3ccccc32)c1] | US20030175553 |
| | 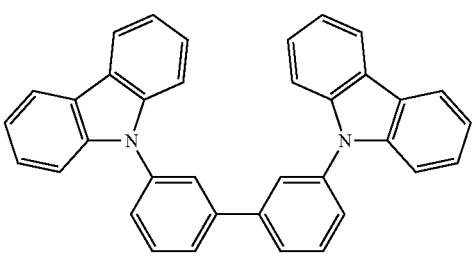 [SMILES: c1cc(-c2cccc(-n3c4ccccc4c4ccccc43)c2)cc(-n2c3ccccc3c3ccccc32)c1] | WO2001039234 |

TABLE 1-continued

| MATERIAL | EXAMPLES OF MATERIAL | PUBLICATIONS |
| --- | --- | --- |
| Aryltriphenylene compounds | | US20060280965 |
| | | US20060280965 |
| | | WO2009021126 |
| Donor acceptor type molecules | | WO2008056746 |

TABLE 1-continued

| MATERIAL | EXAMPLES OF MATERIAL | PUBLICATIONS |
| --- | --- | --- |
| Aza-carbazole/DBT/DBF | | JP2008074939 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |
| | | WO2006132173 |

TABLE 1-continued

| MATERIAL | EXAMPLES OF MATERIAL | PUBLICATIONS |
|---|---|---|
| | | JP200511610 |
| Spirofluorene-carbazole compounds | | JP2007254297 |
| | | JP2007254297 |
| Indolocabazoles | | WO2007063796 |
| | | WO2007063754 |

TABLE 1-continued

| MATERIAL | EXAMPLES OF MATERIAL | PUBLICATIONS |
| --- | --- | --- |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |
| Metal phenoxypyridine compounds | | WO2005030900 |
| Metal coordination complexes (e.g., Zn, Al with N^N ligands) | | US20040137268, US20040137267 |

TABLE 1-continued
| MATERIAL | EXAMPLES OF MATERIAL | PUBLICATIONS |
|---|---|---|
| Blue Hosts | | |
| Arylcarbazoles | 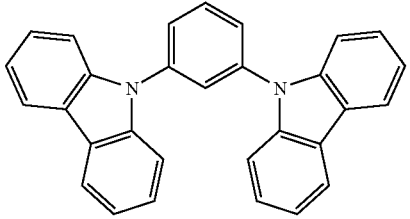 [SMILES: c1cc(-n2c3ccccc3c3ccccc32)cc(-n2c3ccccc3c3ccccc32)c1] | Appl. Phys. Lett, 82, 2422 (2003) |
| | 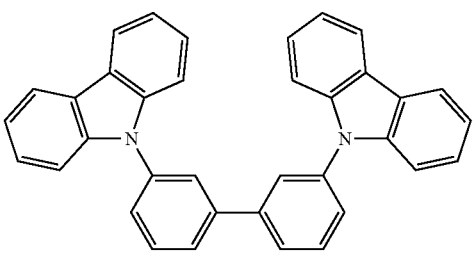 [SMILES: c1cc(-c2cccc(-n3c4ccccc4c4ccccc43)c2)cc(-n2c3ccccc3c3ccccc32)c1] | US20070190359 |
| Dibenzothiophene/Dibenzofuran-carbazole compounds | 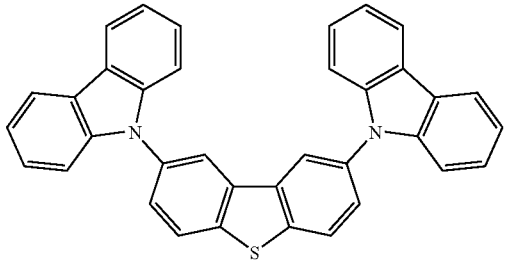 [SMILES: c1ccc2c(c1)c1ccccc1n2-c1ccc2sc3ccc(-n4c5ccccc5c5ccccc54)cc3c2c1] | WO2006114966, US20090167162 |
| | 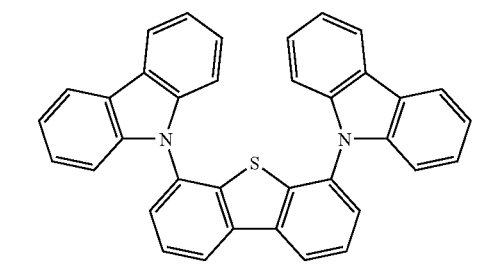 [SMILES: c1cc(-n2c3ccccc3c3ccccc32)c2sc3c(-n4c5ccccc5c5ccccc54)cccc3c2c1] | US20090167162 |
| | 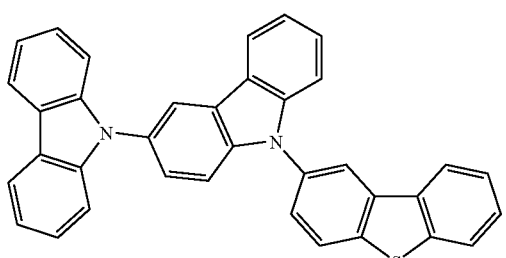 | WO2009086028 |
| | 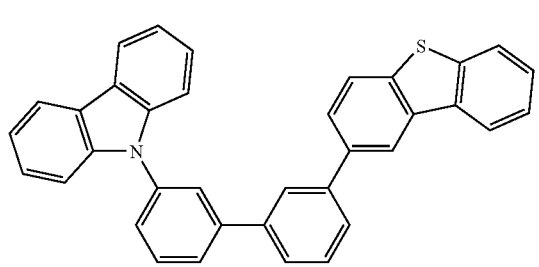 [SMILES: c1cc(-c2cccc(-n3c4ccccc4c4ccccc43)c2)cc(-c2ccc3sc4ccccc4c3c2)c1] | US20090030202, US20090017330 |

TABLE 1-continued
| MATERIAL | EXAMPLES OF MATERIAL | PUBLICATIONS |
|---|---|---|
| Silicon aryl compounds | 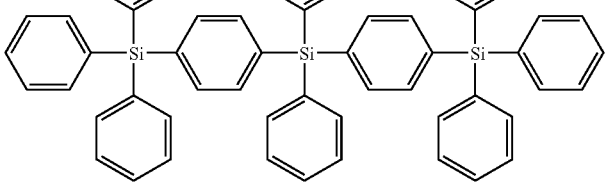 | US20050238919 |
| | 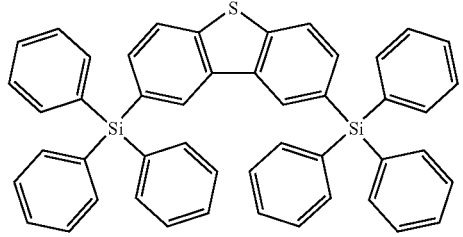 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 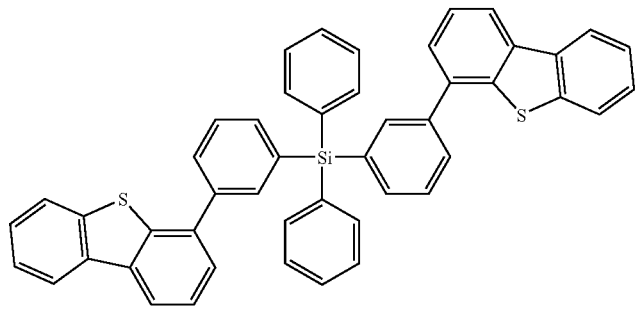 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 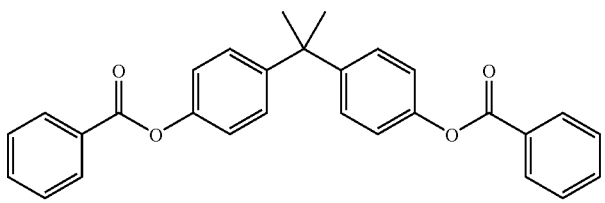 [SMILES: CC(C)(c1ccc(OC(=O)c2ccccc2)cc1)c1ccc(OC(=O)c2ccccc2)cc1] | WO2006100298 |
| High triplet metal organometallic complex | 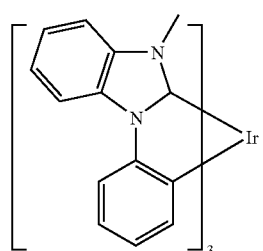 | U.S. Pat. No. 7,154,114 |

TABLE 1-continued

| MATERIAL | EXAMPLES OF MATERIAL | PUBLICATIONS |
|---|---|---|
| Phosphorescent dopants  Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 1-continued

| MATERIAL | EXAMPLES OF MATERIAL | PUBLICATIONS |
|---|---|---|
| | | US20060202194 |
| | | US20070087321 |
| | | US20070087321 |
| | | Adv. Mater. 19, 739 (2007) |
| | | WO2009100991 |

TABLE 1-continued

| MATERIAL | EXAMPLES OF MATERIAL | PUBLICATIONS |
| --- | --- | --- |
|  |  | WO2008101842 |
| Platinum(II) organometallic complexes |  | WO2003040257 |
| Osminum(III) complexes |  | Chem. Mater. 17, 3532 (2005) |
| Ruthenium(II) complexes |  | Adv. Mater. 17, 1059 (2005) |
| Rhenium (I), (II), and (III) complexes |  | US20050244673 |
| Green dopants |  |  |
| Iridium(III) organometallic complexes | and its derivatives | Inorg. Chem. 40, 1704 (2001) |

TABLE 1-continued
| MATERIAL | EXAMPLES OF MATERIAL | PUBLICATIONS |
|---|---|---|
| | 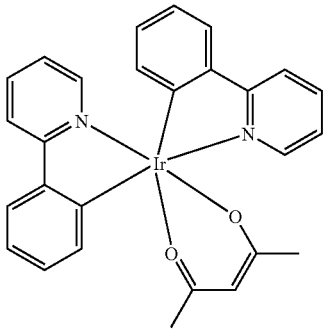 | US20020034656 |
| | 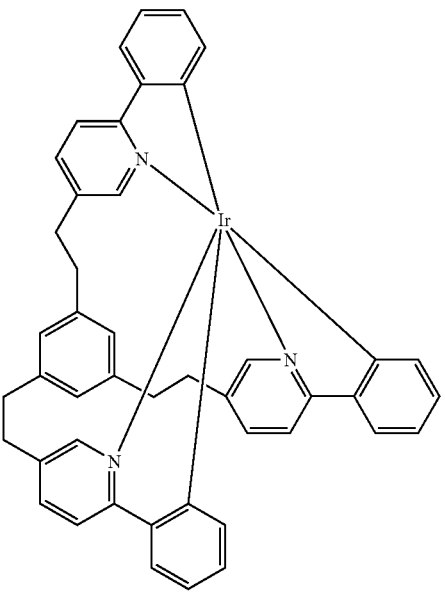 | U.S. Pat. No. 7,332,232 |
| | 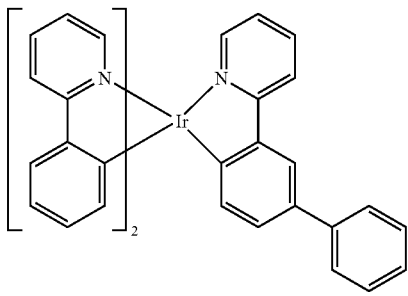 | US20090108737 |
| | 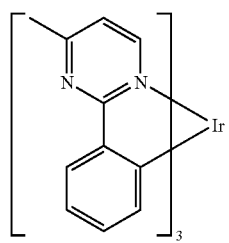 | US20090039776 |

TABLE 1-continued

| MATERIAL | EXAMPLES OF MATERIAL | PUBLICATIONS |
|---|---|---|
| | | U.S. Pat. No. 6,921,915 |
| | | U.S. Pat. No. 6,687,266 |
| | | Chem. Mater. 16, 2480 (2004) |
| | | US20070190359 |
| | | US 20060008670 JP2007123392 |
| | | Adv. Mater. 16, 2003 (2004) |

TABLE 1-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| Monomer for polymeric metal organometallic compounds | | U.S. Pat. No. 7,250,226, U.S. Pat. No. 7,396,598 |

TABLE 1-continued

| MATERIAL | EXAMPLES OF MATERIAL | PUBLICATIONS |
| --- | --- | --- |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |
| | | US20060263635 |

TABLE 1-continued

| MATERIAL | EXAMPLES OF MATERIAL | PUBLICATIONS |
| --- | --- | --- |
| Cu complexes | | WO2009000673 |
| Gold complexes | | Chem. Commun. 2906 (2005) |
| Rhenium(III) complexes | | Inorg. Chem. 42, 1248 (2003) |
| Deuterated organometallic complexes | | US20030138657 |

TABLE 1-continued
| MATERIAL | EXAMPLES OF MATERIAL | PUBLICATIONS |
|---|---|---|
| Organometallic complexes with two or more metal centers | 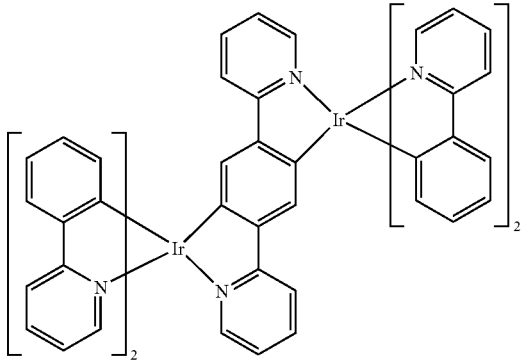 | US20030152802 |
| | 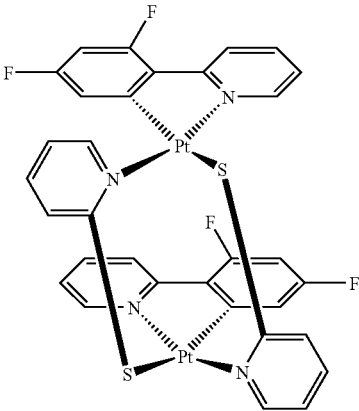 | U.S. Pat. No. 7,090,928 |
| Blue dopants | | |
| Iridium(III) organometallic complexes | 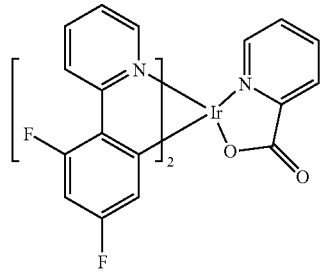 | WO2002002714 |
| | 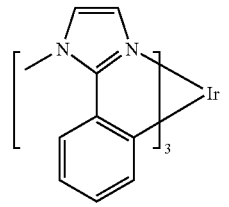 | WO2006009024 |
| | 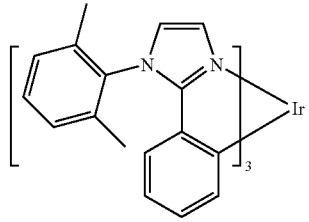 | US20060251923 |

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | U.S. Pat. No. 7,445,855 |
| | | US20070190359, US20080297033 |
| | | U.S. Pat. No. 7,338,722 |
| | | US20020134984 |

TABLE 1-continued
| MATERIAL | EXAMPLES OF MATERIAL | PUBLICATIONS |
|---|---|---|
| | 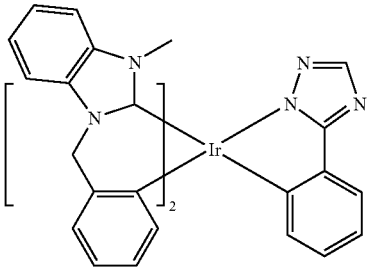 | Angew. Chem. Int. Ed. 47, 1 (2008) |
| | 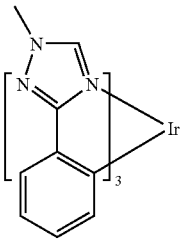 | Chem. Mater. 18, 5119 (2006) |
| | 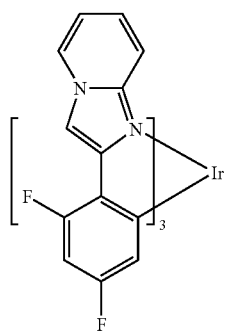 | Inorg. Chem. 46, 4308 (2007) |
| | 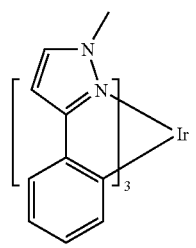 | WO2005123873 |
| | 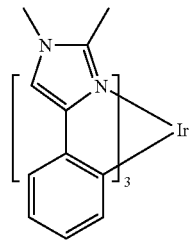 | WO2005123873 |
| | 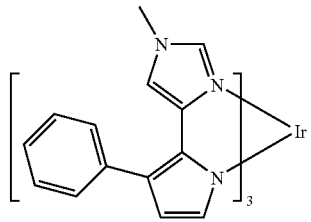 | WO2007004380 |

TABLE 1-continued
| MATERIAL | EXAMPLES OF MATERIAL | PUBLICATIONS |
|---|---|---|
| | 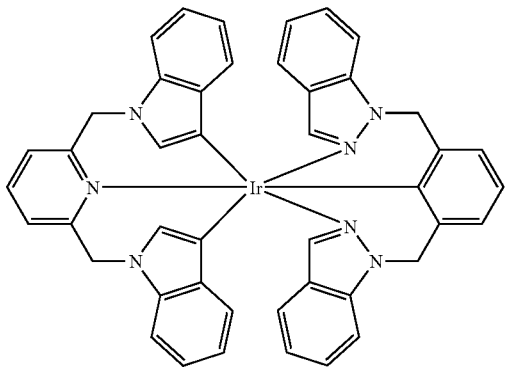 | WO2006082742 |
| Osmium(II) complexes | 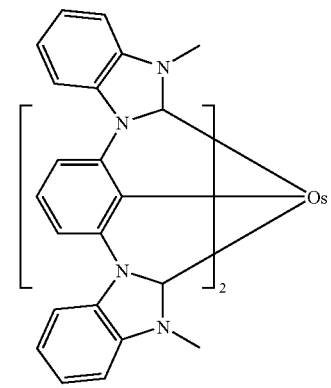 | U.S. Pat. No. 7,279,704 |
| | 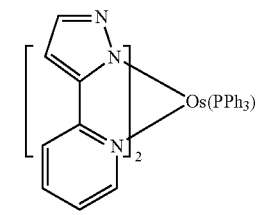 | Organometallics 23, 3745 (2004) |
| Gold complexes | 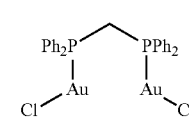 | Appl. Phys. Lett. 74, 1361 (1999) |
| Platinum(II) complexes | 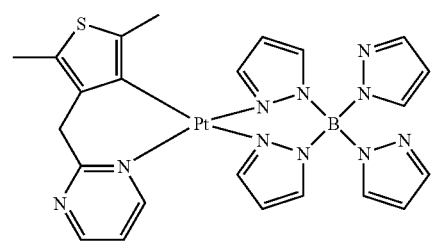 | WO2006098120, WO2006103874 |

TABLE 1-continued

| MATERIAL | EXAMPLES OF MATERIAL | PUBLICATIONS |
| --- | --- | --- |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 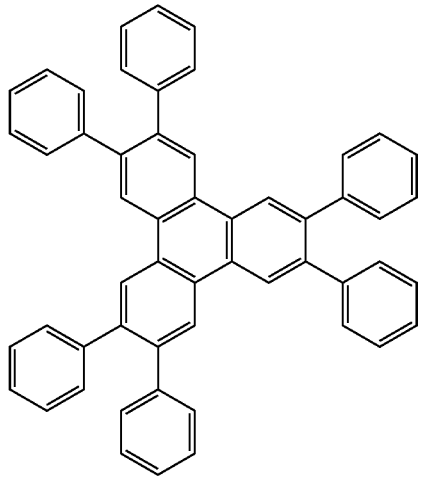 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 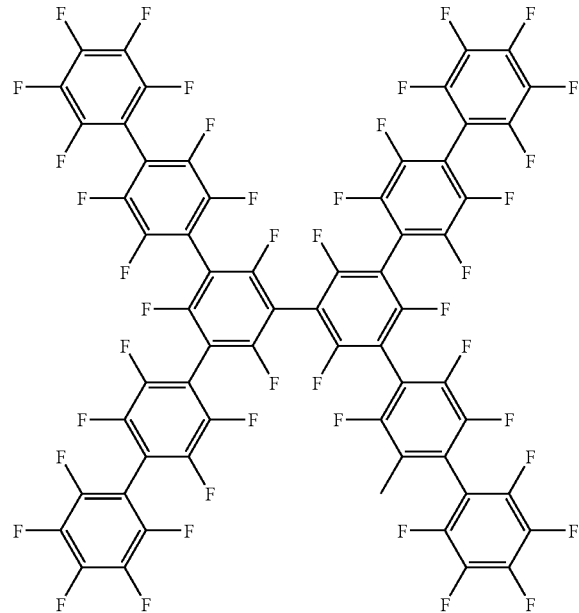 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 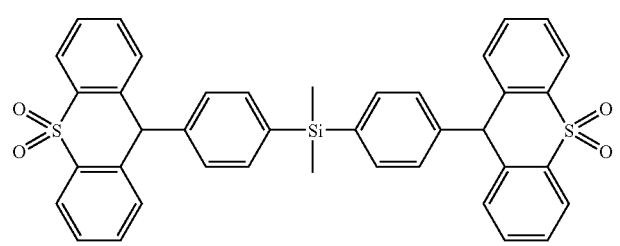 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |

TABLE 1-continued

| MATERIAL | EXAMPLES OF MATERIAL | PUBLICATIONS |
|---|---|---|
| Electron transporting materials | | |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) U.S. Pat. No. 7,230,107 |

TABLE 1-continued

| MATERIAL | EXAMPLES OF MATERIAL | PUBLICATIONS |
|---|---|---|
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 1-continued
| MATERIAL | EXAMPLES OF MATERIAL | PUBLICATIONS |
|---|---|---|
| Silole compounds | 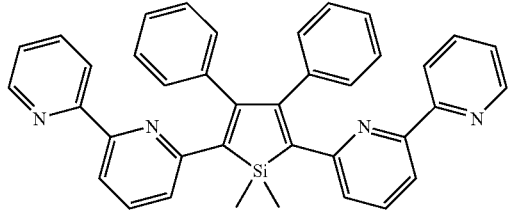 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 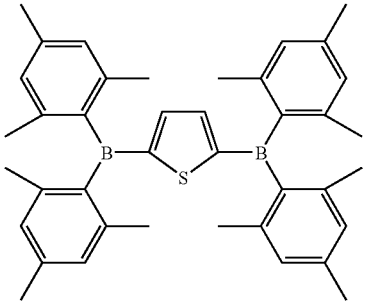 | J. Am. Chem. Soc. 120, 9714 (1998) |
| Fluorinated aromatic compounds | 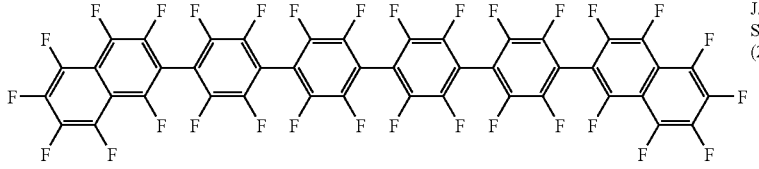 | J. Am. Chem. Soc. 122, 1832 (2000) |
| Fullerene (e.g., C60) | 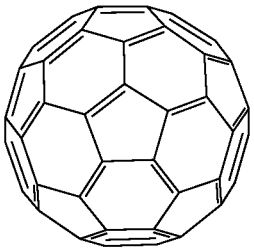 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 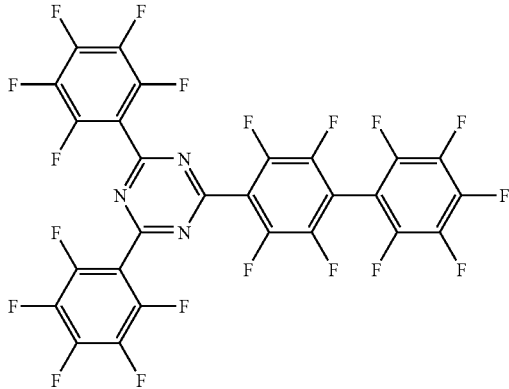 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE 1-continued

| MATERIAL | EXAMPLES OF MATERIAL | PUBLICATIONS |
|---|---|---|
| Zn (N^N) complexes | 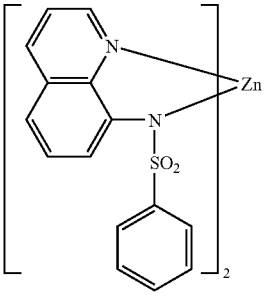 | U.S. Pat. No. 6,528,187 |

EXPERIMENTAL

Compound Examples

Synthesis of Compound 1

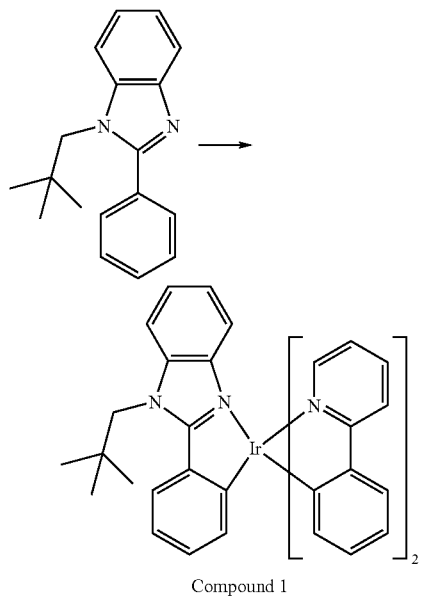

Intermediate 1

Compound 1

Synthesis of Compound 1. Intermediate 1 (1.4 g, 1.96 mmol) and 1-neopentyl-2-phenyl-1H-benzo[d]imidazole (1.6 g, 5.9 mmol) were mixed with 30 mL of ethanol in a three-neck flask under nitrogen. The mixture was heated up to reflux for 24 hours. After cooled to room temperature, the precipitate was collected by filtration. The product was purified by column chromatography using 1:2 dichloromethane and hexanes as eluent. 0.3 g of desired product was obtained after purification.

Synthesis of Compound 2

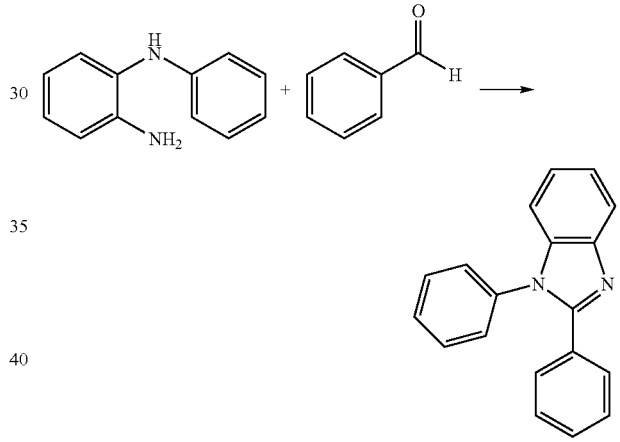

Synthesis of 1,2-diphenyl-1H-benzo[d]imidazole. $N^1$-phenylbenzene-1,2-diamine (4.15 g, 22 mmol) and benzaldehyde (2.1 g, 20 mmol) were mixed with methoxyethanol (60 ml) in a three-neck flask. The mixture was heated up to reflux for 48 hours. After cooled to room temperature, the solvent was evaporated. The residue was purified by column chromatography using dichloromethane to 5% of ethyl acetate in dichloromethane as eluent. 2 g of desired product was obtained.

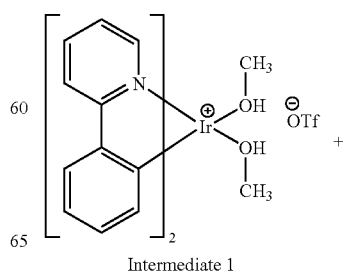

Intermediate 1

-continued

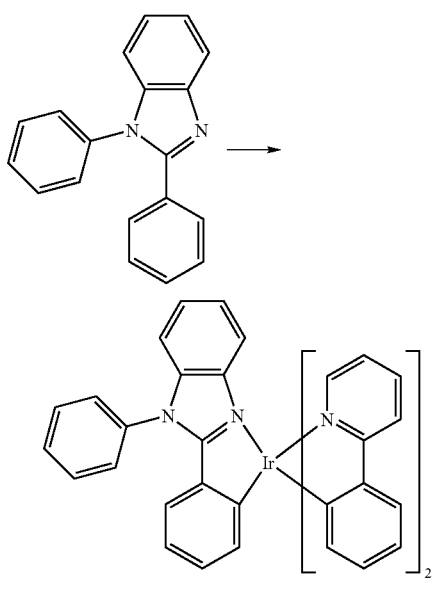

Compound 2

Synthesis of Compound 2. Intermediate 1 (1.32 g, 1.86 mmol) and 1,2-diphenyl-1H-benzo[d]imidazole (1.5 g, 5.5 mmol) were mixed with 40 mL of ethanol in a three-neck flask under nitrogen. The mixture was heated up to reflux for 24 hours. After cooled to room temperature, the precipitate was collected by filtration. The product was purified by column chromatography using 1:2 dichloromethane and hexanes as eluent. 0.3 g of desired product was obtained after purification.

Synthesis of Compound 3

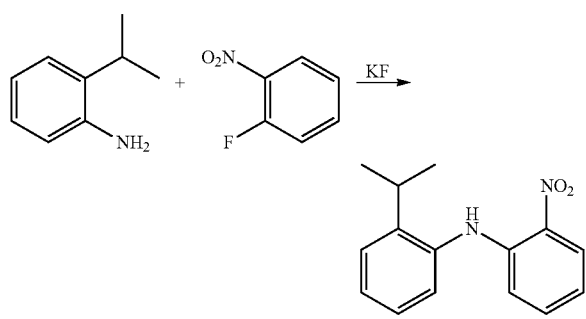

Synthesis of 2-isopropyl-N-(2-nitrophenyl)aniline. 2-isopropylaniline (27 g, 200 mmol), 2-fluoronitrobenzene (14 g, 100 mmol), and potassium fluoride (8.6 g, 150 mmol) were mixed in a one-neck flask. The mixture was heated up to 180° C. under nitrogen for 48 hours. After cooled to room temperature, water (200 mL) was added. The mixture was then extracted with dichloromethane (200 mL) for three times. The solvent was evaporated and the residue was purified by column chromatography using 20% of dichloromethane in hexanes. 22.5 g of desired product was obtained.

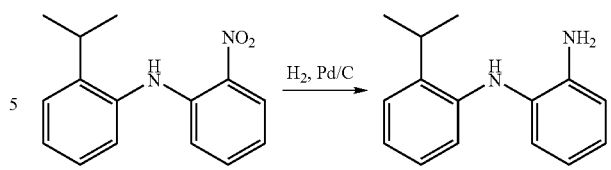

Synthesis of N$^1$-(2-isopropylphenyl)benzene-1,2-diamine. 2-isopropyl-N-(2-nitrophenyl)aniline (22.7 g, 89 mmol) and 10% palladium on carbon (0.6 g) were mixed with 150 mL of ethanol under nitrogen in a plastic coated hydrogenation vessel. The mixture was put on a par hydrogenator and reacted under 40 psi of hydrogen until there is no pressure drop. The catalyst was filtered off through a Celite bed. The solvent was evaporated. The product was used for the next step without further purification. 20 g of desired product was obtained.

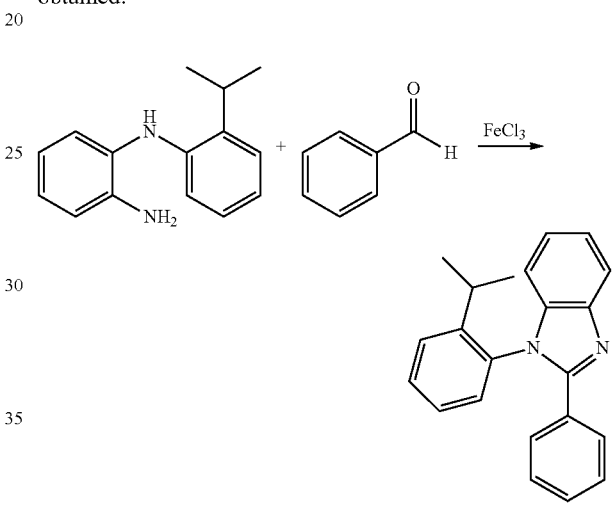

Synthesis of 1-(2-isopropylphenyl)-2-phenyl-1H-benzo[d]imidazole. N$^1$-(2-isopropylphenyl)benzene-1,2-diamine (20 g, 88 mmol) and benzldehyde (8.5 g, 80 mmol) were reacted in acetonitrile (100 mL) under reflux for 3 hours. The reaction mixture was cooled to room temperature. Ferric chloride (0.13 g, 0.8 mmol) was added. The reaction mixture was heated up again to reflux overnight. Air was bubbled through the reaction while reflux. The solvent was evaporated. The residue was dissolved in dichloromethane (200 mL) and ran through a short silica gel plug. The crude product was purified by column chromatography using dichloromethane to 3% of ethyl acetate in dichloromethane. The product was further purified by recrystallizing form ethanol. 8 g of desired product was obtained.

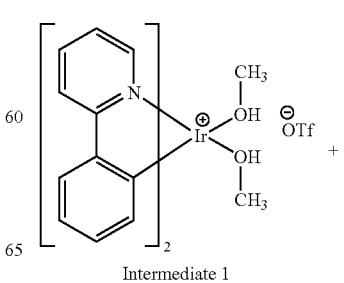

Intermediate 1

-continued

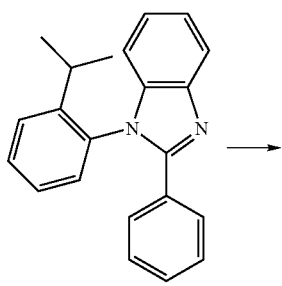

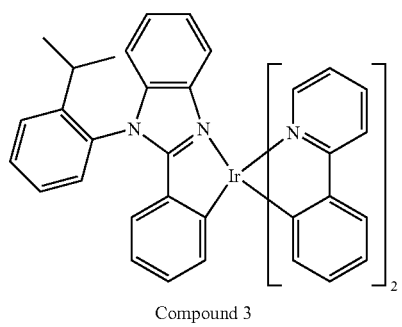

Compound 3

Synthesis of Compound 3. Intermediate 1 (1.5 g, 2.1 mmol) and 142-isopropylphenyl)-2-phenyl-1H-benzo[d]imidazole (2 g, 6.4 mmol) were mixed with 30 ml of ethanol in a three-neck flask under nitrogen. The mixture was heated up to reflux for 24 hours. After cooled to room temperature, the precipitate was collected by filtration. The product was purified by column chromatography using 1:2 dichloromethane and hexanes as eluent. 0.7 g of desired product was obtained after purification.

Synthesis of Compound 4

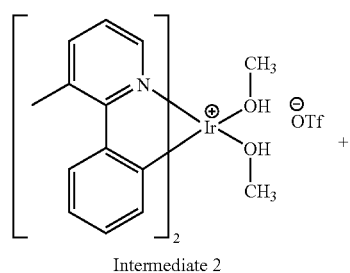

Intermediate 2

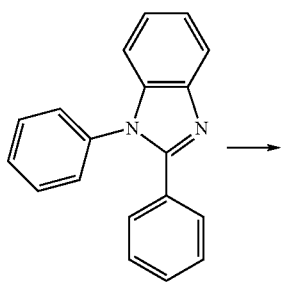

-continued

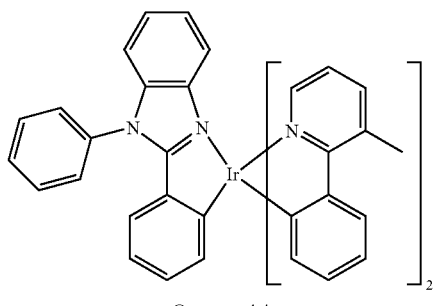

Compound 4

Synthesis of Compound 4. Intermediate 2 (7.4 g, 10 mmol) and 1,2-diphenyl-1H-benzo[d]imidazole (8.11 g, 30 mmol) were mixed with 200 ml of ethanol in a three-neck flask under nitrogen. The mixture was heated up to reflux for 24 hours. After cooled to room temperature, the precipitate was collected by filtration. The product was purified by column chromatography using 1:2 dichloromethane and hexanes as eluent. 1.4 g of desired product was obtained after purification.

Synthesis of Compound 5

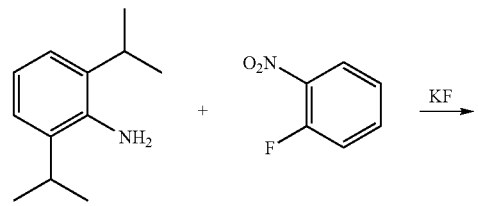

Synthesis of 2,6-diisopropyl-N-(2-nitrophenyl)aniline. 2,6-diisopropylaniline (25 g, 141 mmol), 2-fluoronitrobenzene (10 g, 70 mmol), and potassium fluoride (6.2 g, 106 mmol) were mixed in a one-neck flask. The mixture was heated up to 180° C. under nitrogen for 48 hours. After cooled to room temperature, water (200 mL) was added. The mixture was then extracted with dichloromethane (200 mL) for three times. The solvent was evaporated and the residue was purified by column chromatography using 20% of dichloromethane in hexanes. 10 g of desired product was obtained.

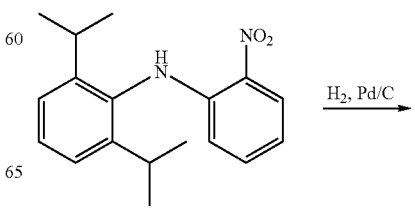

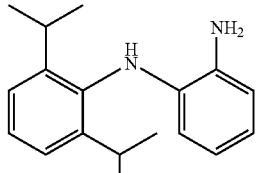
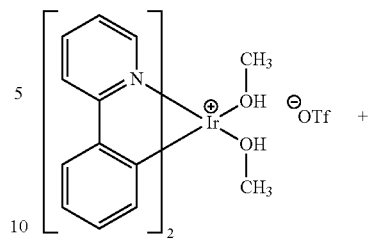

Intermediate 1

Synthesis of N¹-(2,6-diisopropylphenyl)benzene-1,2-diamine. 2,6-diisopropyl-N-(2-nitrophenyl)aniline (9.5 g, 32 mmol) and 10% palladium on carbon (0.4 g) were mixed with 150 ml of ethanol under nitrogen in a plastic coated hydrogenation vessel. The mixture was put on a par hydrogenator and reacted under 40 psi of hydrogen until there is no pressure drop. The catalyst was filtered off through a Celite bed. The solvent was evaporated. The product was used for the next step without further purification. 8.5 g of desired product was obtained.

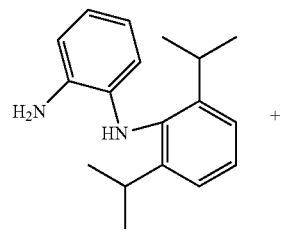
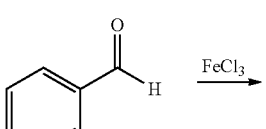
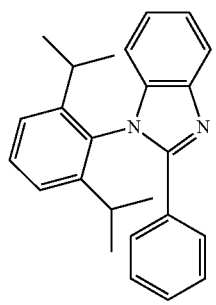

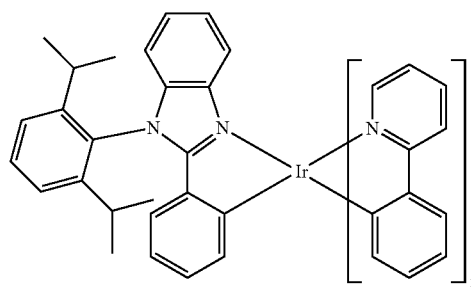

Compound 5

Synthesis of Compound 5. Intermediate 1 (2.1 g, 2.9 mmol) and 1-(2,6-diisopropylphenyl)-2-phenyl-1H-benzo[d]imidazole (3.1 g, 8.7 mmol) were mixed with 60 ml of ethanol in a three-neck flask under nitrogen. The mixture was heated up to reflux for 24 hours. After cooled to room temperature, the precipitate was collected by filtration. The product was purified by column chromatography using 1:2 dichloromethane and hexanes as eluent. 1.1 g of desired product was obtained after purification.

Synthesis of Compound 6

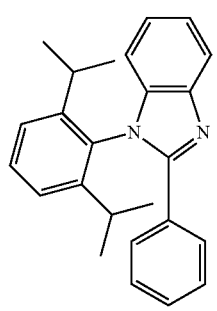

Synthesis of 1-(2,6-diisopropylphenyl)-2-phenyl-1H-benzo[d]imidazole. N¹-(2,6-diisopropylphenyl)benzene-1,2-diamine (8.5 g, 32 mmol) and benzldehyde (3 g, 28.8 mmol) were reacted in acetonitrile (100 ml) under reflux for 3 hours. The reaction mixture was cooled to room temperature. Ferric chloride (0.05 g, 0.28 mmol) was added. The reaction mixture was heated up again to reflux overnight. Air was bubbled through the reaction while reflux. The solvent was evaporated. The residue was dissolved in dichloromethane (200 mL) and ran through a short silica gel plug. The crude product was purified by column chromatography using dichloromethane to 3% of ethyl acetate in dichloromethane. 3.4 g of desired product was obtained.

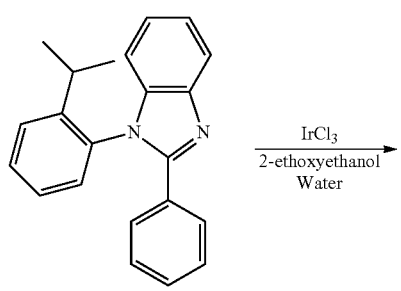

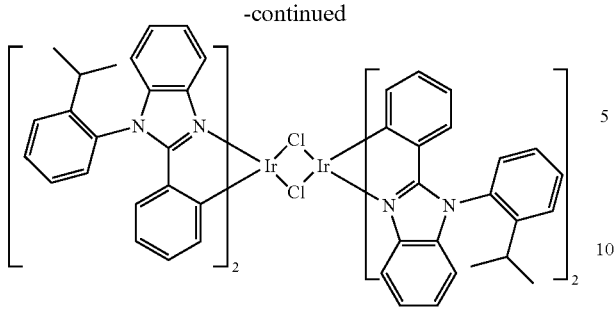

Intermediate 3

Synthesis of Intermediate 3. 1-(2-isopropylphenyl)-2-phenyl-1H-benzo[d]imidazole (3 g, 9.6 mmol) and iridium chloride (1.5 g, 4.36 mmol) were mixed with 60 mL of 2-ethoxyethanol and 20 ml of water in a three-neck flask under nitrogen. The mixture was heated up to reflux for 24 hours. After cooled to room temperature, the precipitate was collected by filtration. The solid was thoroughly washed with methanol and hexanes and then dried under vacuum. 3.5 g of product was obtained.

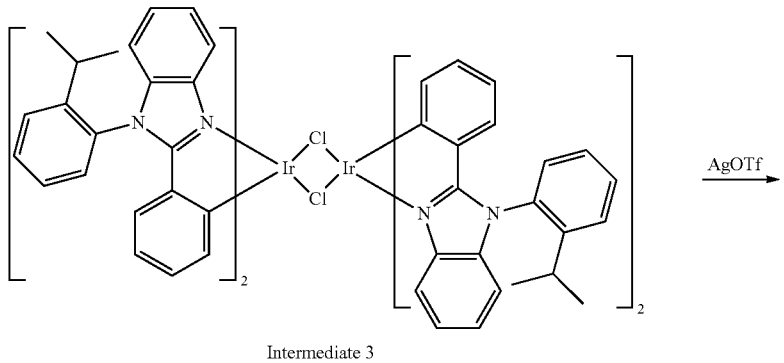

Intermediate 3

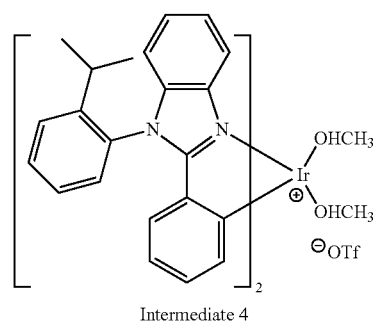

Intermediate 4

Synthesis of intermediate 4. Intermediate 3 (3.5 g, 2.06 mmol) and silver triflate (1.06 g, 4.12 mmol) were mixed with 300 ml of dichloromethane and 30 mL of methanol. The mixture was stirred at room temperature for 24 hours. The solid was filtered. The filtrate was evaporated to dryness. 4.2 g of product was obtained.

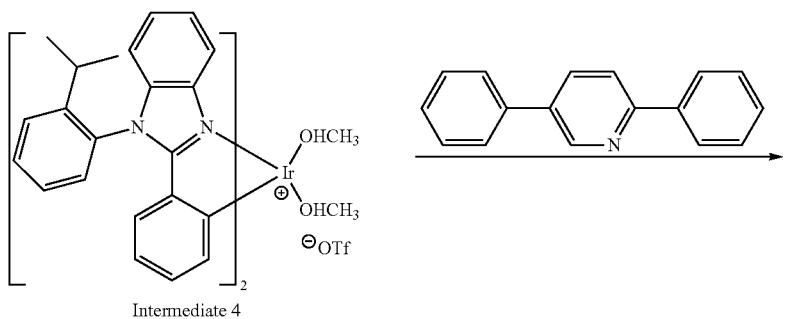

Intermediate 4

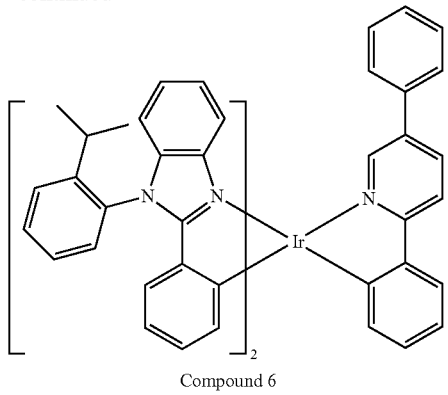

Compound 6

Synthesis of Compound 6. Intermediate 4 (2.0 g, 1.95 mmol) and 2,5-diphenylpyridine (1.4 g, 5.83 mmol) were mixed with 50 mL of ethanol in a three-neck flask under nitrogen. The mixture was heated up to reflux for 24 hours. After cooled to room temperature, the precipitate was collected by filtration. The product was purified by column chromatography using 1:1 dichloromethane and hexanes as eluent. 0.5 g of desired product was obtained after purification.

Synthesis of Compound 7 and Compound 8

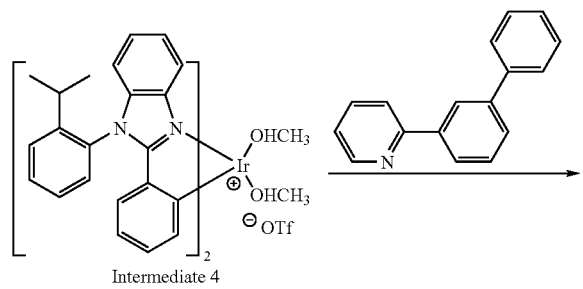

Intermediate 4

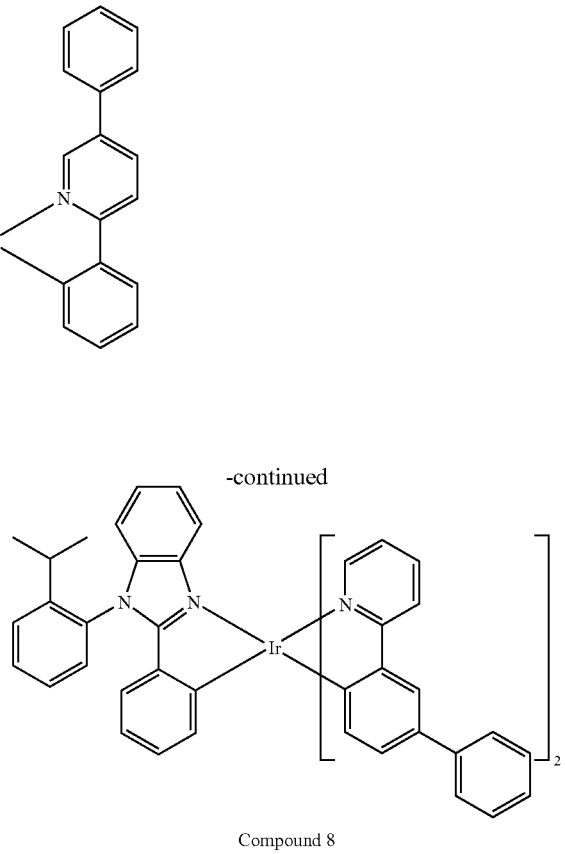

Compound 8

Synthesis of Compound 7 and Compound 8. Intermediate 4 (2.0 g, 1.95 mmol) and 2-(biphenyl-3-yl)pyridine (1.5 g, 5.8 mmol) were mixed with 60 ml of ethanol in a three-neck flask under nitrogen. The mixture was heated up to reflux for 24 hours. After cooled to room temperature, the precipitate was collected by filtration. The product was purified by column chromatography using 1:1 dichloromethane and hexanes as eluent. 1.4 g of Compound 7 and 0.4 g of Compound 8 were collected.

Synthesis of Compound 9

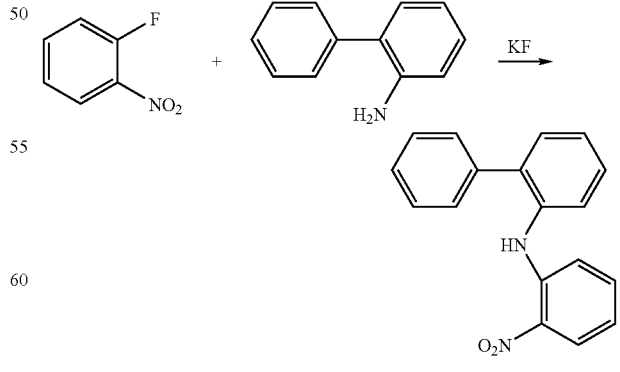

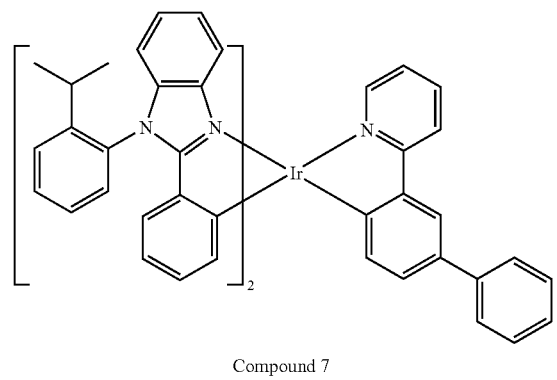

Compound 7

Synthesis of N-(2-nitrophenyl)biphenyl-2-amine. A mixture of 1-fluoro-2-nitrobenzene (13.06 g, 92.6 mmol), 2-aminobiphenyl (31.3 g, 185.2 mmol), and potassium fluoride (8.1 g, 138.9 mmol) was prepared in a 100 mL round bottom flask. The flask was evacuated and replaced with nitrogen. The mixture was heated to 200° C. overnight. The reaction mixture was cooled and ethyl acetate and water were added. The layers were separated and the aqueous layer was extracted with ethyl acetate. The organic layers were dried over magnesium sulfate, filtered, and evaporated. The residue was preabsorbed onto Celite and purified by column chromatography eluting with 0, 2, and 5% ethyl acetate/hexanes. 24.5 g (91%) of product was obtained.

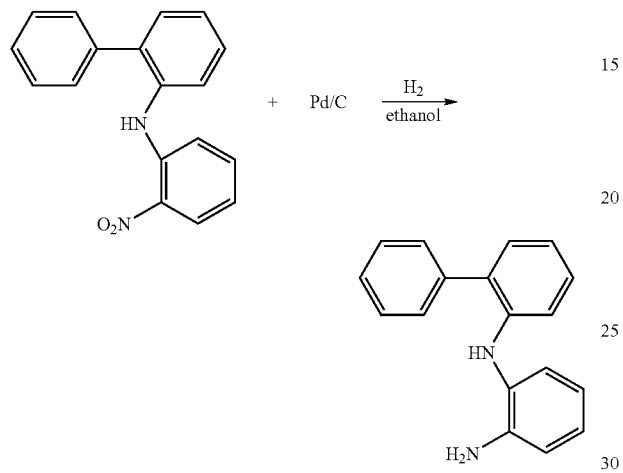

Synthesis of $N^1$-(biphenyl-2-yl)benzene-1,2-diamine. N-(2-nitrophenyl)biphenyl-2-amine (19.69 g, 67.8 mmol), 10% palladium on carbon (0.29 g, 0.27 mmol), and 150 mL of ethanol was added to a Parr hydrogenator bottle. The mixture was hydrogenated on a Parr hydrogenator until no more hydrogen was taken up by the solution. The solution was filtered through Celite to remove the catalyst, Celite was washed with dichloromethane, the filtrate was evaporated to yield a brown oil, 14.8 g (84%). The product was used for the next step without further purification.

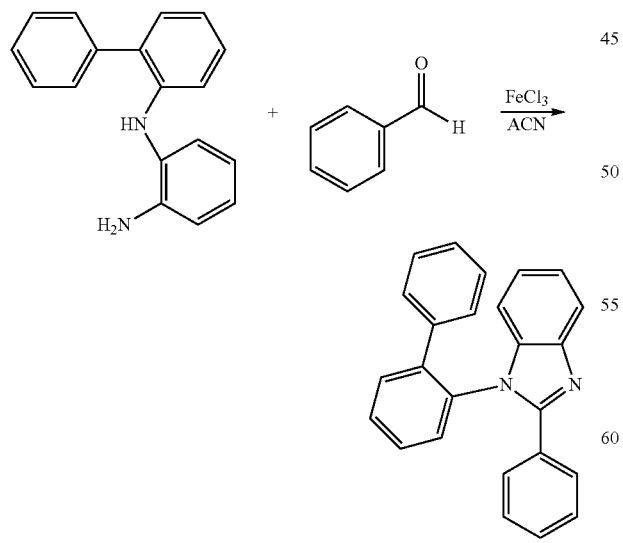

Synthesis of 1-(biphenyl-2-yl)-2-phenyl-1H-benzo[d]imidazole. N'-(biphenyl-2-yl)benzene-1,2-diamine (14.8 g, 56.85 mmol), benzaldehyde (5.2 mL, 51.68 mmol), and 200 mL of acetonitrile were added to a 500 mL 3-neck round bottom flask. The mixture was heated to reflux overnight under nitrogen. 80 mg (0.49 mmol) of iron (III) chloride was added and mixture was bubbled with air directly into cooled solution. After 3 hours the solvent was evaporated and the residue dissolved in dichloromethane and the solution passed through a silica gel plug eluting with 0 to 10% ethyl acetate/dichloromethane. 6.56 g (37%) product was obtained.

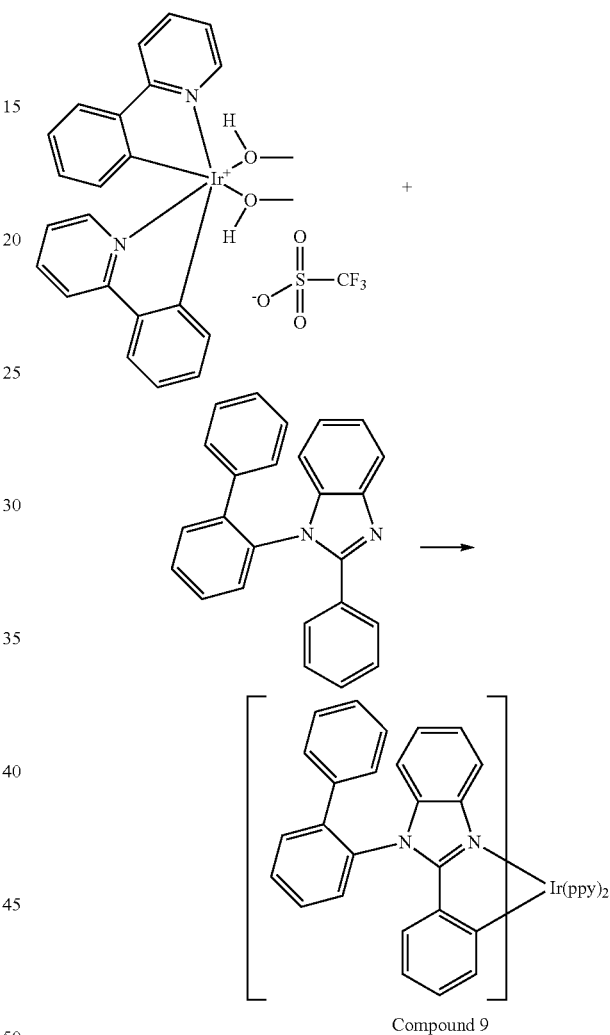

Compound 9

Synthesis of Compound 9. The triflate complex (2.06 g, 2.89 mmol), 1-(biphenyl-2-yl)-2-phenyl-1H-benzo[d]imidazole (4 g, 11.55 mmol), and 100 mL ethanol were added to a 250 mL round bottom flask. The mixture was heated to reflux overnight under nitrogen. The precipitate was collected by filtration and then purified by column. 0.75 g of product was obtained.

Device Examples

All example devices were fabricated by high vacuum (<$10^{-7}$ Torr) thermal evaporation. The anode electrode is ~800 Å, 1200 Å or 2000 Å of indium tin oxide (ITO) on glass, or 800 Å Sapphire/IZO. The cathode consists of 10 Å of LiF followed by 1000 Å of Al. All devices are encapsulated with a glass lid sealed with an epoxy resin in a nitrogen glove box (<1 ppm of H₂O and O₂) immediately after fabrication, and a moisture getter was incorporated inside the package.

The organic stack of Device Examples 1-10 consisted of sequentially, from the ITO surface (1200 Å), 100 Å of Compound C as the hole injection layer (HIL), 300 Å of 4,4'-bis[N-(1-naphthyl)-N-phenylamino]biphenyl (α-NPD) as the hole transporting layer (HTL), 300 Å of Host-1 or Host-2 doped with 7-10% of the dopant emitter (invention Compounds 1-3) as the emissive layer (EML), 50 Å or 100 Å of Host 1 or Host 2 as the blocking layer (BL), and 400 Å or 450 Å of tris-8-hydroxyquinoline aluminum (Alq₃) as the ETL.

Comparative Examples 1-4 were fabricated similarly to the Device Examples except that Compound B or Compound C was used as the emissive dopant.

As used herein, the following compounds have the following structures:

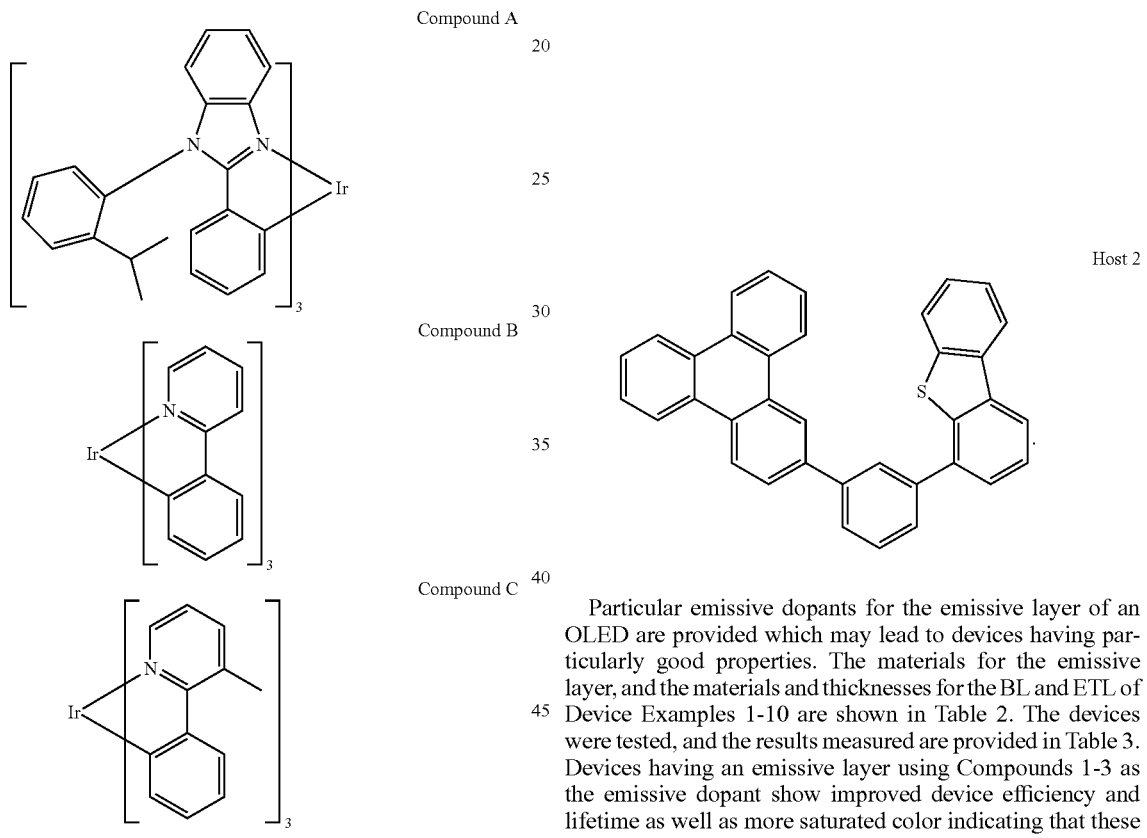

Particular emissive dopants for the emissive layer of an OLED are provided which may lead to devices having particularly good properties. The materials for the emissive layer, and the materials and thicknesses for the BL and ETL of Device Examples 1-10 are shown in Table 2. The devices were tested, and the results measured are provided in Table 3. Devices having an emissive layer using Compounds 1-3 as the emissive dopant show improved device efficiency and lifetime as well as more saturated color indicating that these heteroleptic compounds may be beneficial.

TABLE 2

| Device Example | HIL | HTL | Host | A % | BL | ETL |
| --- | --- | --- | --- | --- | --- | --- |
| Example 1 | Compound C 100 Å | NPD 300 Å | Host-1 | Compound 1 7% | Host-1 50 Å | Alq 450 Å |
| Example 2 | Compound C 100 Å | NPD 300 Å | Host-1 | Compound 1 10% | Host-1 50 Å | Alq 450 Å |
| Example 3 | Compound C 100 Å | NPD 300 Å | Host-1 | Compound 2 7% | Host-1 50 Å | Alq 450 Å |
| Example 4 | Compound C 100 Å | NPD 300 Å | Host-1 | Compound 2 10% | Host-1 50 Å | Alq 450 Å |
| Example 5 | Compound C 100 Å | NPD 300 Å | Host-2 | Compound 3 7% | Host-2 100 Å | Alq 400 Å |
| Example 6 | Compound C 100 Å | NPD 300 Å | Host-2 | Compound 3 10% | Host-2 100 Å | Alq 400 Å |
| Example 7 | Compound C 100 Å | NPD 300 Å | Host-2 | Compound 4 7% | Host-2 100 Å | Alq 400 Å |
| Example 8 | Compound C 100 Å | NPD 300 Å | Host-2 | Compound 4 10% | Host-2 100 Å | Alq 400 Å |
| Example 9 | Compound C 100 Å | NPD 300 Å | Host-2 | Compound 5 7% | Host-2 100 Å | Alq 400 Å |
| Example 10 | Compound C 100 Å | NPD 300 Å | Host-2 | Compound 5 10% | Host-2 100 Å | Alq 400 Å |
| Comparative Example 1 | Compound C 100 Å | NPD 300 Å | Host-2 | Compound B 7% | Host-2 100 Å | Alq 400 Å |
| Comparative Example 2 | Compound C 100 Å | NPD 300 Å | Host-2 | Compound B 10% | Host-2 100 Å | Alq 400 Å |

TABLE 2-continued

| Device Example | HIL | HTL | Host | A % | BL | ETL |
|---|---|---|---|---|---|---|
| Comparative Example 3 | Compound C 100 Å | NPD 300 Å | Host-1 | Compound C 10% | Host-1 50 Å | Alq 450 Å |
| Comparative Example 4 | Compound C 100 Å | NPD 300 Å | Host-2 | Compound C 7% | Host-2 100 Å | Alq 400 Å |

TABLE 3

| Device Example | λ max, (nm) | FWHM (nm) | CIE X | CIE Y | V (V) | At L = 1000 cd/m² LE (cd/A) | EQE (%) | PE lm/W | At J = 40 mA/cm² Lo, (cd/m²) | RT 80% (hr) |
|---|---|---|---|---|---|---|---|---|---|---|
| Example 1 | 521 | 74 | 0.331 | 0.615 | 7 | 45 | 12.5 | 20.2 | 10,883 | 87 |
| Example 2 | 523 | 75 | 0.338 | 0.614 | 6.3 | 51.5 | 14.3 | 25.9 | 14,139 | 99 |
| Example 3 | 522 | 80 | 0.347 | 0.607 | 6 | 57 | 16.1 | 29.6 | 16,045 | 127 |
| Example 4 | 526 | 86 | 0.363 | 0.598 | 6.6 | 52.6 | 15 | 24.9 | 16,197 | 149 |
| Example 5 | 519 | 73 | 0.325 | 0.618 | 6.3 | 51 | 14.2 | 25.5 | 13,159 | 200 |
| Example 6 | 520 | 72 | 0.324 | 0.622 | 5.6 | 55.1 | 15.3 | 31.1 | 15,610 | 280 |
| Example 7 | 527 | 78 | 0.360 | 0.603 | 6 | 59.9 | 16.7 | 31.2 | 15,345 | 150 |
| Example 8 | 528 | 88 | 0.366 | 0.600 | 5.4 | 67.7 | 19 | 39.2 | 19,894 | 150 |
| Example 9 | 519 | 71 | 0.320 | 0.622 | 6.1 | 50.4 | 14 | 26.1 | 13,610 | 200 |
| Example 10 | 519 | 72 | 0.325 | 0.620 | 5.7 | 50.5 | 14 | 27.6 | 14,262 | 270 |
| Comparative Example 1 | 519 | 74 | 0.321 | 0.621 | 6 | 45.1 | 12.6 | 23.6 | 13,835 | 196 |
| Comparative Example 2 | 521 | 76 | 0.325 | 0.618 | 6 | 44 | 12.3 | 22.9 | 13,469 | 200 |
| Comparative Example 3 | 529 | 79 | 0.361 | 0.604 | 5.9 | 46.7 | 12.9 | 24.7 | 14,575 | 97 |
| Comparative Example 4 | 527 | 74 | 0.348 | 0.613 | 6 | 56.4 | 15.4 | 29.7 | 16,108 | 290 |

From Device Examples 1-10, it can be seen that the invention compounds as emissive dopants in green phosphorescent OLEDs give high device efficiency, long operational lifetime and more saturated color. Compound 1 and 2 showed better efficiency, more saturated color, and longer lifetime than Compound C as can be seen from Device Examples 1-4 and Comparative Example 3. Compound 3 has longer lifetime and higher efficiency than Compound B as can be seen from Device Examples 5 and 6 and Comparative Examples 1 and 2. Notably, devices containing Compound 3 as an emissive dopant also showed more saturated color and a narrower emission spectrum than Compound C as shown in Comparative Example 4.

These data show that phenylpyridine and phenylbenzimidazole containing heteroleptic compounds are excellent emissive dopants for phosphorescent OLEDs providing better color, longer lifetime, and higher efficiency.

Particular emissive dopants for use in the emissive layer of an OLED are provided These dopants may provide devices having particularly good properties. The materials for the emissive layer, and the materials and thicknesses for the BL and ETL of Device Examples 1-16 are shown in Table 4. The devices were tested, and the results measured are provided in Table 5. Devices having an emissive layer using Compounds 1-6, 8 and 9 as the emissive dopant show improved device efficiency and lifetime as well as more saturated color indicating that these heteroleptic compounds may be beneficial.

TABLE 4

| Device Example | HIL | HTL | Host | A % | BL | ETL |
|---|---|---|---|---|---|---|
| Example 1 | Compound C 100 Å | NPD 300 Å | Host-1 | Compound 1 7% | Host-1 50 Å | Alq 450 Å |
| Example 2 | Compound C 100 Å | NPD 300 Å | Host-1 | Compound 1 10% | Host-1 50 Å | Alq 450 Å |
| Example 3 | Compound C 100 Å | NPD 300 Å | Host-1 | Compound 2 7% | Host-1 50 Å | Alq 450 Å |
| Example 4 | Compound C 100 Å | NPD 300 Å | Host-1 | Compound 2 10% | Host-1 50 Å | Alq 450 Å |
| Example 5 | Compound C 100 Å | NPD 300 Å | Host-2 | Compound 3 7% | Host-2 100 Å | Alq 400 Å |
| Example 6 | Compound C 100 Å | NPD 300 Å | Host-2 | Compound 3 10% | Host-2 100 Å | Alq 400 Å |
| Example 7 | Compound C 100 Å | NPD 300 Å | Host-2 | Compound 4 7% | Host-2 100 Å | Alq 400 Å |
| Example 8 | Compound C 100 Å | NPD 300 Å | Host-2 | Compound 4 10% | Host-2 100 Å | Alq 400 Å |
| Example 9 | Compound C 100 Å | NPD 300 Å | Host-2 | Compound 5 7% | Host-2 100 Å | Alq 400 Å |
| Example 10 | Compound C 100 Å | NPD 300 Å | Host-2 | Compound 5 10% | Host-2 100 Å | Alq 400 Å |
| Example 11 | Compound C 100 Å | NPD 300 Å | Host-2 | Compound 6 7% | Host-2 100 Å | Alq 400 Å |
| Example 12 | Compound C 100 Å | NPD 300 Å | Host-2 | Compound 6 10% | Host-2 100 Å | Alq 400 Å |
| Example 13 | Compound C 100 Å | NPD 300 Å | Host-2 | Compound 8 7% | Host-2 100 Å | Alq 400 Å |
| Example 14 | Compound C 100 Å | NPD 300 Å | Host-2 | Compound 8 10% | Host-2 100 Å | Alq 400 Å |
| Example 15 | Compound C 100 Å | NPD 300 Å | Host-2 | Compound 9 7% | Host-2 100 Å | Alq 400 Å |
| Example 16 | Compound C 100 Å | NPD 300 Å | Host-2 | Compound 9 10% | Host-2 100 Å | Alq 400 Å |

TABLE 4-continued

| Device Example | HIL | HTL | Host | A % | BL | ETL |
|---|---|---|---|---|---|---|
| Comparative Example 1 | Compound C 100 Å | NPD 300 A | Host-2 | Compound B 7% | Host-2 100 Å | Alq 400 Å |
| Comparative Example 2 | Compound C 100 Å | NPD 300 Å | Host-2 | Compound B 10% | Host-2 100 Å | Alq 400 Å |
| Comparative Example 3 | Compound C 100 Å | NPD 300 Å | Host-1 | Compound C 10% | Host-1 50 Å | Alq 450 Å |
| Comparative Example 4 | Compound C 100 Å | NPD 300 Å | Host-2 | Compound C 7% | Host-2 100 Å | Alq 400 Å |

TABLE 5

| Device Example | λ max, (nm) | FWHM (nm) | CIE X | CIE Y | V (V) | At L = 1000 cd/m² LE (cd/A) | EQE (%) | PE lm/W | At J = 40 mA/cm² Lo, (cd/m²) | $RT_{80\%}$ (hr) |
|---|---|---|---|---|---|---|---|---|---|---|
| Example 1 | 521 | 74 | 0.331 | 0.615 | 7 | 45 | 12.5 | 20.2 | 10,883 | 87 |
| Example 2 | 523 | 75 | 0.338 | 0.614 | 6.3 | 51.5 | 14.3 | 25.9 | 14,139 | 99 |
| Example 3 | 522 | 80 | 0.347 | 0.607 | 6 | 57 | 16.1 | 29.6 | 16,045 | 127 |
| Example 4 | 526 | 86 | 0.363 | 0.598 | 6.6 | 52.6 | 15 | 24.9 | 16,197 | 149 |
| Example 5 | 519 | 73 | 0.325 | 0.618 | 6.3 | 51 | 14.2 | 25.5 | 13,159 | 200 |
| Example 6 | 520 | 72 | 0.324 | 0.622 | 5.6 | 55.1 | 15.3 | 31.1 | 15,610 | 280 |
| Example 7 | 527 | 78 | 0.360 | 0.603 | 6 | 59.9 | 16.7 | 31.2 | 15,345 | 150 |
| Example 8 | 528 | 88 | 0.366 | 0.600 | 5.4 | 67.7 | 19 | 39.2 | 19,894 | 150 |
| Example 9 | 519 | 71 | 0.320 | 0.622 | 6.1 | 50.4 | 14 | 26.1 | 13,610 | 200 |
| Example 10 | 519 | 72 | 0.325 | 0.620 | 5.7 | 50.5 | 14 | 27.6 | 14,262 | 270 |
| Example 11 | 547 | 70 | 0.426 | 0.561 | 5.7 | 70.3 | 19.7 | 38.5 | 18,699 | 280 |
| Example 12 | 549 | 69 | 0.432 | 0.557 | 5.4 | 74.7 | 21 | 43.6 | 21,276 | 420 |
| Example 13 | 527 | 68 | 0.342 | 0.620 | 6 | 54.5 | 14.7 | 28.4 | 16,098 | 360 |
| Example 14 | 527 | 68 | 0.339 | 0.623 | 5.5 | 53.2 | 14.3 | 30.2 | 16,462 | 425 |
| Example 15 | 520 | 70 | 0.325 | 0.620 | 6.1 | 55.3 | 15.3 | 28.5 | 14,113 | 240 |
| Example 16 | 520 | 70 | 0.325 | 0.622 | 5.7 | 57.3 | 15.8 | 31.6 | 16,065 | 280 |
| Comparative Example 1 | 519 | 74 | 0.321 | 0.621 | 6 | 45.1 | 12.6 | 23.6 | 13,835 | 196 |
| Comparative Example 2 | 521 | 76 | 0.325 | 0.618 | 6 | 44 | 12.3 | 22.9 | 13,469 | 200 |
| Comparative Example 3 | 529 | 79 | 0.361 | 0.604 | 5.9 | 46.7 | 12.9 | 24.7 | 14,575 | 97 |
| omparative Example 4 | 527 | 74 | 0.348 | 0.613 | 6 | 56.4 | 15.4 | 29.7 | 16,108 | 290 |

From Device Examples 1-16, it can be seen that green OLEDs which comprise an invention compound as an emitting dopant provide excellent properties. Compounds 6, 8, and 9 showed more saturated color, better efficiency, and longer lifetime than Compounds B and C, as can be seen from Device Examples 11-14 and Comparative Examples 1-4. Devices containing Compound 6 showed improved lifetime as compared to devices using Compound B or Compound C. Devices using Compound 8 or Compound 9 showed more saturated color, improved efficiency and a longer lifetime than devices using Compound B or Compound C.

This data shows that heteroleptic compound containing phenylpyridine and phenylbenzimidazole are great emitting dopants for phosphorescent OLEDs. These compounds provide devices having improved efficiency, improved color, and longer lifetime.

Figure 3:
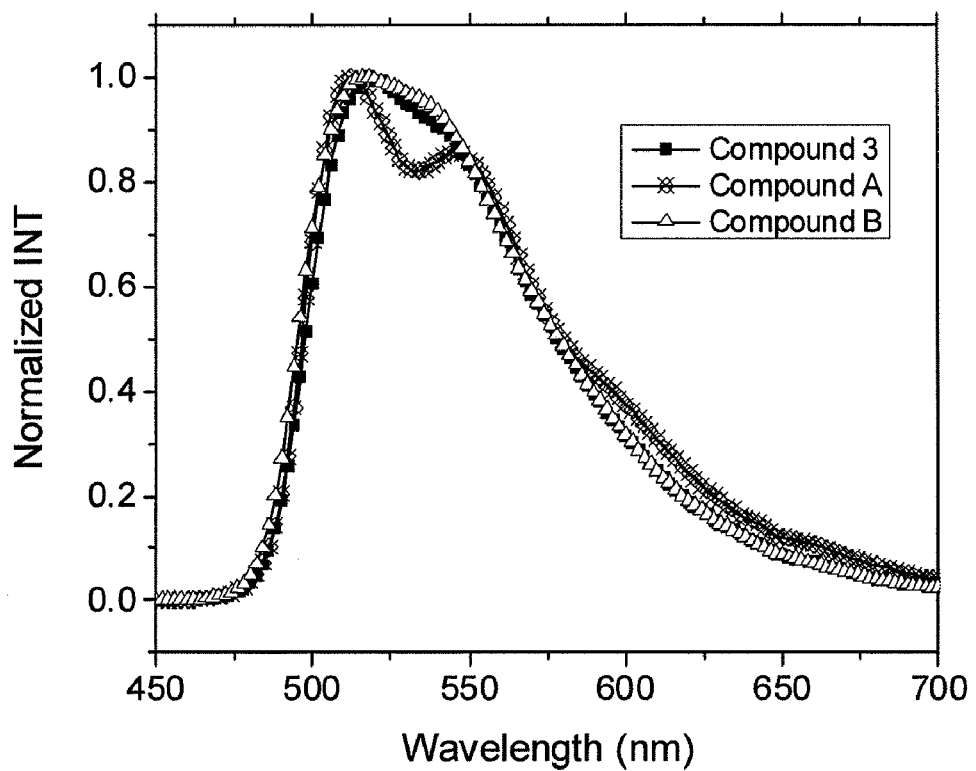
FIG. 3 shows solution photoluminescence spectra of homoleptic and heteroleptic compounds.

FIG. 3 shows the solution photoluminescence (PL) spectra of Compound 3, Compound A, and Compound B. The homoleptic complex Compound A showed vibronic structures. The heteroleptic complex Compound 3 has a similar shape as Compound B. However, the emission of Compound 3 is narrower than Compound B, which indicates that both ligands may contribute to the emission. In addition, Compound 3 can be evaporated at less than 220° C. under high vacuum, which is about 20 degrees lower than Compound B and about 60 degrees lower than Compound A.

Figure 4:
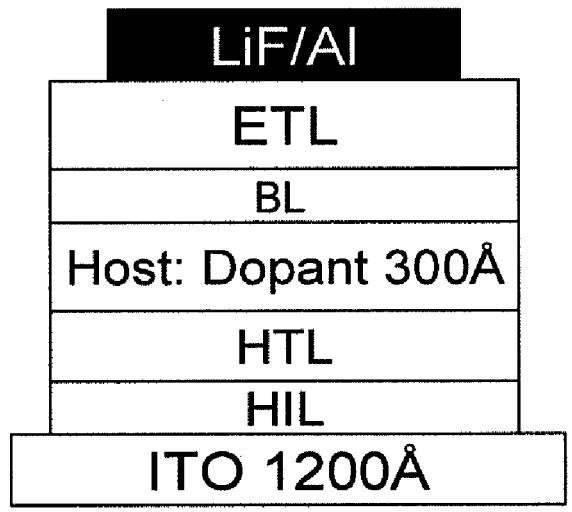
FIG. 4 shows a phosphorescent organic light emitting device structure.

FIG. 4 shows a general phosphorescent organic light emitting device.

Figure 5:
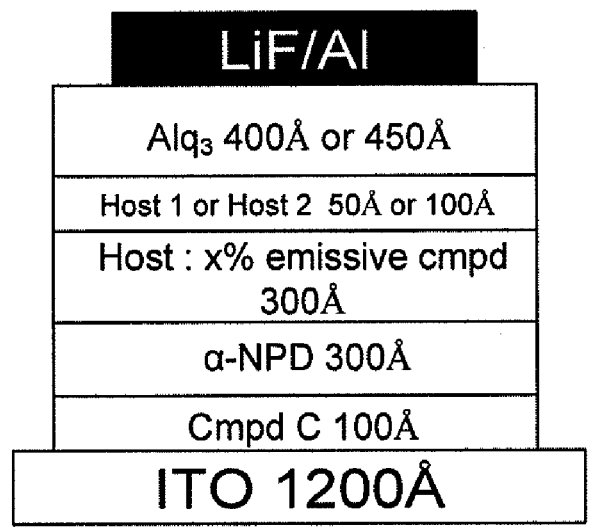
FIG. 5 shows a phosphorescent organic light emitting device containing the inventive compounds.

FIG. 5 shows a phosphorescent organic light emitting device having an emissive layer containing the inventive compound as an emissive dopant. The device of FIG. 5 includes a 100 Å thick hole injection layer of Compound C, a 300 Å thick hole transport layer of NPD, a 300 Å thick emissive layer of a host material doped with X % of the inventive compound, a 50 Å or 100 Å A thick blocking layer of Host-1 or Host-2, and a 400 Å or 450 Å thick electron transport layer of $Alq_3$, and a LiF/Al cathode. X is either 7% or 10%.

Figure 6:
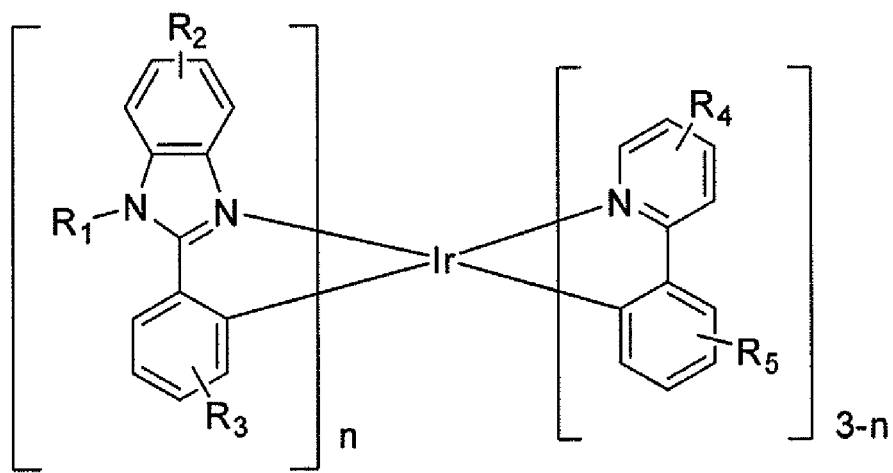
FIG. 6 shows a heteroleptic compound.

FIG. 6 shows a heteroleptic compound containing phenylpyridine and phenylbenzimidazole.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

What is claimed is:

1. A heteroleptic iridium compound Ir(L1)$_n$(L2)$_{3-n}$ having the formula:

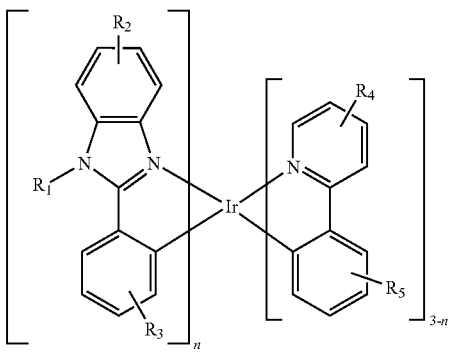

wherein n=1 or 2;
wherein

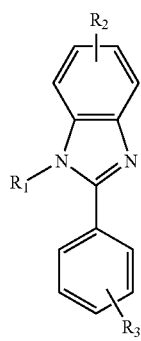

is L1;
wherein

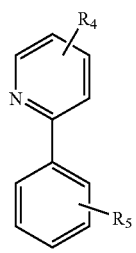

is L2;
wherein $R_2$, $R_3$, $R_4$ and $R_5$ may represent mono, di, tri, or tetra substitutions; and
wherein $R_2$, $R_3$, $R_4$, and $R_5$ are each independently selected from the group consisting of hydrogen, alkyl, heteroalkyl, aryl, substituted aryl, heteroaryl, and substituted heteroaryl;

wherein $R_1$ is

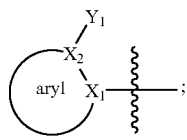

wherein $X_1$ and $X_2$ are independently selected from C and N;
wherein $Y_1$ is not hydrogen; and
wherein $Y_1$ may be joined to other substituents on the aryl ring.

2. The compound of claim 1, wherein n=1.

3. The compound of claim 1, wherein the compound has the formula:

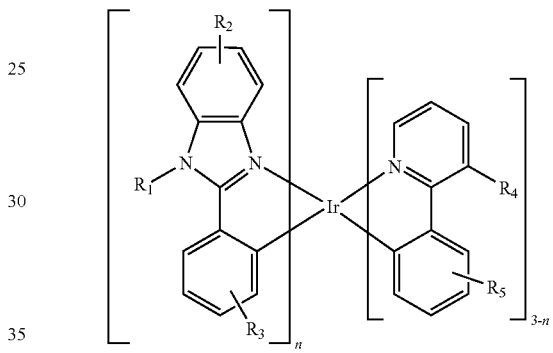

wherein $R_4$ is hydrogen or methyl.

4. The compound of claim 1, wherein each of $R_2$, $R_3$, and $R_5$ are hydrogen.

5. The compound of claim 1, wherein L1 is selected from the group consisting of:

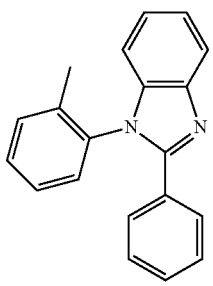

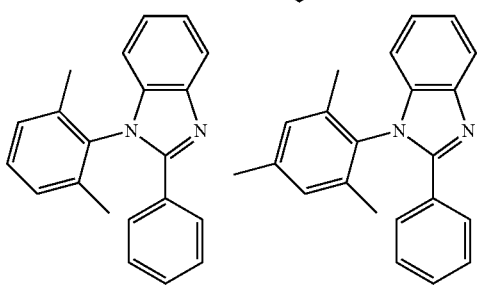

115
-continued
116
-continued
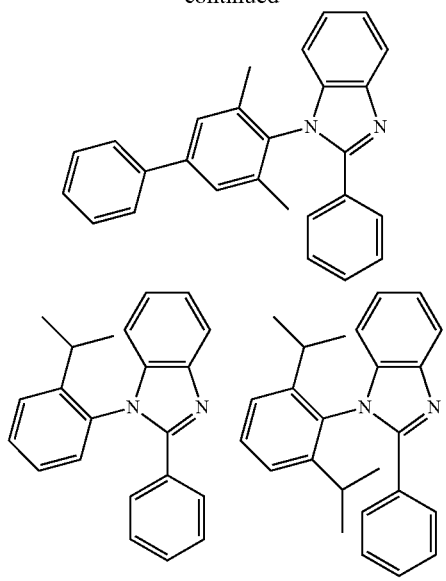
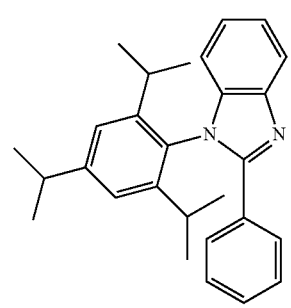
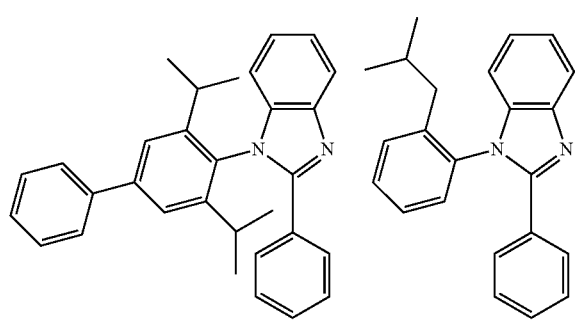
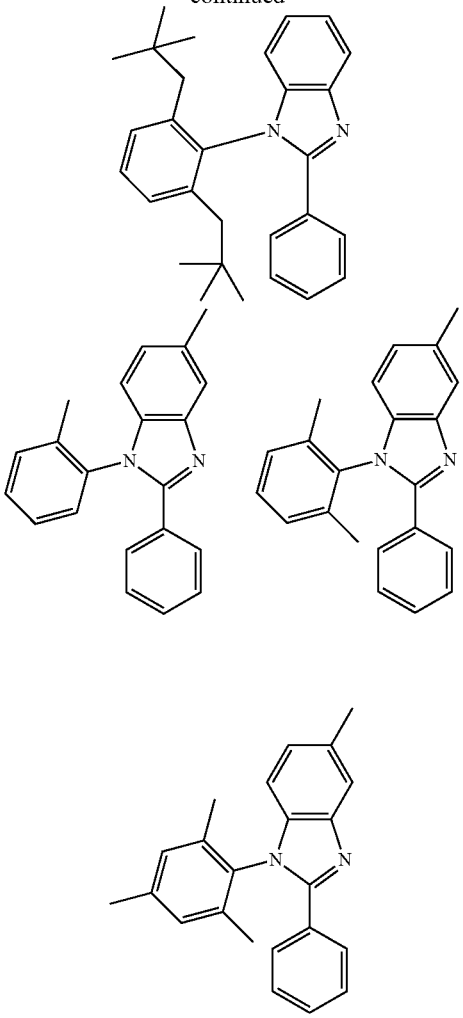
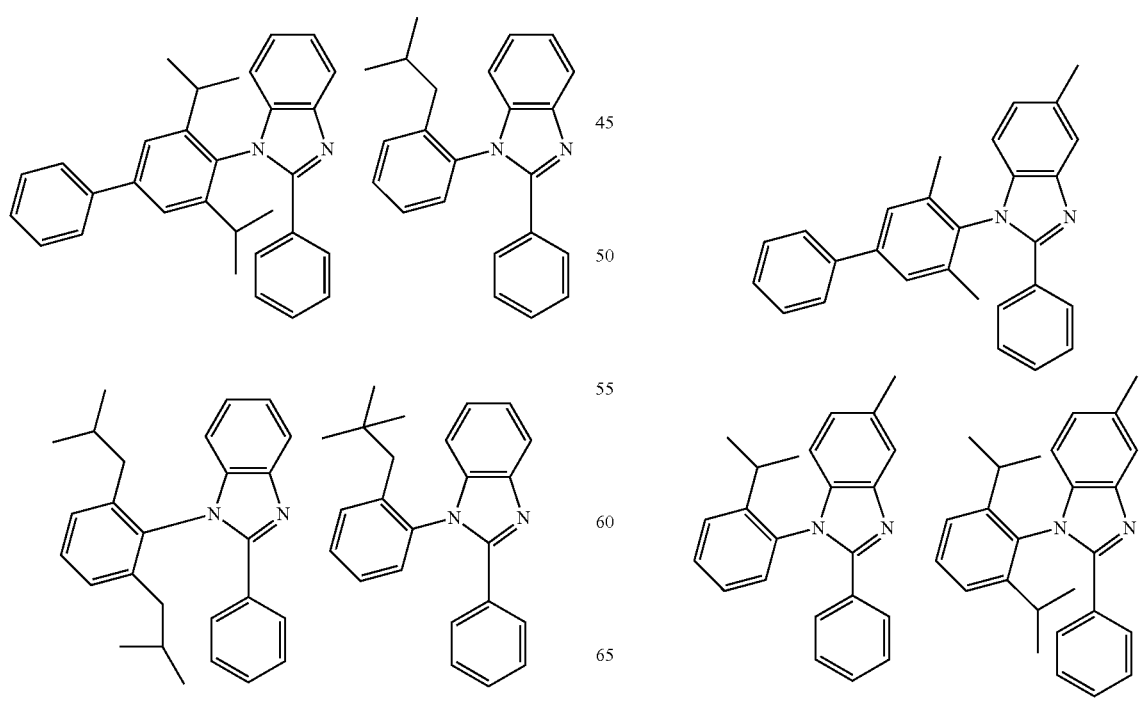

117
-continued
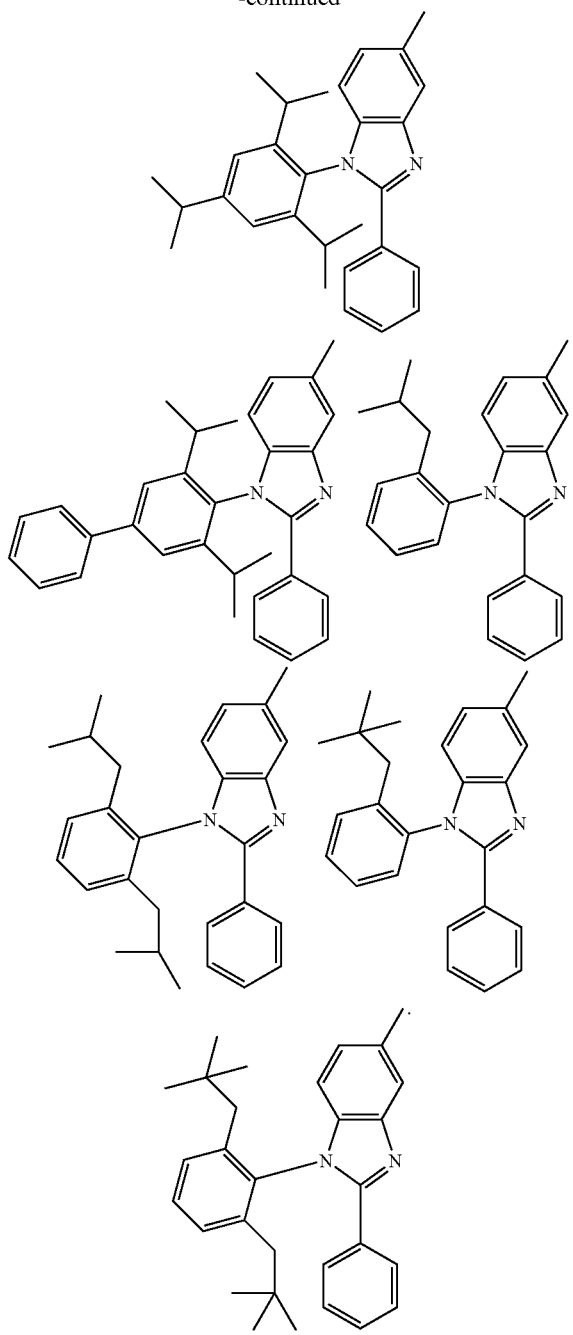
6. The compound of claim 5, wherein L2 is selected from the group consisting of:
118
-continued
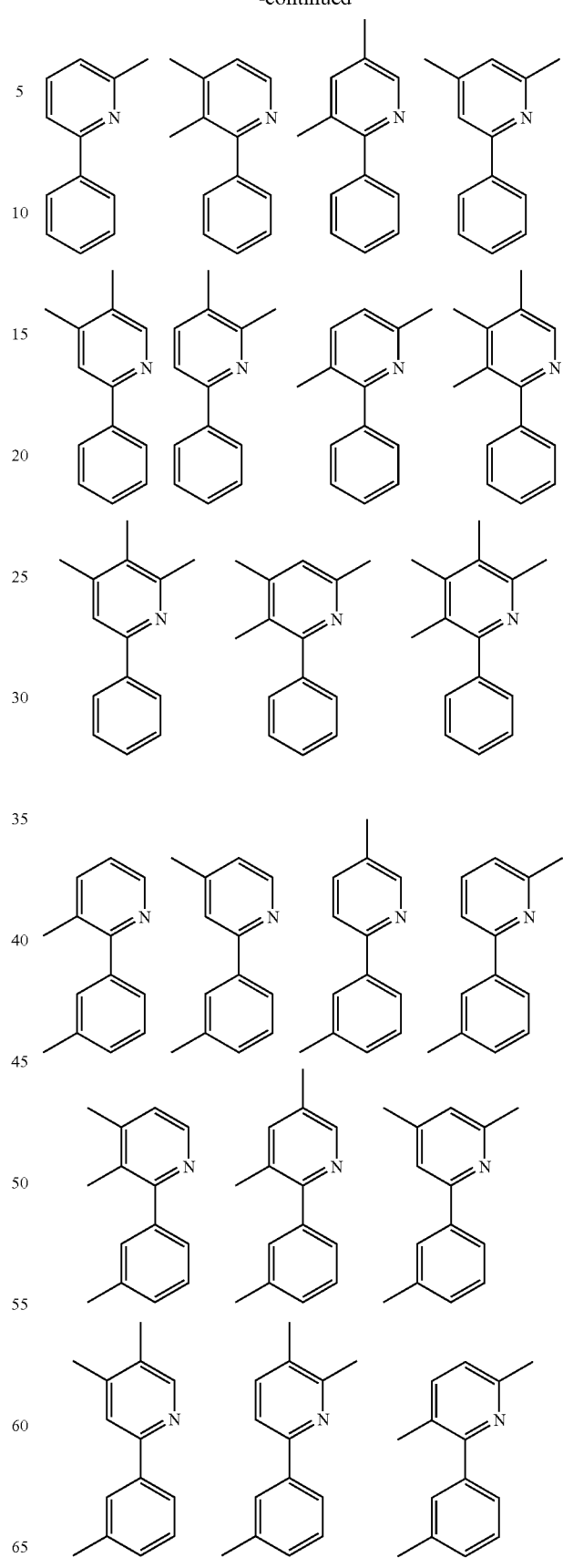

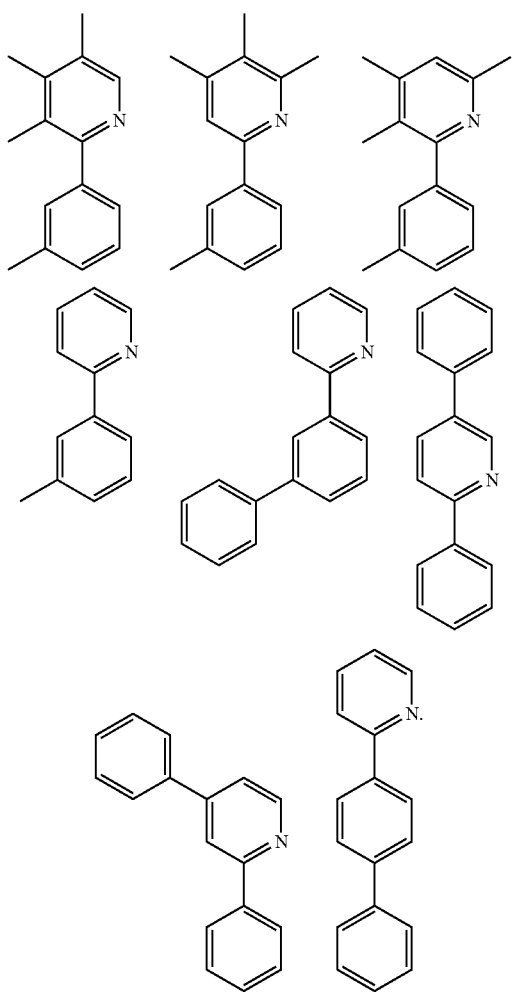
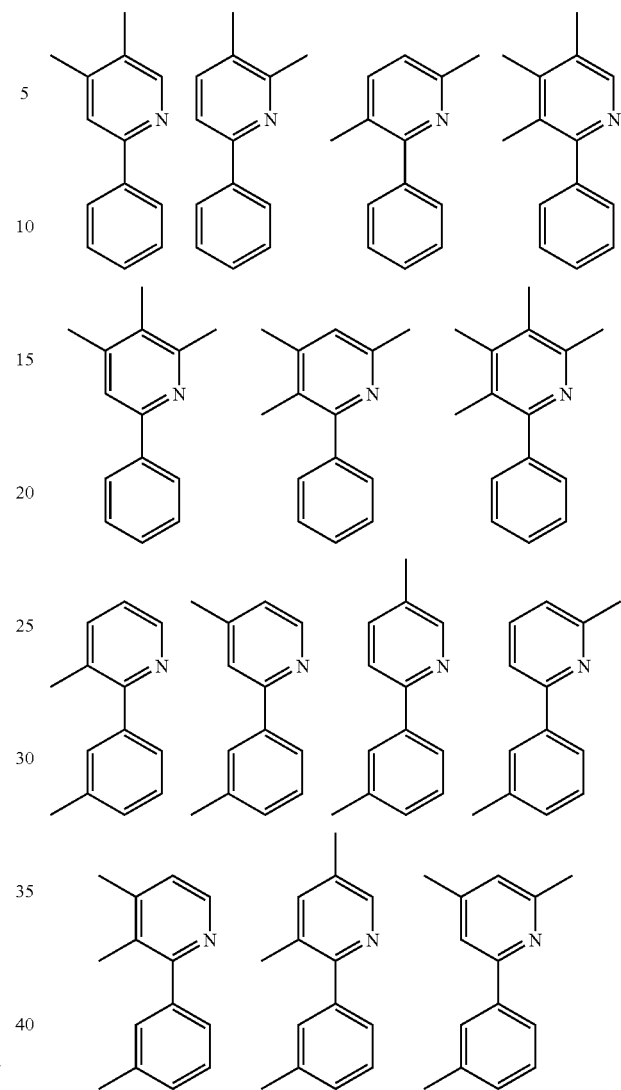
7. The compound of claim 1, wherein L2 is selected from the group consisting of:
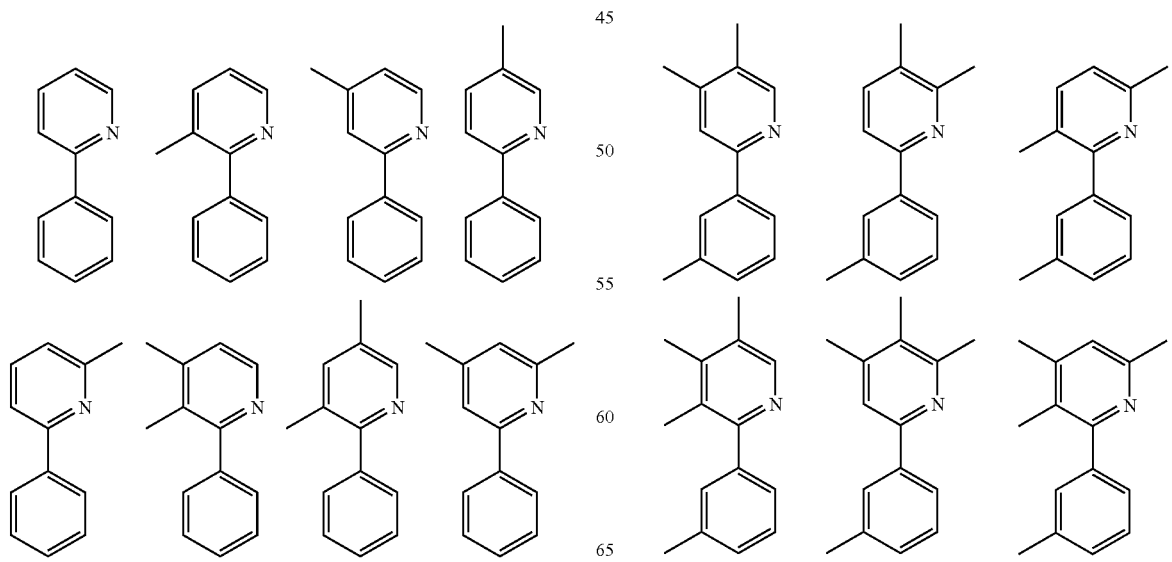

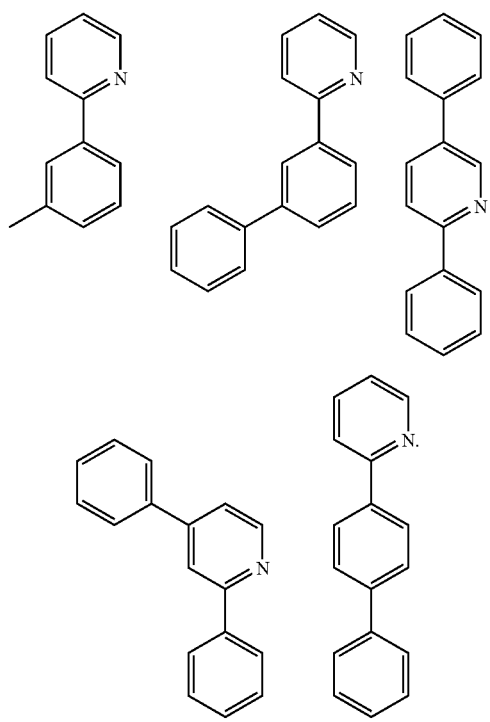
8. The compound of claim 1, wherein L1 is selected from the group consisting of:
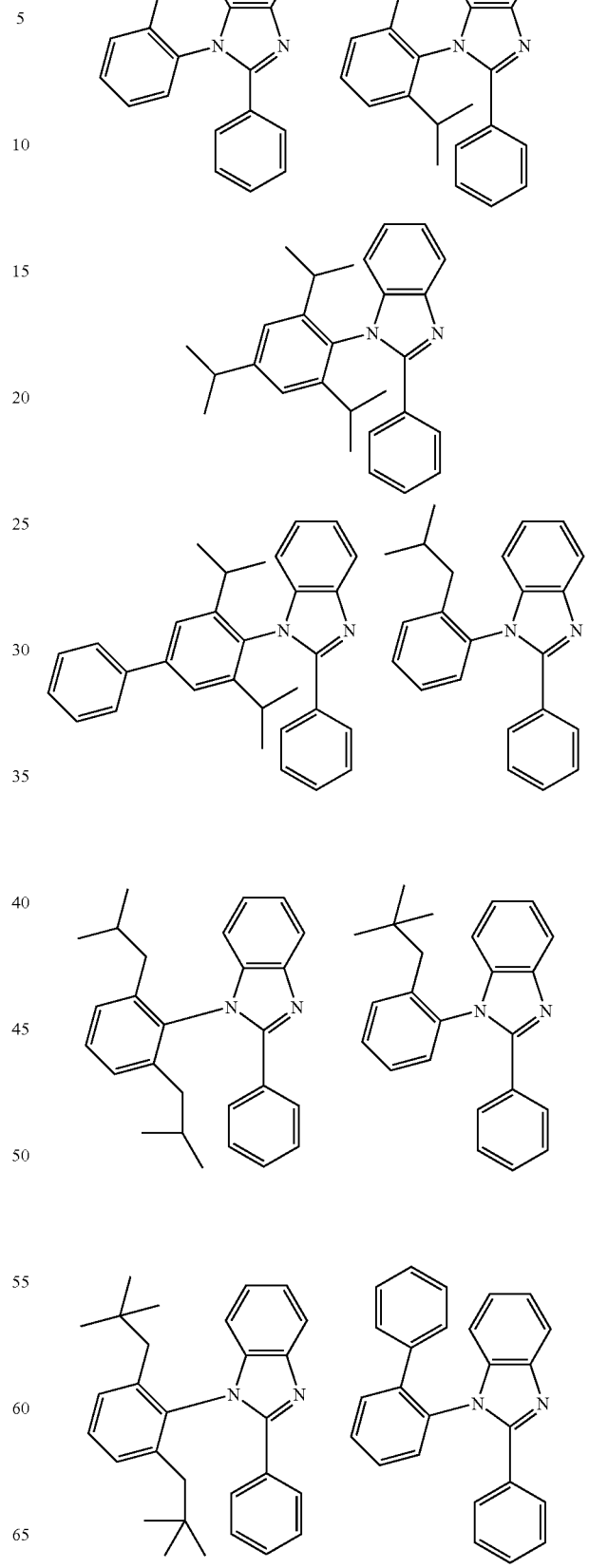

123
-continued
124
-continued
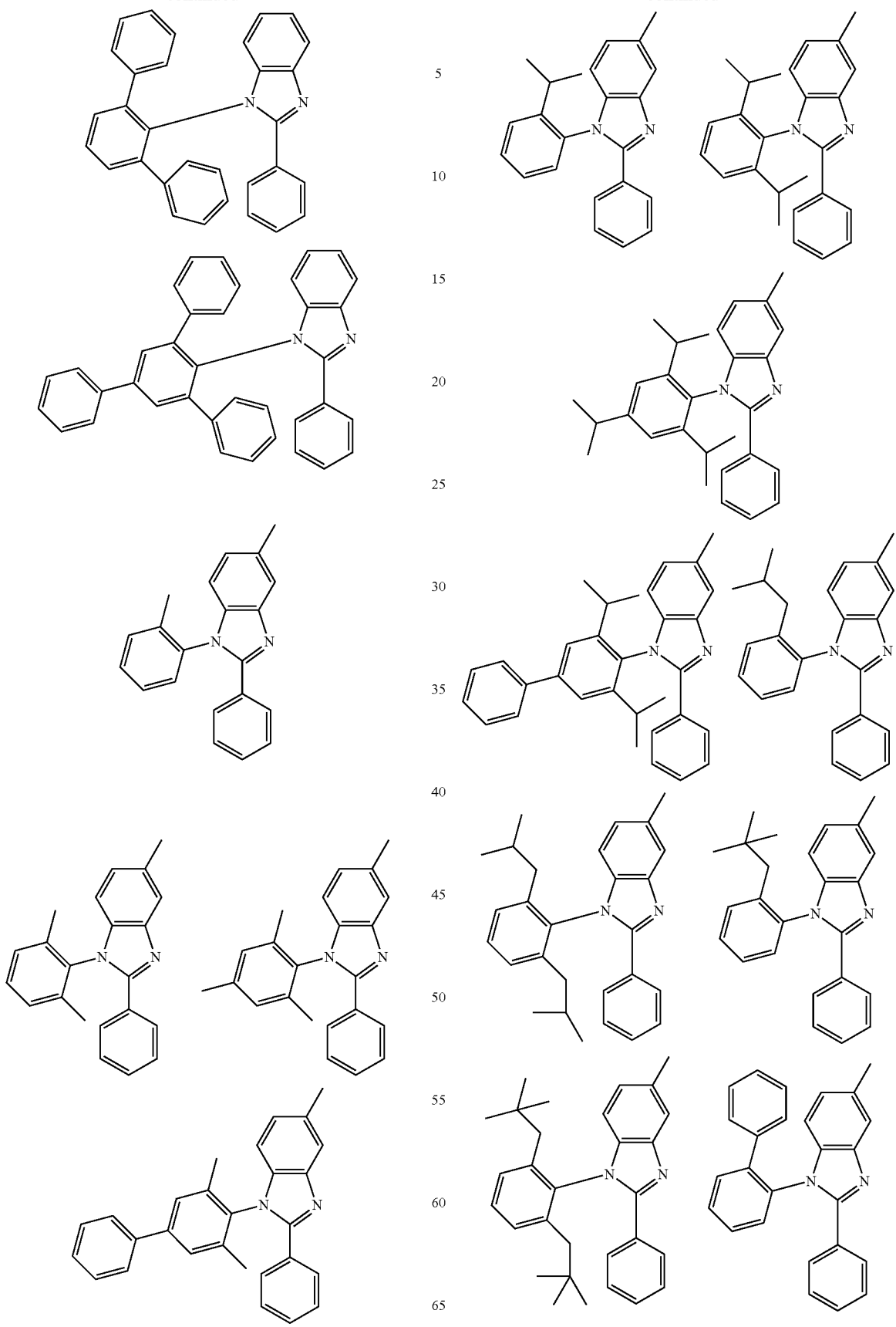

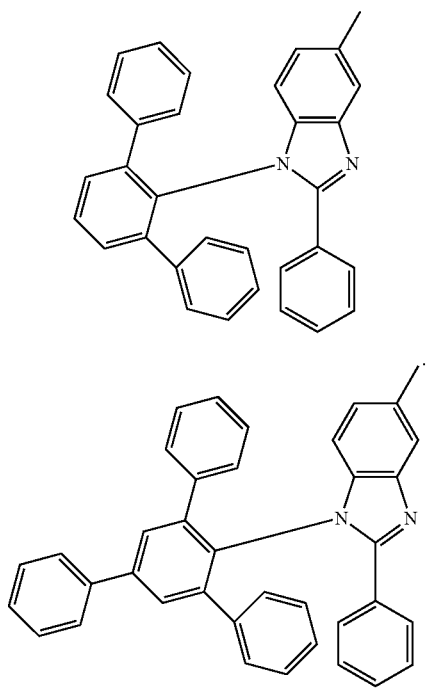
9. The compound of claim 8, wherein L2 is selected from the group consisting of:
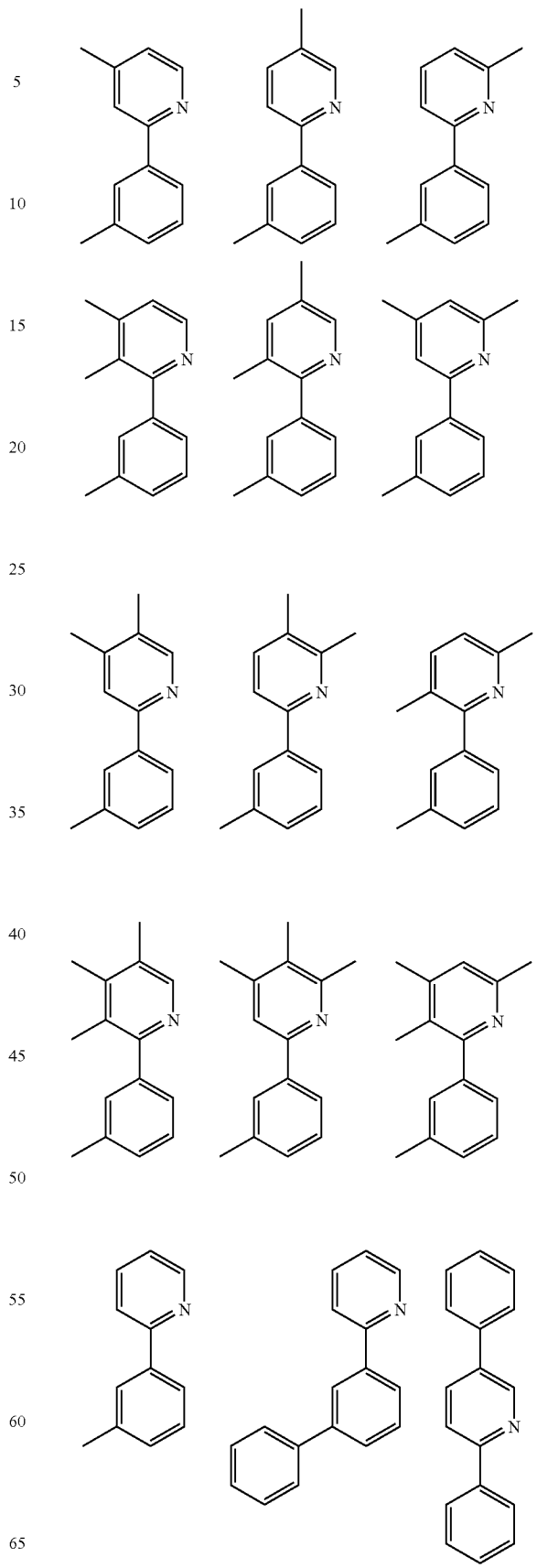

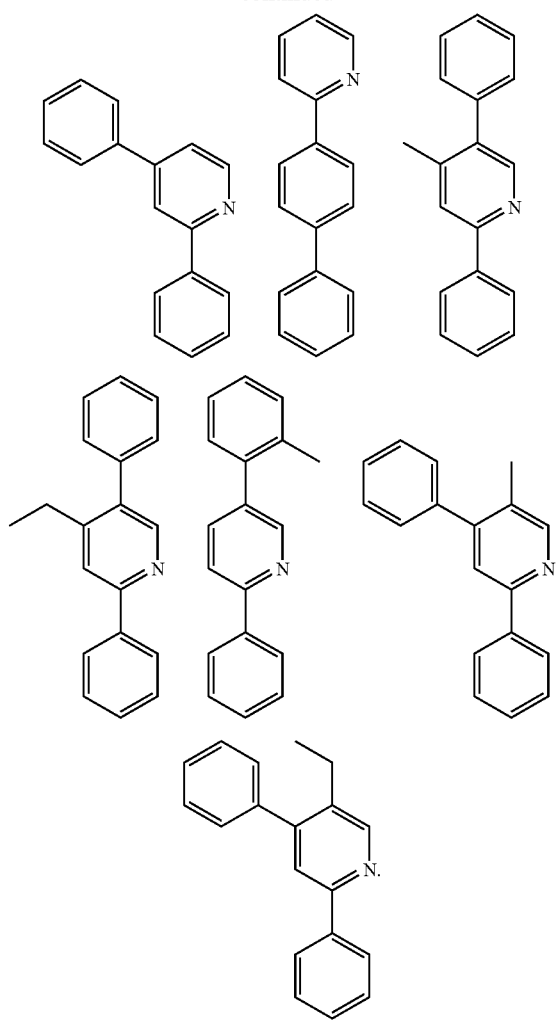
10. The compound of claim 1, wherein L2 is selected from the group consisting of:
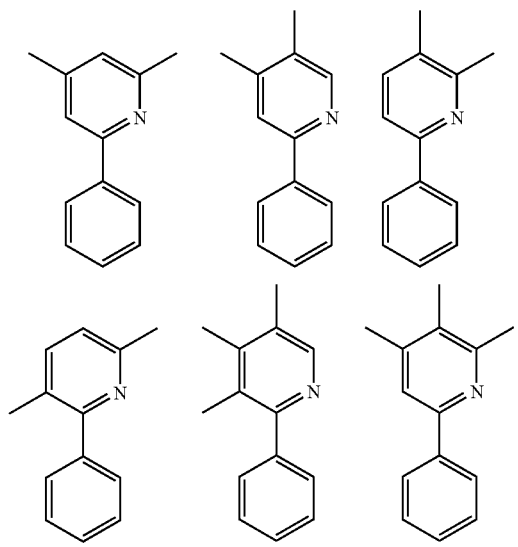
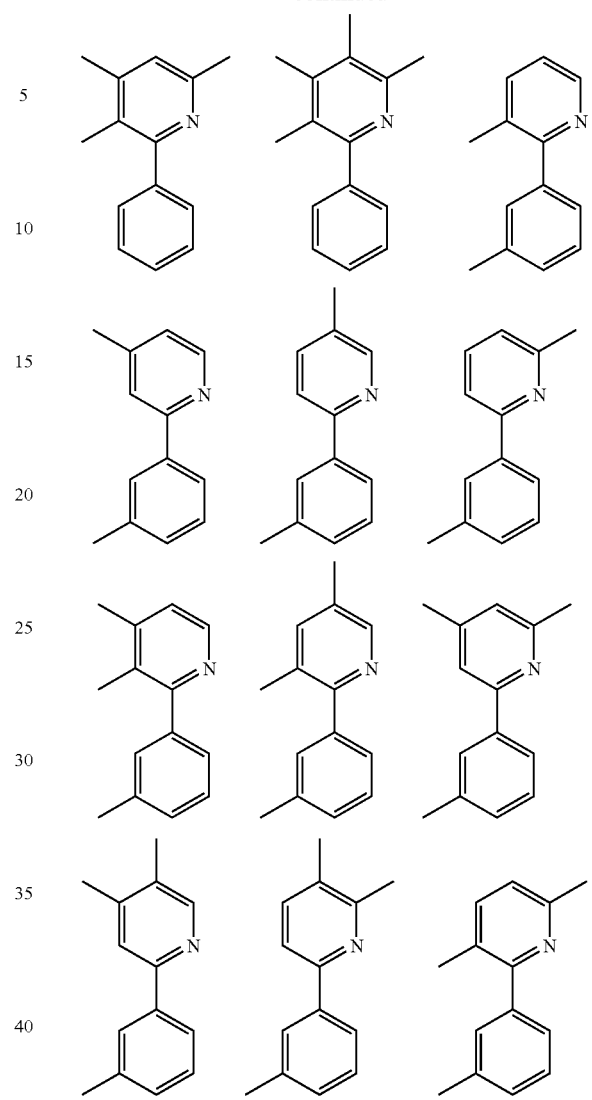
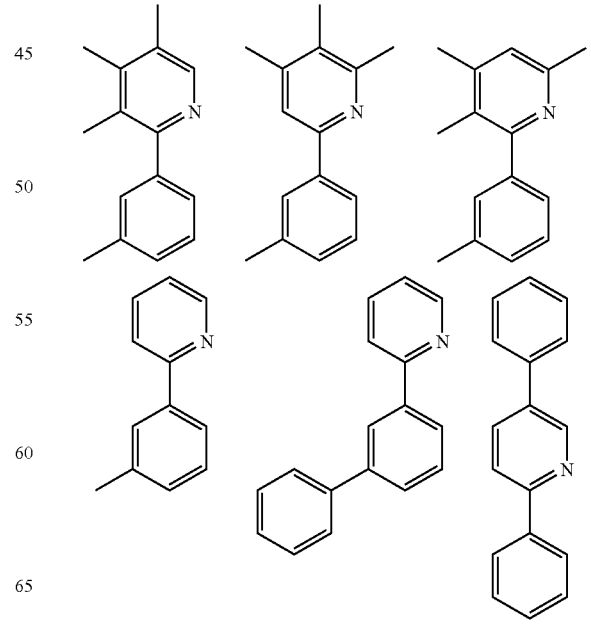

-continued
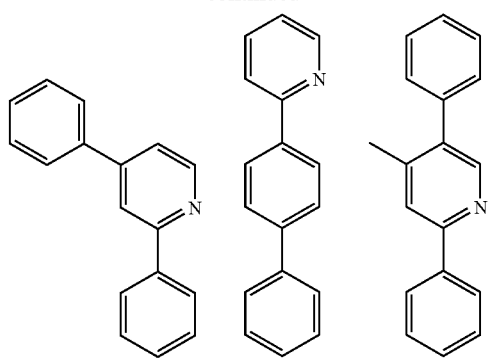
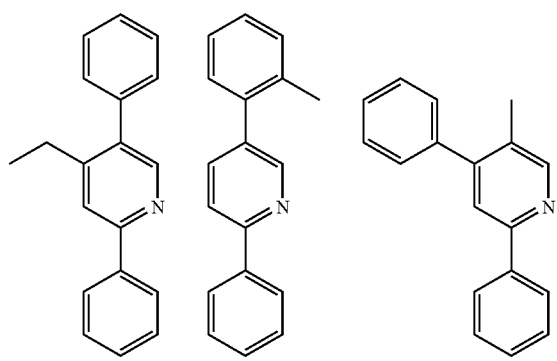
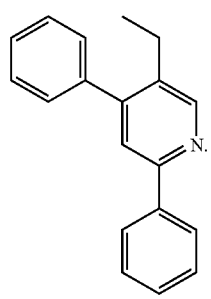 [SMILES: CCc1cnc(-c2ccccc2)cc1-c1ccccc1]
11. The compound of claim 1, wherein the compound is selected from the group consisting of:
-continued
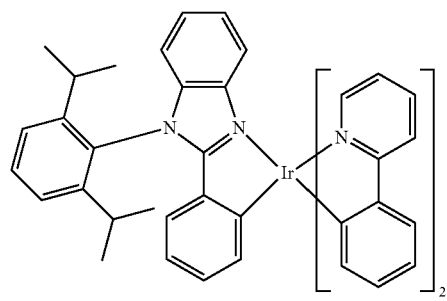
Compound 5
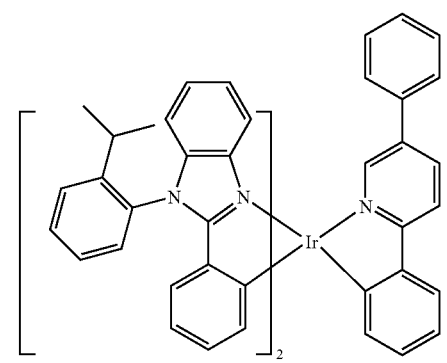
Compound 6
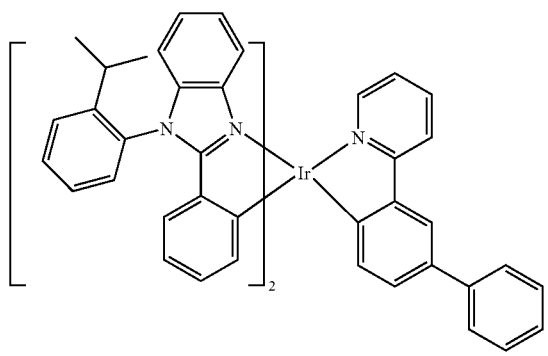
Compound 7
Compound 3
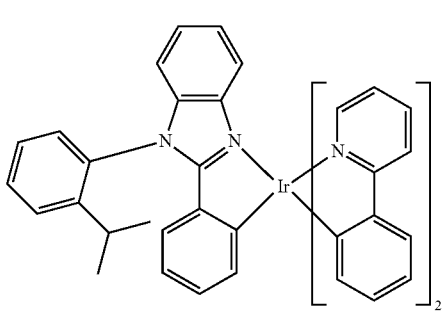
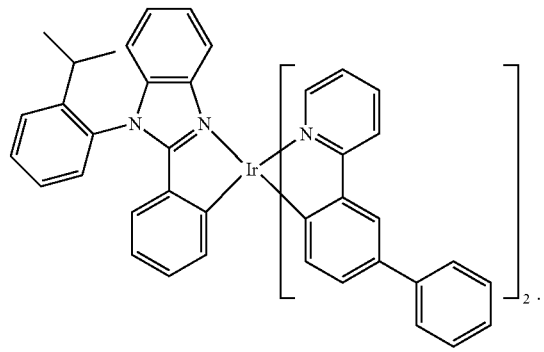
Compound 8

12. The compound of claim 1, wherein the compound is selected from the group consisting of:

Compound 3
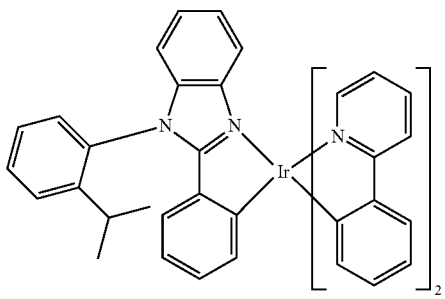

Compound 5
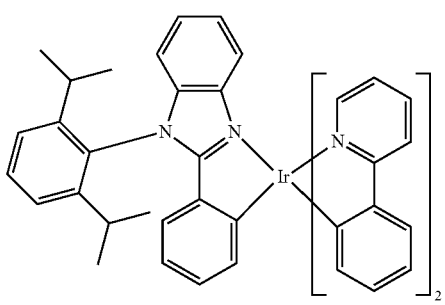

Compound 6
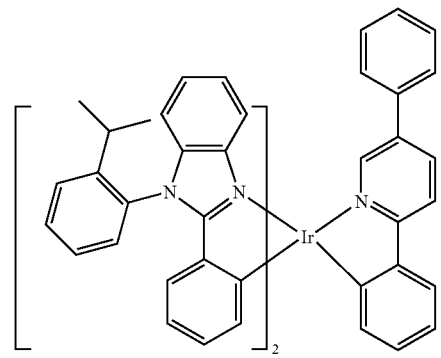

Compound 7
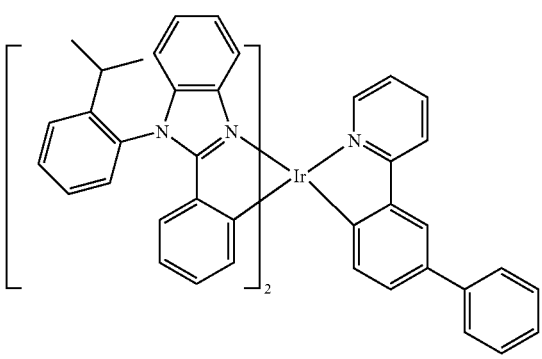

Compound 8
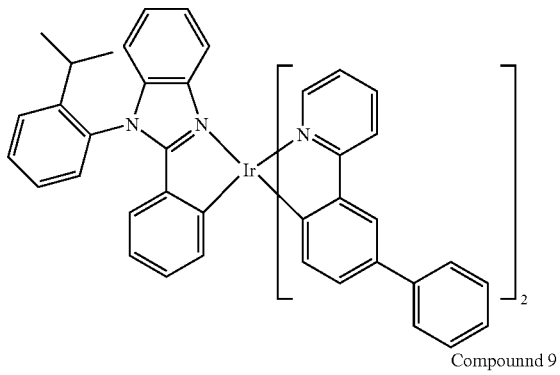

Compounnd 9
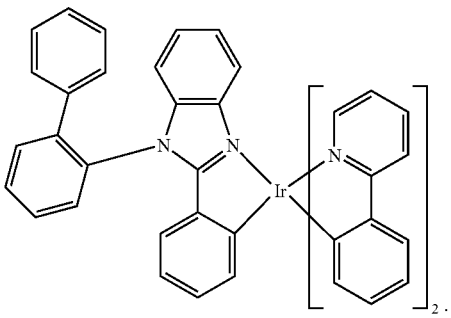

13. The compound of claim 1, wherein the compound has an emission spectrum with a narrower full width at half maximum than either
corresponding compound of formula

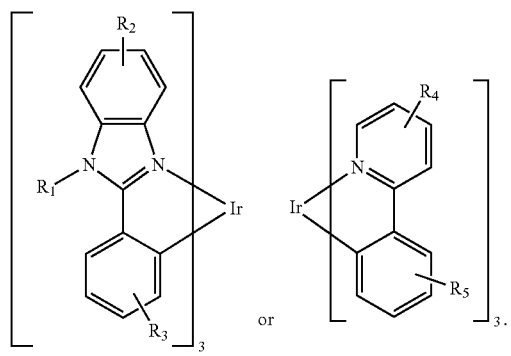

14. The compound of claim 1, wherein the compound has a lower sublimation temperature than either
corresponding compound of formula

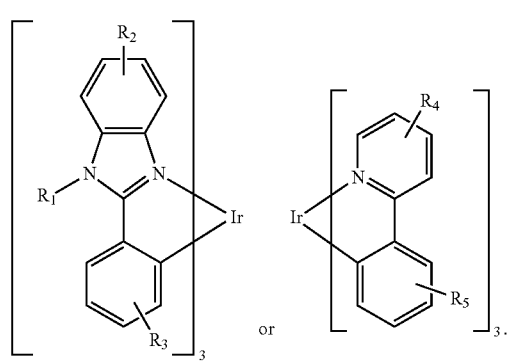

15. The compound of claim 1, wherein the compound is capable of being a green emissive dopant.

16. An organic light emitting device comprising:
an anode;
a cathode; and
an organic layer, disposed between the anode and the cathode, the organic layer comprising a heteroleptic iridium compound $Ir(L1)_n(L2)_{3-n}$ having the formula:

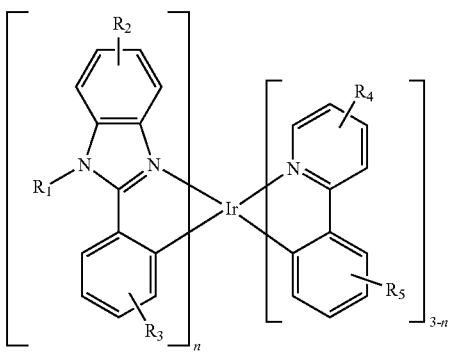

wherein n=1 or 2;
wherein

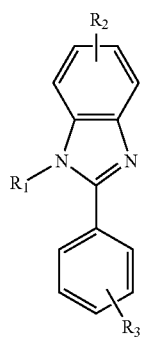

is L1;
wherein

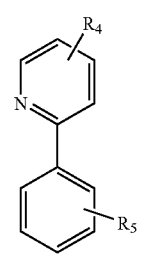

is L2;
wherein $R_2$, $R_3$, $R_4$, and $R_5$ may represent mono, di, tri, or tetra substitutions; and
wherein $R_2$, $R_3$, $R_4$, and $R_5$ are each independently selected from the group consisting of hydrogen, alkyl, heteroalkyl, aryl, substituted aryl, heteroaryl, and substituted heteroaryl;

wherein $R_1$ is

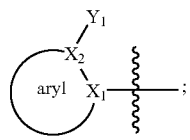

wherein $X_1$ and $X_2$ are independently selected from C and N;
wherein $Y_1$ is not hydrogen; and
wherein $Y_1$ may be joined to other substituents on the aryl ring.

17. The device of claim 16, wherein the organic layer is an emissive layer and the compound having the formula

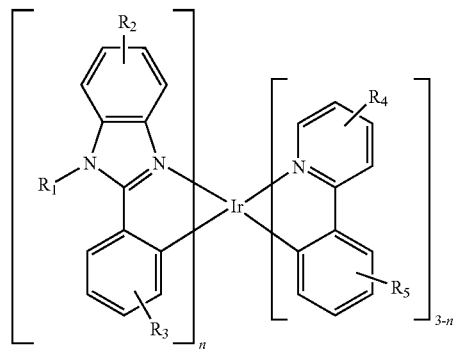

is an emissive compound.

18. The device of claim 16, wherein the compound is selected from the group consisting of:

Compound 3

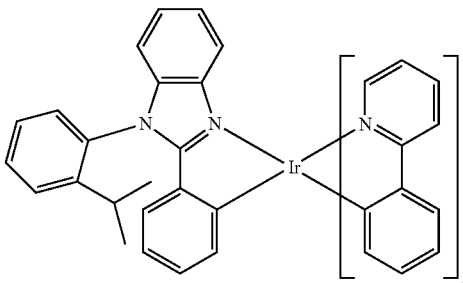

Compound 5

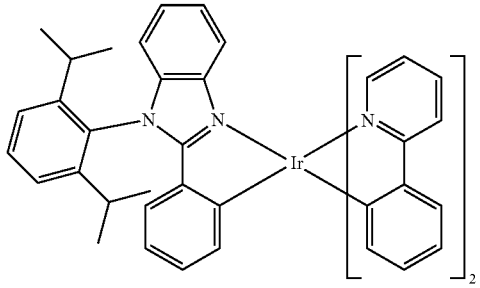

Compound 6
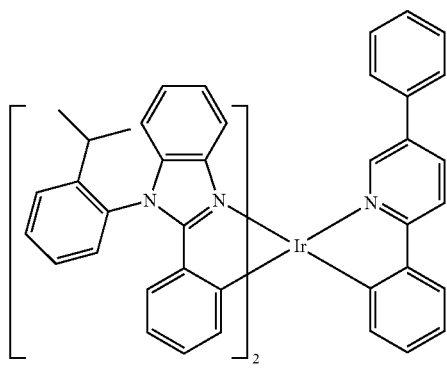
Compound 5
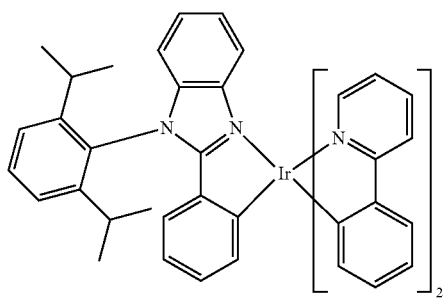
Compound 7
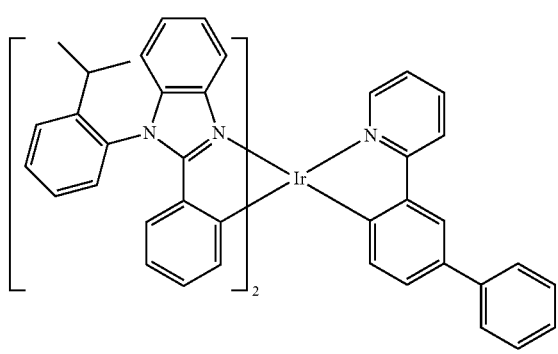
Compound 6
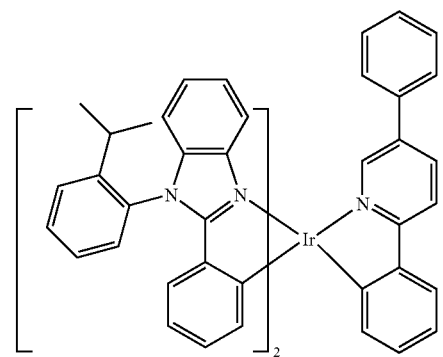
Compound 8
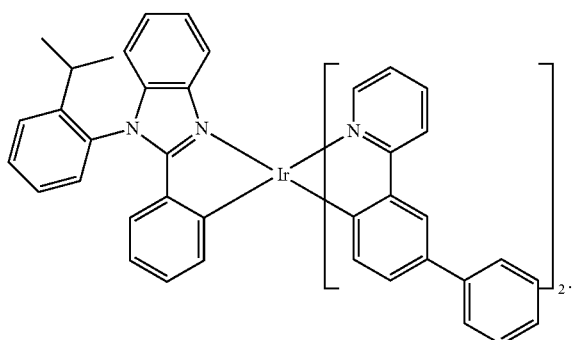
Compound 7
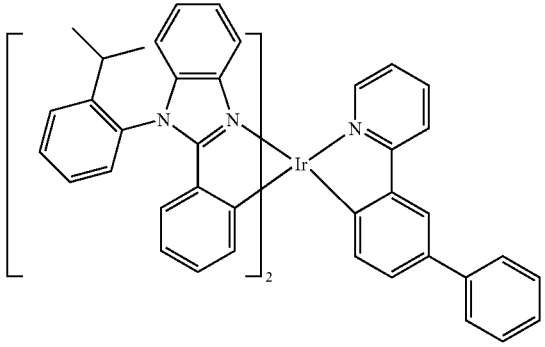
19. The device of claim 16, wherein the compound is selected from the group consisting of:
Compound 3
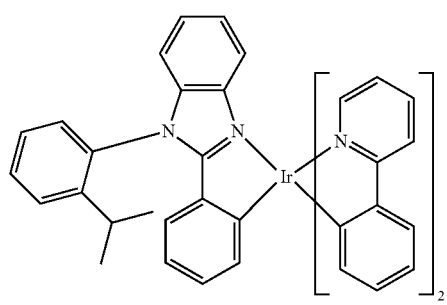
Compound 8
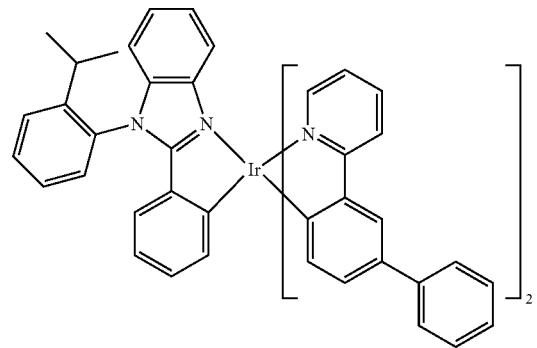

-continued

Compounnd 9

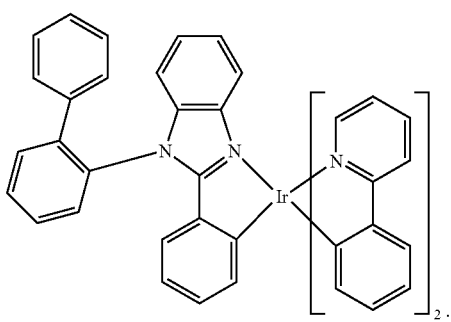

20. The device of claim 16, wherein the organic layer further comprises a host.

21. The device of claim 20, wherein the host has the formula:

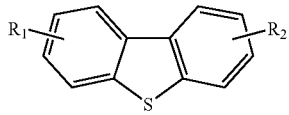

wherein $R_1$ and $R_2$ represent, independently, mono, di, tri or tetra substitutions selected from alkyl, alkoxy, amino, alkenyl, alkynyl, arylkyl, aryl and heteroaryl, or no substitution; and
wherein at least one of $R_1$ and $R_2$ includes a triphenylene group.

22. The device of claim 20, wherein the host has the formula:

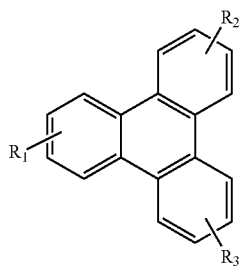

wherein each of $R_1$, $R_2$, and $R_3$ is independently a hydrogen, a non-fused aryl group, or a non-fused heteroaryl group having one or more meta-substituents, wherein at least one of $R_1$, $R_2$, and $R_3$ is not hydrogen; and
wherein each meta-substituent is a non-fused aryl or heteroaryl group optionally substituted with further substituents selected from the group consisting of non-fused aryl groups, non-fused heteroaryl groups, and alkyl groups.

23. A consumer product comprising a device, the device comprising:
an anode;
a cathode; and
an organic layer, disposed between the anode and the cathode, the organic layer comprising a heteroleptic iridium compound $Ir(L1)_n(L2)_{3-n}$ compound having the formula:

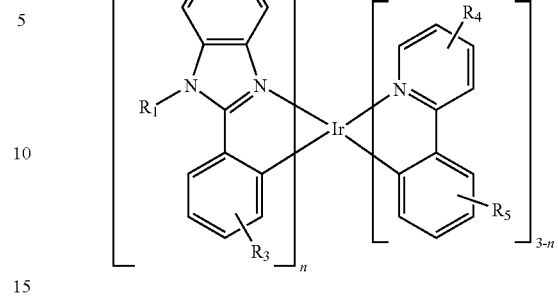

wherein n=1 or 2;
wherein

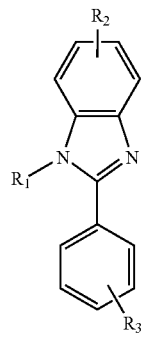

is L1;
wherein

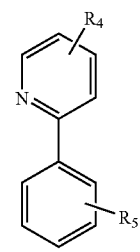

is L2;
wherein $R_2$, $R_3$, $R_4$, and $R_5$ may represent mono, di, tri, or tetra substitutions; and
wherein $R_2$, $R_3$, $R_4$, and $R_5$ are each independently selected from the group consisting of hydrogen, alkyl, heteroalkyl, aryl, substituted aryl, heteroaryl, and substituted heteroaryl;
wherein $R_1$ is

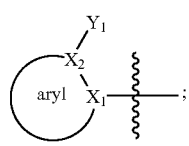

wherein $X_1$ and $X_2$ are independently selected from C and N;
wherein $Y_1$ is not hydrogen; and
wherein $Y_1$ may be joined to other substituents on the aryl ring.

* * * * *